United States Patent
Hayama et al.

(10) Patent No.: US 6,914,062 B2
(45) Date of Patent: Jul. 5, 2005

(54) PYRAZINONE DERIVATIVES

(75) Inventors: Takashi Hayama, Ibaraki (JP); Nobuhiko Kawanishi, Ibaraki (JP); Tooru Takaki, Ibaraki (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 40 days.

(21) Appl. No.: 10/312,500

(22) PCT Filed: Jun. 28, 2001

(86) PCT No.: PCT/JP01/05545

§ 371 (c)(1),
(2), (4) Date: Jan. 31, 2003

(87) PCT Pub. No.: WO02/02550

PCT Pub. Date: Jan. 10, 2002

(65) Prior Publication Data

US 2003/0203907 A1 Oct. 30, 2003

(30) Foreign Application Priority Data

Jun. 30, 2000 (JP) ........................ 2000-200292

(51) Int. Cl.[7] .................. A01N 43/58; A01N 43/60; A61K 31/495; A61K 31/50; C07D 475/00
(52) U.S. Cl. ................. 514/249; 544/257; 544/350; 544/354
(58) Field of Search .............. 514/249; 544/257, 544/350, 354

(56) References Cited

FOREIGN PATENT DOCUMENTS

| DE | 1 804 328 | * | 5/1969 |
| EP | 0 371 564 | | 6/1990 |
| WO | 97/16447 | | 5/1997 |

OTHER PUBLICATIONS

Lu et al, Cancer Chemotherapy Pharmacol. vol. 46, pp. 293–304 (2000).*
John K. Buolamwini, Current Pharmaceutical Design, vol. 6, pp. 379–392 (2000).*
Jungmann and Pfleiderer "A New Efficient Method in Nucleoside Synthesis" Tetrahedron Letters, vol. 37(46), pp. 8355–8358 (1996).*
Chemical Abstracts, vol. 100, abstract No. 34499.
Chemical Abstracts, vol. 81, abstract No. 120578.

* cited by examiner

*Primary Examiner*—James O. Wilson
*Assistant Examiner*—Zachary C. Tucker
(74) *Attorney, Agent, or Firm*—Wenderoth, Lind & Ponack, L.L.P.

(57) ABSTRACT

The present invention relates to a compound of the general formula (I):

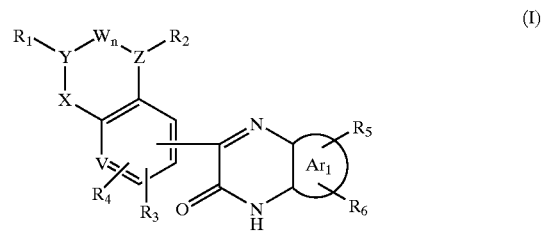

(I)

[$Ar_1$ is aryl fused to the adjacent pyrazinone ring at the 5th and 6th positions, etc., X is CO, etc., Y is CH, etc., Z is CH, etc., V is CH, etc., $W_n$ is —$(CH_2)_n$— (n is zero to four), $R_1$ is H or optionally substituted lower alkyl, etc., $R_2$ is H, etc., $R_3$ and $R_4$ are the same or different and are each H, etc., $R_5$ and $R_6$ are the same or different and are each H, hydroxy, etc.] or a pharmaceutically acceptable salt or ester thereof; a pharmaceutical composition, an inhibitor of Cdk4 and/or Cdk6 or an anti-cancer agent, containing the same as an active ingredient; and a process for preparing them.

13 Claims, No Drawings

PYRAZINONE DERIVATIVES

This application is a U.S. National Stage of International Application No. PCT/JP01/05545 filed Jun. 28, 2001.

TECHNICAL FIELD

The present invention relates to a 2(1H)-pyrazinone fused aromatic or heterocyclic derivative useful as pharmaceuticals, a process for preparing the same and a composition containing the same as an active ingredient.

BACKGROUND ART

In normal cell, cell division and its pause occur orderly in accordance with cell cycle, while cancer cell is, on the contrary, characterized by its disorderedness. For this reason abnormality of control mechanism in cell cycle is supposed to have direct relation with oncogenesis or malignant alteration of cancer. Cell cycle of mammalian cell is regulated by serine/threonine kinase called cyclin-dependent kinase (hereinafter abbreviated as to Cdk) family, and Cdk needs to form a complex with the regulatory subunit called cyclin in order to express its activity. Cyclin itself also have a family, and each Cdk molecule is considered to regulate the progression in certain cell cycle by forming a complex with specific cyclin molecule which is expressed at the corresponding stage of the cell cycle. For example, in combination with Cdk4 or Cdk6, D type cyclin regulates the progression of G1 phase, cyclin E-Cdk2 regulates G1/S boundary, cyclin A-Cdk2 regulates the progression of S phase, and cyclin B-cdc2 regulates the progression of G2/M. In addition, three sub-types, D1, D2 and D3 are known as D type cyclin, and moreover the activity of Cdk is considered to be controlled not only by combination with cyclin but also by phosphorylation/dephosphorylation of Cdk molecule, degradation of cyclin molecule and binding with Cdk inhibitor proteins (Advanced Cancer Research, Vol. 66, pp 181–212(1995); Current Opinion in Cell Biology, Vol. 7, pp773–780(1995): Nature, Vol.374, pp131–134 (1995)).

Cdk inhibitor proteins in mammalian cell are classified roughly into two kinds, Cip/Kip family and INK4 family due to the differences in structure and behavior. Compared to that the former inhibits cyclin-Cdk complex widely, the latter inhibits cyclin-Cdk complex specifically, as a result of binding with Cdk4 or Cdk6 (Nature, vol. 366, pp704–707 (1993); Molecular and Cellular Biology, vol.15, pp2627–2681(1995): Genes and Development, vol.9, pp1149–1163 (1995)).

For example, P21(Sdi1/Cip1/Waf1) is nominated for a representative example of the former and its expression is induced by cancer repressor gene product, p53.

On the other hand, for example, p16 (INK4a/MTS1/CDK4I/CDKN2) is one of the Cdk inhibitor protein which belongs to the latter. Human P16 gene is encoded on the chromosome 9p21. Abnormalities of this locus are detected with a high frequency in human cancer cell. Actually many reports according to the deletion and mutation of the p16 gene are made in clinical field. And high-frequency of tumorigenesis in p16 knockout-mouse has been reported (Nature Genetics, vol.8, pp27–32(1994); Trends in Genetics, vol.11, pp136–140(1995); Cell, vol.85, pp27–37(1996)).

Each Cdk controls the progression of cell cycle by phosphorylation of a certain target protein at the specific phase of cell cycle, and, above all, retinoblastoma (RB) protein is considered to be the most important target protein. RB protein is the protein which plays an important role in progression from G1 phase to S phase and is rapidly phosphorylated during the term from late G1 phase to initial S phase. This phosphorylation is considered to be carried out by cyclin D-Cdk4/Cdk6 complex followed by cyclin E-Cdk2 complex during the progression of cell cycle. The complex composed of hypophosphorylated RB and transcription factor E2F at early G1 phase dissociates when RB protein becomes hyperphosphorylated. As a result, E2F will be the transcriptional activator, and at the same time, the suppression of the promoter activity by RB-E2F complex will be removed, thus leading to the activity of E2F dependent transcription. At present, the Cdk-RB pathway, which consists of E2F, its suppressor RB protein, Cdk4/Cdk6 which repressively regulates the function of RB protein, Cdk inhibitor protein which controls the kinase activity of Cdk4/Cdk6 and D-type cyclin is thought to be the important mechanism to regulate the progression of GI phase to S phase (Cell, vol.58, pp1097–1105(1989); Cell, vol.65, pp1053–1061(1991); Oncogene, vol.7, pp1067–1074 (1992); Current Opinion in Cell Biology, Vol. 8, pp805–814 (1996); Molecular and Cellular Biology, vol. 18, pp753–761 (1998)). In fact, E2F-binding DNA sequence is located upstream of the sequence related to cell growth relative genes, and in several genes among them the transcription is reported to be activated during the term from late G1 phase to initial S phase(The EMBO Journal, vol.9, pp 2179–2184, (1990); Molecular and Cellular Biology, vol. 13, pp1610–1618 (1993)).

Abnormalities of any factors which intervene in Cdk-RB route, for example, deletion of functional p16, high-expression of cyclin D1, high-expression of Cdk4 and deletion of functional RB protein are found in high frequency in human cancer (Science, vol.254, pp1138–1146 (1991); Cancer Research, Vol. 53, pp5535–5541 (1993); Current Opinion in Cell Biology, Vol. 8, pp805–814(1996). All of these promote the progression from G1 phase to S phase abnormally and it is obvious that this route plays an important role in malignant alteration or abnormal growth of cancer cells.

A series of chromone derivatives, for example, by flavopiridol are known as known compounds which have an inhibitory activity on Cdk family (WO 97/16447, 98/13344).

As the prior arts which are structurally similar to the compounds according to this invention, for example, Japanese patent publication Laid open No. 10-502630 (reference A), WO99/46260 (reference B), WO99/46264 (reference C), WO98/13368 (reference D), WO99/50254 (reference E), Japanese patent publication Laid open No. 11-149982 (reference F) and Japanese patent publication Laid open No. 04-182471(reference G) are nominated.

In reference A, substituted-2(1H)-pyridopyrazinone derivatives are disclosed. However, such compounds described in reference A are characterized in that they have a substituent other than hydrogen atom at position 1 of the pyrazinone ring, whereas the compounds according to the present invention are characterized in that the substituent at position 1 of the pyrazinone ring is fixed to hydrogen atom, so that the compounds of the present invention are completely different in chemical structure. Moreover, the use of the compounds described in reference A is related to the inhibition of TNF production and the inhibitor of phosphodiesterase IV production. Therefore the invention described in reference A is not directly related to the use based on the inhibition of Cdk4 and/or Cdk6 according to the present invention.

In references B, C and D, substituted-2(1H)-pyridopyrazinone derivatives are disclosed. However, these compounds described in each reference are characterized in that they have a 3-indolyl group at position 3 of the pyrazinone ring, whereas the compounds according to the present invention are characterized in that they have a substituted phenyl or a substituted pyridyl which is structurally different from substituted 3-indolyl. Therefore the compounds according to the present invention are completely different in their chemical structure. Moreover, the use of the compounds described in references B, C and D is intended for cancer, inflammation, immune disorder, bronchopulmonary disorder, heart disease, and the like caused by the inhibition of proteinkinase C, so these inventions in references B, C and D are not directly related to the use based on the inhibition of Cdk4 and/or Cdk6 according to the present invention.

In reference E, heterocyclic compounds including substituted-2(1H)-pyridopyrazinone derivatives are disclosed. The compounds described in references E are however characterized in that they have a substituent other than hydrogen atom at position 3 of the pyrazinone ring, whereas the compounds according to the present invention are characterized in that the substituent at position 1 of the pyrazinone ring is fixed to hydrogen atom. Therefore the compounds according to the present invention are completely different in their chemical structure. Moreover, the use of the compounds described in reference E are intended for a factor Xa inhibitor, and thus the invention in reference E is not directly related to the use based on the inhibition of Cdk4 and/or Cdk6 according to the present invention.

In references F and G, heterocyclic compounds including substituted 2(1H)-pyridopyrazinone derivatives are disclosed. However such compounds described in each reference are characterized in that they have a substituent other than hydrogen atom in the first position of the pyrazinone ring, whereas the compounds according to the present invention are characterized in that the substituent in the first position of pyrazinone ring is fixed to hydrogen atom. Therefore the compounds according to the present invention are completely different in chemical structure from such known compounds. Moreover, the uses of the compounds described in these references are for electroluminescence element and pigment, so these inventions in reference F and G are different far from this invention in the art to which they belong.

Therefore, the present invention refers to a novel compound and its manufacturing procedure which are not described in any references yet, and is not be able to be easily achieved by person skilled in the art on the basis of the above-mentioned references of A to G.

As mentioned above, chromon derivatives are referred to as the compounds which have an inhibiting activity for Cdk family, but the inhibiting activity for Cdk4 is not so enough that the compounds which have still more high-inhibiting activity are needed.

Moreover, the novel compounds which have, additionally, heterogeneous inhibitory activity for Cdk6 and the like are needed.

DISCLOSURE OF THE INVENTION

The present inventors have devoted themselves to research for the purpose of providing excellent compounds which have Cdk4- or Cdk6-inhibitory activity. As a result, they have discovered that novel compounds with 2(1H)-pyradinone structure have Cdk4 and/or Cdk6 inhibitory activity, and have completed the present invention.

More specifically, the present invention relates to a pyrazinone derivative of the general formula (I):

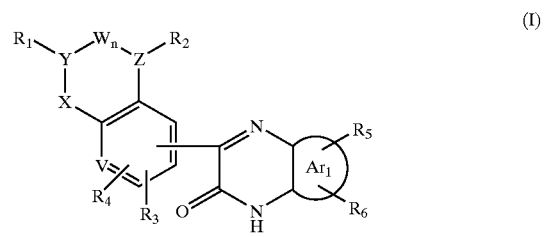

[wherein $Ar_1$ is an aryl group or a 5- or 6-membered aromatic heterocycle selected from the group consisting of pyridyl, pyrimidinyl, pyrrolyl, pyrazolyl, thienyl and pyrazinyl, said aryl or heterocycle being fused to the adjacent pyrazinone ring at the positions of 5 and 6;

X is CO, SO, $SO_2$ or NCOR (where R is hydrogen atom, lower alkyl, aryl or aralkyl {said lower alkyl, aryl or aralkyl may be optionally substituted by one or more substituents, which are the same or different, selected from the group consisting of hydroxy, carboxyl, carbamoyl and sulfamoyl});

Y is CH or N;

Z is CH, C, N, S or O (where when Z is C, then Z is taken together with $R_2$ to form CO; or when Z is S or O, Z is taken together with $R_2$ to form S or O, provided that when X is CO, then both Y and Z are not CH);

V is CH or N;

$W_n$ is $—(CH_2)_n—$ (n is 0, 1, 2, 3 or 4; when n is >0, one or more hydrogen atoms in the $—(CH_2)_n—$ may be substituted by the same or different lower alkyl ($R_w$); and when n is >0, one or two hydrogen atoms in the $—(CH_2)_n—$ may be substituted by the same or different lower alkyl ($R_w$); or when n is >0, $R_w$, taken together with $R_1$, Y and $W_n$, or with $R_2$, Z and $W_n$, or with one additional $R_w$ and $W_n$, may form a $C_5$–$C_8$ cycloalkyl group);

$R_1$ is a hydrogen atom; or lower alkyl, lower alkenyl or lower alkynyl (said lower alkyl, lower alkenyl or lower alkynyl may have one or more substituents, which are the same or different, selected from the group consisting of <substituent group α>); or an aliphatic or aromatic ring substituent selected from the group consisting of $C_3$–$C_8$ cycloalkyl, $C_5$–$C_8$ cycloalkenyl and aryl (said aliphatic or aromatic ring substituent may have one or more substituents selected from the group consisting of a substituent selected from <substituent group α> and/or a substituent selected from lower alkyl and lower alkenyl where said lower alkyl and lower alkenyl may have one or more substituents, which are the same or different, selected from <substituent group α>), or lower alkyl substituted by said aliphatic or aromatic ring substituent; or a 5- or 6-membered aromatic or aliphatic heterocycle containing at least one of N, S and O, selected from the group consisting of <substituent group β> (said aromatic or aliphatic heterocycle may have one or more substituents selected from the group consisting of a substituent selected from <substituent group α> and/or a substituent selected from lower alkyl which may be substituted by one or more, the same or different, substituents selected from an aryl group and <substituent group β>), or lower alkyl substituted by said aromatic or aliphatic heterocycle;

$R_2$ is a hydrogen atom or lower alkyl (said lower alkyl optionally having the same or different, one or more substituents selected from the group consisting of hydroxy, cyano and lower alkoxy); or when n is 0, $R_2$, together with Z to which $R_2$ binds, Y and $R_1$, forms a 5- to 7-membered saturated aliphatic heterocycle selected from the group consisting of

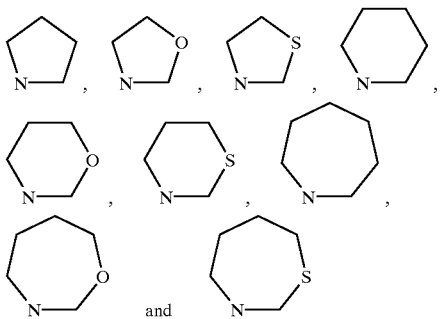

and which may contain at least one hetero atom selected from the group consisting of S and O, which is different from Y and/or Z (said saturated aliphatic heterocycle optionally having one or more substituents, which are the same or different, selected from the group consisting of a substituent selected from <substituent group α> and/or a substituent selected from the group of lower alkyl, lower alkenyl, aryl and aralkyl {said substituents may be substituted by one or more substituents, which are the same or different, selected from the group consisting of <substituent group α>}), provided that when Z is C, Z together with $R_2$ forms CO, or when Z is S or O, Z together with $R_2$ forms S or O);

$R_3$ and $R_4$ are, which are the same or different, a hydrogen atom, halogen atom, hydroxyl, amino; or lower alkyl, aryl or aralkyl (said lower alkyl, aryl or aralkyl may have one or more substituents, which are the same or different, selected from the group consisting of <substituent group α> and <substituent group γ>);

$R_5$ and $R_6$ are, which are the same or different, a hydrogen atom;

a substituent selected from the group consisting of <substituent group α> and <substituent group γ>;

the formula: $Y_1$—W—$Y_2$—$R_p$
(wherein $R_p$ is hydrogen atom; or lower alkyl, cyclo lower alkyl, lower alkenyl, lower alkynyl or aryl {said lower alkyl, cyclo lower alkyl, lower alkenyl, lower alkynyl or aryl may be substituted by one or more substituents, which are the same or different, selected from <substituent group α>}; or an aromatic heterocycle selected from <substituent group δ>; or an aliphatic heterocycle selected from <substituent group ε>, W is a single bond, oxygen atom, sulfur atom, sulfinyl, sulfonyl, $NR_q$, $SO_2NR_q$, $N(R_q)$, $SO_2NR_r$, $N(R_q)SO_2$, $CH(OR_q)$, $CONR_q$, $N(R_q)CO$, $N(R_q)CONR_r$, $N(R_q)COO$, $N(R_q)CSO$, $N(R_q)COS$, $C(R_q)=CR_r$, C≡C, CO, CS, OC(O), OC(O)$NR_q$, OC(S)$NR_q$, SC(O), SC(O)$NR_q$ or C(O)O (wherein $R_q$ and $R_r$ are each independently hydrogen atom, lower alkyl, aryl or aralkyl), $Y_1$ and $Y_2$ are the same or different and are each a single bond or a straight or branched lower alkylene}; or an aliphatic or aromatic ring substituent selected from the group consisting of $C_3$–$C_8$ cyclkoalkyl, $C_5$–$C_8$ cycloalkenyl and aryl (said aliphatic or aromatic ring substituent may be substituted by lower alkyl; lower alkyl which is substituted by $C_3$–$C_8$ cycloalkyl or aryl; or $C_3$–$C_8$ cycloalkyl), or a 5- to 6-membered aromatic or aliphatic heterocycle containing at least one of N, S and O, selected from <substituent group β> (said aromatic or aliphatic heterocycle may be substituted by lower alkyl; lower alkyl which is substituted by $C_3$–$C_8$ cycloalkyl or aryl; or $C_3$–$C_8$ cycloalkyl), wherein <substituent group α>, <substituent group β> <substituent group γ>, <substituent group δ>, and <substituent group ε> have each the meaning as shown below:

<Substituent Group α>:
hydroxyl, cyano, halogen atom, nitro, carboxyl, carbamoyl, formyl, lower alkanoyl, lower alkoxy, lower alkoxycarbonyl, lower alkylcarbonyloxy, lower alkylcarbamoyl, di-lower alkylcarbamoyl, carbamoyloxy, lower alkylcarbamoyloxy, di-lower alkylcarbamoyloxy, amino, lower alkylamino, di-lower alkylamino, tri-lower alkylammonio, lower alkanoylamino, aroylamino, lower alkanoylamidino, lower alkyl-sulfonylamino, hydroxyimino, lower alkoxyimino, lower alkylthio, lower alkylsulfinyl, lower alkylsulfonyl and sulfamoyl.

<Substituent Group β>:
pyrrolyl, pyrrolidyl, thienyl, furyl, thiazolyl, imidazolyl, pyrazolyl, oxazolyl, isoxazolyl, pyridyl, pyrimidinyl, pyrazinyl, piperidyl, piperazinyl and morpholinyl.

<Substituent Group γ>:
hydroxyl-lower alkyl, cyano-lower alkyl, halo-lower alkyl, carboxy-lower alkyl, carbamoyl-lower alkyl, amino-lower alkyl, lower alkylamino-lower alkyl, di(lower alkyl)amino-lower alkyl, and tri(lower alkylammonio)-lower alkyl.

<Substituent Group δ>:
imidazolyl, isoxazolyl, isoquinolyl, isoindolyl, indazolyl, indolyl, indolinyl, isothiazolyl, ethylenedioxyphenyl, oxazolyl, pyridyl, pyrazyl, pyrazinyl, pyrimidinyl, pyridazinyl, pyrazolyl, quinoxalinyl, quinolyl, dihydroisoindolyl, dihydroindolyl, thionaphthenyl, naphthyridinyl, phenazinyl, benzoimidazolyl, benzoxazolyl, benzothiazolyl, benzotriazolyl, benzofuranyl, thiazolyl, thiadiazolyl, thienyl, pyrrolyl, furyl, furazanyl, triazolyl and methylenedioxyphenyl.

<Substituent Group ε>:
imidazolidinyl, tetrahydrofuranyl, piperazinyl, piperidyl, pyrrolidyl, pyrrolinyl, morpholino, tetrahydroquinolyl and tetrahydroisoquinolyl], or a pharmaceutically acceptable salt or ester thereof.

The symbols and terms described in the present specification will be explained.

The term "aryl" in the above formula (I) refers to an aromatic hydrocarbon group of $C_5$ to $C_{15}$, for example, phenyl, indenyl, naphthyl or the like, preferably phenyl.

The term "a 5- or 6-membered aromatic heterocycle" in the above formula (I) refers to, for example, pyridyl, pyrimidinyl, pyrrolyl, pyrazolyl, thienyl, pyrazinyl or the like, preferably, pyridyl, pyrimidinyl, pyrrolyl, pyrazolyl or thienyl, more preferably pyridyl or pyrimidinyl.

The term "lower alkyl" in the above formula (I) refers to a straight- or branched-chain alkyl group of $C_1$ to $C_6$, for example, methyl, ethyl, propyl, isopropyl, butyl, isobutyl, sec-butyl, tert-butyl, pentyl, hexyl, or the like, preferably methyl, ethyl, propyl, isopropyl, tert-butyl, or pentyl, particularly preferably methyl, ethyl, propyl, or isopropyl.

The term "lower alkenyl" in the above formula (I) refers to a straight- or branched-chain alkenyl group of $C_2$ to $C_6$, for example, vinyl, 1-propenyl, allyl, isopropenyl, 1-butenyl, 3-butenyl, 1,3-butanedienyl, 2-pentenyl, 4-pentenyl, 1-hexenyl, 3-hexenyl, 5-hexenyl or the like, preferably 1-propenyl, allyl, isopropenyl, or 1-butenyl.

The term "lower alkynyl" in the above formula (I) refers to a straight- or branched-chain alkynyl group of $C_2$ to $C_6$, for example, 2-propynyl, 2-butynyl, 3-butynyl, 2-pentynyl or the like, preferably 2-propynyl, or 2-butynyl.

The term "aralkyl" in the above formula (I) refers to the said lower alkyl group substituted with an "aryl" group, preferably, aralkyl of $C_7$ to $C_{15}$, for example, benzyl, α-methylbenzyl, phenethyl, 3-phenylpropyl, 1-naphthylmethyl, 2-naphthylmethyl, α-methyl(1-naphthyl)methyl, α-methyl(2-naphthyl)methyl, α-ethyl(1-naphthyl)methyl, α-ethyl(2-naphthyl)methyl, diphenylmethyl, dinaphthylmethyl or the like, preferably benzyl, α-methylbenzyl, or phenethyl.

The term "halogen atom" in the above formula (I) refers to, for example, fluorine atom, chlorine atom, bromine atom, iodine atom or the like, preferably fluorine atom, chlorine atom or bromine atom, more preferably fluorine atom.

The term "lower alkanoyl" in the above formula (I) refers to a group in which the carbonyl group is substituted by the said "lower alkyl" group, preferably is substituted by the alkyl group of $C_1$ to $C_5$, more specifically, acetyl, propionyl, butyryl, isobutyryl, valeryl, isovaleryl, pivaloyl, pentanoyl and the like, more preferably acetyl, propionyl, or pivaloyl.

The term "lower alkoxy" in the above formula (I) refers to a group in which an oxygen atom is substituted by "lower alkyl" group, concretely for example, methoxy, ethoxy, propoxy, isopropoxy, butoxy, isobutoxy, sec-butoxy, tert-butoxy, pentyloxy, neopentyloxy, hexyloxy, isohexyloxy or the like, more preferably methoxy, ethoxy, isopropoxy, or tert-butoxy, particularly preferably methoxy.

The term "lower alkoxycarbonyl" in the above formula (I) refers to a group in which a carbonyl group is substituted by the said "lower alkoxy", concretely for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, neopentyloxycarbonyl, hexyloxycarbonyl, isohexyloxycarbonyl, or the like, preferably methoxycarbonyl, ethoxycarbonyl, isopropoxycarbonyl, or tert-butoxycarbonyl, more preferably methoxycarbonyl, or ethoxycarbonyl.

The term "lower alkylcarbamoyl" in the above formula (I) refers to a group in which a carbamoyl group is N-substituted with the said "lower alkyl", for example, N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl, N-pentylcarbamoyl, N-hexylcarbamoyl or the like, preferably N-methylcarbamoyl, N-ethylcarbamoyl, or N-butylcarbamoyl.

The term "di-lower alkylcarbamoyl" in the above formula (I) refers to a group in which a carbamoyl group is N,N-disubstituted with the said "lower alkyl", for example, N,N-dimethylcarbamoyl, N,N-diethylcarbamoyl, N,N-dipropylcarbamoyl, N,N-diisopropylcarbamoyl, N,N-dibutylcarbamoyl, N,N-diisobutylcarbamoyl, N,N-di-tert-butylcarbamoyl, N,N-dipentylcarbamoyl, N,N-dihexylcarbamoyl, N-ethyl-N-methylcarbamoyl, N-methyl-N-propylcarbamoyl or the like, preferably N,N-dimethylcarbamoyl, N,N-diethylcarbamoyl, N,N-dibutylcarbamoyl, N-ethyl-N-methylcarbamoyl, or N-methyl-N-propylcarbamoyl.

The term "lower alkylcarbamoyloxy" in the above formula (I) refers to a group in which an oxygen atom is substituted with the said "lower alkylcarbamoyl", for example, N-methylcarbamoyloxy, N-ethylcarbamoyloxy, N-propylcarbamoyloxy, N-isopropylcarbamoyloxy, N-butylcarbamoyloxy, N-isobutylcarbamoyloxy, N-tert-butylcarbamoyloxy, N-pentylcarbamoyloxy, N-hexylcarbamoyloxy or the like, preferably N-methylcarbamoyloxy, N-ethylcarbamoyloxy, N-butylcarbamoyloxy.

The term "di-lower alkylcarbamoyloxy" in the above formula (I) refers to a group in which an oxygen atom is substituted with the said "di-lower alkylcarbamoyl", for example, N,N-dimethylcarbamoyloxy, N,N-diethylcarbamoyloxy, N,N-dipropylcarbamoyloxy, N,N-diisopropylcarbamoyloxy, N,N-dibutylcarbamoyloxy, N,N-diisobutylcarbamoyloxy, N,N-di-tert-butylcarbamoyloxy, N,N-dipentylcarbamoyloxy, N,N-dihexylcarbamoyloxy, N-ethyl-N-methylcarbamoyloxy, N-methyl-N-propylcarbamoyloxy or the like, preferably N,N-dimethylcarbamoyloxy, N,N-diethylcarbamoyloxy, N,N-dibutylcarbamoyloxy, N-ethyl-N-methylcarbamoyloxy, or N-methyl-N-propylcarbamoyloxy.

The term "lower alkylamino" in the above formula (I) refers to a group in which an amino group is N-substituted with the said "lower alkyl", for example, N-methylamino, N-ethylamino, N-propylamino, N-isopropylamino, N-butylamino, N-isobutylamino, N-tert-butylamino, N-pentylamino, N-hexylamino or the like, preferably N-methylamino, N-ethylamino, or N-butylamino.

The term "di-lower alkylamino" in the above formula (I) refers to a group in which an amino group is N,N-disubstituted with the said "lower alkyl", for example, N,N-dimethylamino, N,N-diethylamino, N,N-dipropylamino, N,N-diisopropylamino, N,N-dibutylamino, N,N-diisobutylamino, N,N-di-tert-butylamino, N,N-dipentylamino, N,N-dihexylamino, N-ethyl-N-methylamino, N-methyl-N-propylamino or the like, preferably N,N-dimethylamino, N,N-diethylamino, N,N-dibutylamino, N-ethyl-N-methylamino, or N-methyl-N-propylamino.

The term "tri-lower alkylammonio" in the above formula (I) refers to a group in which an amino group is N,N,N-trisubstituted with the said "lower alkyl", for example, N,N,N-trimethylammonio, N,N,N-triethylammonio, N,N,N-tripropylammonio, N,N,N-triisopropylammonio, N,N,N-tributylammonio, N,N,N-triisobutylammonio, N,N,N-tri-tert-butylammonio, N,N,N-tripentylammonio, N,N,N-trihexylammonio, N-ethyl-N,N-dimethylammonio, N,N-dimethyl-N-propylammonio or the like, preferably N,N,N-trimethylammonio, N,N,N-triethylammonio, N,N,N-tributylammonio, N-ethyl-N,N-dimethylammonio, or N,N-dimethyl-N-propylammonio.

The term "lower alkanoylamino" in the above formula (I) refers to a group in which an amino group is substituted with the said "lower alkanoyl", for example, N-acetylamino, N-propionylamino, N-butyrylamino or the like, preferably N-acetylamino, or N-propionylamino.

The term "aroylamino" in the above formula (I) refers to a group in which an amino group is substituted with an aroyl group, for example, N-benzoylamino, N-naphtylcarbonylamino or the like, preferably N-benzoylamino.

The term "lower alkanoylamidino" in the above formula (I) refers to a group in which an amidino group is substituted with the said "lower alkanoyl", for example, N-acetylamidino, N-propionylamidino, N-butyrylamidino or the like, preferably N-acetylamidino, or N-propionylamidino.

The term "lower alkoxyimino" in the above formula (I) refers to a group in which an imino group is substituted with the said "lower alkoxy", for example, methoxyimino, ethoxyimino, propoxyimino or the like, preferably, methoxyimino, or ethoxyimino.

The term "lower alkylthio" in the above formula (I) refers to a group in which a sulfur atom is substituted with the said "lower alkyl", for example, methylthio, ethylthio, propylthio, isopropylthio, butylthio, isobutylthio, tert-butylthio, pentylthio, hexylthio or the like, preferably methylthio, ethylthio, butylthio, or tert-butylthio.

The term "lower alkylsulfinyl" in the above formula (I) refers to a group in which a sulfinyl group is substituted with the said "lower alkyl", for example, methylsulfinyl, ethylsulfinyl, butylsulfinyl or the like, preferably methylsulfinyl, or ethylsulfinyl.

The term "lower alkylsulfonyl" in the above formula (I) refers to a group in which a sulfonyl group is substituted with the said "lower alkyl", for example, methylsulfonyl, ethylsulfonyl, butylsulfonyl or the like, preferably methylsulfonyl, or ethylsulfonyl.

The term "lower alkyl-sulfonylamino" in the above formula (I) refers to a group in which an amino group is N-substituted with the said "lower alkylsulfonyl", for example, N-methylsulfonylamino, N-ethylsulfonylamino, N-butylsulfonylamino or the like, preferably N-methylsulfonylamino, or N-ethylsulfonylamino.

The term "$C_3$–$C_8$ cycloalkyl" in the above formula (I) refers to, for example, cyclopropyl, cyclobutyl, cyclopentyl, cyclohexyl, cycloheptyl, cyclooctyl or the like, preferably cyclopentyl, or cyclohexyl.

The term "$C_5$–$C_8$ cycloalkenyl" in the above formula (I) refers to, for example, cyclopentenyl, cyclohexenyl, cycloheptenyl, cyclooctenyl or the like, preferably cyclohexenyl.

The term "a 5- or 6-membered aromatic or aliphatic heterocycle containing at least one of N, S and O" in the above formula (I) refers to, for example, pyrrolyl, pyrrolidyl, thienyl, furyl, thiazolyl, imidazolyl, pyrazolyl, oxazolyl, isoxazolyl, pyridyl, pyrimidinyl, pyrazinyl, piperidyl, piperazinyl, morpholinyl, or the like, preferably, pyrrolidyl, thiazolyl, imidazolyl, pyrazolyl, oxazolyl, isoxazolyl, pyridyl, pyrimidinyl, pyrazinyl, piperidyl, piperazinyl, or morpholinyl, more preferably pyrrolidyl, imidazolyl, pyridyl, pyrimidinyl, piperidyl, piperazinyl or morpholinyl and particularly preferably pyrrolidyl, pyridyl, pyrimidinyl, piperidyl, piperazinyl or morpholinyl.

The term "a 5- to 7-membered saturated aliphatic heterocycle" in the said (I) refers to, for example,

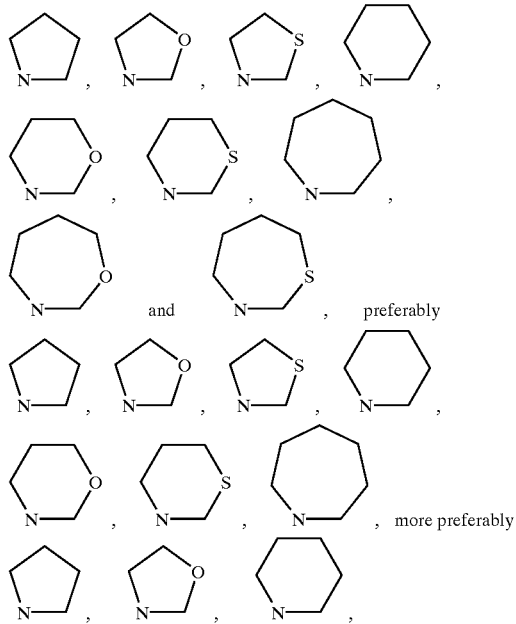

particularly preferably

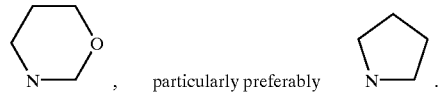

The term "hydroxy-lower alkyl" in the above formula (I) refers to the said "lower alkyl" substituted with a hydroxy group, for example, hydroxymethyl, dihydroxymethyl, trihydroxymethyl, 1-hydroxyethyl, 2-hydroxyethyl, 1-hydroxypropyl, 2-hydroxypropyl, 3-hydroxypropyl, 1-hydroxy-2-methylethyl, 1-hydroxybutyl, 1-hydroxy-2-methylpropyl, 1-hydroxy-2,2-dimethylethyl, 1-hydroxypentyl, 1-hydroxy-2-methylbutyl, 1-hydroxyhexyl, 1-hydroxy-2-methylpentyl or the like, preferably hydroxymethyl, 1-hydroxyethyl, 2-hydroxyethyl, or 1-hydroxy-2-methylethyl.

The term "cyano-lower alkyl" in the above formula (I) refers to the said "lower alkyl" group substituted with a cyano group, for example, cyanomethyl, 1-cyanoethyl, 2-cyanoethyl, 1-cyanopropyl, 2-cyanopropyl, 3-cyanopropyl, 1-cyano-2-methylethyl, 1-cyanobutyl, 1-cyano-2-methylpropyl, 1-cyano-2,2-dimethylethyl, 1-cyanopentyl, 1-cyano-2-methylbutyl, 1-cyanohexyl, 1-cyano-2-methylpentyl, or the like, preferably, cyanomethyl, 1-cyanoethyl, 2-cyanoethyl, or 1-cyano-2-methylethyl.

The term "halo-lower alkyl" in the above formula (I) refers to the "lower alkyl" group substituted with a halogen atom, for example, fluoromethyl, chloromethyl, bromomethyl, iodomethyl, difluoromethyl, dichloromethyl, trifluoromethyl, 1-fluoroethyl, 2-fluoroethyl, 1-chloroethyl, 2-chloroethyl, 1-chloropropyl, 2-chloropropyl, 1-fluoro-2-methylethyl, 1-chloro-2-methylethyl, 1-chlorobutyl, 1-chloro-2-methylpropyl, 1-chloro-2,2-dimethylethyl, 1-chloropentyl, 1-chloro-2-methylbutyl, 1-chlorohexyl, 1-chloro-2-methylpentyl, or the like, preferably, chloromethyl, trifluoromethyl, 1-fluoroethyl, 1-chloroethyl, or 1-chloro-2-methylethyl.

The term "carboxy-lower alkyl" in the above formula (I) refers to the said "lower alkyl" substituted with a carboxy group, for example, carboxymethyl, 1-carboxyethyl, 2-carboxyethyl, 1-carboxypropyl, 2-carboxypropyl, 3-carboxypropyl, 1-carboxy-2-methylpropyl, 1-carboxy-2,2-dimethylethyl, 1-carboxypentyl, 1-carboxy-2-methylbutyl, 1-carboxyhexyl, 1-carboxy-2-methylpentyl or the like, preferably carboxymethyl, 1-carboxyethyl, 2-carboxyethyl, or 1-carboxy-2-methylethyl.

The term "carbamoyl-lower alkyl" in the above formula (I) refers to the said "lower alkyl" substituted with a carbamoyl group, for example, carbamoylmethyl, 1-carbamoylethyl, 2-carbamoylethyl, 1-carbamoylpropyl, 2-carbamoylpropyl, 3-carbamoylpropyl, 1-carbamoyl-2-methylethyl, 1-carbamoylbutyl, 1-carbamoyl-2-methylpropyl, 1-carbamoyl-2,2-dimethylethyl, 1-carbamoylpentyl, 1-carbamoyl-2-methylbutyl, 1-carbamoylhexyl, 1-carbamoyl-2-methylpentyl or the like, preferably carbamoylmethyl, 1-carbamoylethyl, 2-carbamoylethyl, or 1-carbamoyl-2-methylethyl.

The term "amino-lower alkyl" in the above formula (I) refers to the said "lower alkyl" group substituted with an amino group, for example, aminomethyl, 1-amino, 2-aminoethyl, 1-aminopropyl, 2-aminopropyl, 3-aminopropyl, 1-amino-2-methylethyl, 1-aminobutyl, 1-amino-2-methylpropyl, 1-amino-2,2-dimethylethyl, 1-aminopentyl, 1-amino-2-methylbutyl, 1-aminohexyl, 1-amino-2-methylpentyl, or the like, preferably, aminomethyl, 1-aminoethyl, 2-aminoethyl, or 1-amino-2-methylethyl.

The term "lower alkylamino-lower alkyl" in the above formula (I) refers to "lower alkyl" substituted with the said "lower alkylamino", for example, N-methylaminomethyl, N-methylaminoethyl, N-methylaminopropyl, 1-methyl-2-(N-methylamino)ethyl, N-ethylaminomethyl, 2,2-dimethylethylaminomethyl or the like, preferably N-methylaminomethyl, or N-methylaminoethyl.

The term "di(lower alkyl)amino-lower alkyl" in the above formula (I) refers to "lower alkyl" substituted with the said "di-lower alkylamino", for example, N,N-dimethylaminomethyl, N,N-dimethylaminoethyl, N,N-dimethylaminopropyl, N,N-diethylaminomethyl, N,N-diethylaminoethyl or the like, preferably N,N-dimethylaminomethyl, or N,N-dimethylaminoethyl.

The term "tri(lower alkyl)ammonio)-lower alkyl" in the above formula (I) refers to "lower alkyl" substituted with the said "tri-lower alkylammonio", for example, N,N,N-trimethylammoniomethyl, N,N,N-trimethylammonioethyl, N,N,N-trimethylammoniopropyl, N,N,N-triethylammoniomethyl, N,N,N-triethylammonioethyl or the like, preferably N,N,N-trimethylammoniomethyl, or N,N,N-trimethylammonioethyl.

$Ar_1$ refers to an aryl group or a 5- or 6-membered aromatic heterocycle selected from the group consisting of pyridyl, pyrimidinyl, pyrrolyl, pyrazolyl, thienyl and pyrazinyl, $Ar_1$ being fused to the adjacent pyrazinone ring at the positions 5 and 6. Among those groups, an aryl group or a 5- or 6-membered aromatic heterocycle selected from the group consisting of pyridyl, pyrimidinyl, pyrrolyl, pyrazolyl and thienyl is preferred, phenyl, pyridyl or pyrimidinyl is more preferred, and phenyl is particularly preferred.

X is CO, SO, $SO_2$ or NCOR (where R is hydrogen atom, or lower alkyl, aryl or aralkyl, {said lower alkyl, aryl or aralkyl may be optionally substituted by one or more substituents, which are the same or different, selected from the group consisting of hydroxy, carboxyl, carbamoyl and sulfamoyl)), preferably CO or $SO_2$, more preferably CO.

Y is CH or N, preferably N.

Z is CH, C, N, S or O (where when Z is C, Z is taken together with $R_2$ to form CO; or when Z is S or O, Z is taken together with $R_2$ to form S or O, (provided that when X is CO, then both of Y and Z are not CH), preferably N, S or O, more preferably N or S.

V is CH or N, preferably CH.

$W_n$ is —$(CH_2)_n$— (n is 0, 1, 2, 3 or 4; and when n is >0, one or more hydrogen atoms in the —$(CH_2)_n$— group may be substituted by the same or different lower alkyl($R_w$); or when n is >0, $R_w$, taken together with $R_1$, Y and $W_n$, or taken together with $R_2$, Z and $W_n$, or taken together with one additional $R_w$ and $W_n$, may form a $C_5$–$C_8$ cycloalkyl group), and the case where $W_n$ is a single bond when n is 0 is preferred.

$R_1$ is hydrogen atom, or lower alkyl, lower alkenyl or lower alkynyl, among which lower alkyl is particularly preferred. Said lower alkyl, lower alkenyl or lower alkynyl may have one or more substituents, which are the same or different, selected from the group consisting of hydroxyl, cyano, halogen atom, nitro, carboxyl, carbamoyl, formyl, lower alkanoyl, lower alkoxy, lower alkoxycarbonyl, lower alkylcarbonyloxy, lower alkylcarbamoyl, di-lower alkylcarbamoyl, carbamoyloxy, lower alkylcarbamoyloxy, di-lower alkylcarbamoyloxy, amino, lower alkylamino, di-lower alkylamino, tri-lower alkylammonio, lower alkanoylamino, aroylamino, lower alkanoylamidino, lower alkyl-sulfonylamino, hydroxyimino, lower alkoxyimino, lower alkylthio, lower alkylsulfinyl, lower alkylsulfonyl and sulfamoyl (these are the same as those in the <substituent group α> in the above formula (I), and <substituent group α> will be used in the following explanation of $R_1$). When the lower alkyl is substituted with a halogen atom (especially fluorine atom is preferred), the number of said halogen atom is preferably 1 to 5, more preferably 3 to 5, particularly preferably 3.

$R_1$ is an aliphatic or aromatic ring substituent selected from the group consisting of $C_3$–$C_8$ cycloalkyl, $C_5$–$C_8$ cycloalkenyl and aryl, or a lower alkyl group substituted by said aliphatic or aromatic ring substituent, preferably $C_5$–$C_6$ cycloalkyl, $C_5$–$C_6$ cycloalkenyl or aryl; or lower alkyl substituted by $C_5$–$C_6$ cycloalkyl, $C_5$–$C_6$ cycloalkenyl or aryl; especially preferably $C_5$–$C_6$ cycloalkyl or phenyl; or lower alkyl substituted by $C_5$–$C_6$ cycloalkyl or phenyl. Said aliphatic or aromatic cyclic substituent may have one or more substituents selected from the group consisting of a substituent selected from <substituent group α> and/or a substituent selected from lower alkyl and lower alkenyl where said lower alkyl and lower alkenyl may have one or more substituents, which are the same or different, selected from <substituent group α>.

$R_1$ is also a 5- or 6-membered aromatic or aliphatic heterocycle containing at least one of N, S and O, selected from the group consisting of pyrrolyl, pyrrolidyl, thienyl, furyl, thiazolyl, imidazolyl, pyrazolyl, oxazolyl, isoxazolyl, pyridyl, pyrimidinyl, pyrazinyl, piperidyl, piperazinyl and morpholinyl (these are the same as those consisting of <substituent group β> in the above formula (I), and are hereinafter referred to as <substituent group β> when $R_1$ is explained), or lower alkyl substituted by said aromatic or aliphatic heterocycle, among which pyrrolidyl, pyridyl, piperidyl or morpholinyl, or lower alkyl substituted by pyrrolidyl, pyridyl, piperidyl or morpholinyl are preferred. Said aromatic or aliphatic heterocycle may have optionally one or more substituents, which are the same or different, selected from the group consisting of a substituent selected from <substituent group α> and/or a lower alkyl which may be substituted by one or more substituents, the same or different, selected from <substituent group β> and an aryl group.

Moreover, in the aforesaid $R_1$, the <substituent group α> is preferably hydroxy, halogen atom, nitro, carboxyl, carbamoyl, lower alkanoyl, lower alkoxy, lower alkoxycarbonyl, lower alkoxycarbonyloxy, lower alkylcarbamoyl, di-lower alkylcarbamoyl, amino, lower alkylamino, di-lower alkylamino, lower alkanoylamino, aroylamino, lower alkyl-sulfonylamino, lower alkylsulfonyl and sulfamoyl, more preferably hydroxy, halogen atom, nitro, carboxyl, carbamoyl, lower alkoxy, lower alkoxycarbonyl, lower alkoxycarbonyloxy, lower alkylcarbamoyl, di-lower alkylcarbamoyl, amino, lower alkylamino, di-lower alkylamino, lower alkanoylamino, lower alkyl-sulfonylamino and lower alkylsulfonyl, particularly preferably hydroxy, halogen atom, nitro, carboxyl, lower alkoxy, lower alkoxycarbonyl and lower alkylcarbonyloxy.

Moreover, in the aforesaid $R_1$, the <substituent group β> is preferably pyrrolidyl, thiazolyl, imidazolyl, oxazolyl, isoxazolyl, pyridyl, pyrimidinyl, pyrazinyl, piperidyl, piperazinyl and morpholinyl, more preferably pyrrolidyl, pyridyl, pyrimidinyl, piperidyl, piperazinyl and morpholinyl, particularly preferably pyrrolidyl, pyridyl, piperidyl and morpholinyl.

$R_2$ is a hydrogen atom or lower alkyl; or when n is 0, $R_2$, together with Z to which $R_2$ binds, Y and $R_1$, forms a 5- to 7-membered saturated aliphatic heterocycle selected from the group consisting of

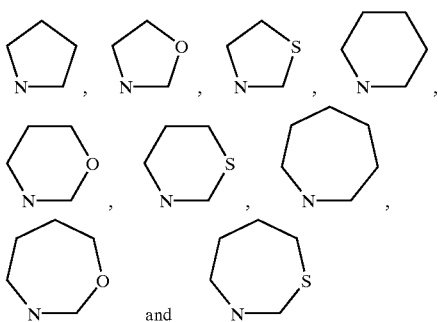

which may contain at least one hetero atom selected from the group consisting of S and O, which is different from Y and/or Z (provided that when Z is C, then $R_2$, together with Z, forms CO; and when Z is S or O, then $R_2$, together with Z, forms S or O). Said lower alkyl may be substituted by one or more substituents, which are the same or different, selected from the group consisting of hydroxy, cyano and lower alkoxy.

In the aforesaid $R_2$, said saturated aliphatic heterocycle may have one or more substituents, which are the same or different, selected from the group consisting of a substituent selected from hydroxy, cyano, halogen atom, nitro, carboxyl, carbamoyl, formyl, lower alkanoyl, lower alkoxy, lower alkoxycarbonyl, lower alkylcarbonyloxy, lower alkylcarbamoyl, di-lower alkylcarbamoyl, carbamoyloxy, lower alkylcarbamoyloxy, di-lower alkylcarbamoyloxy, amino, lower alkylamino, di-lower alkylamino, tri-lower alkylammonio, lower alkanoylamino, aroylamino, lower alkanoylamidino, lower alkyl-sulfonylamino, hydroxyimino, lower alkoxyimino, lower alkylthio, lower alkylsulfinyl, and lower alkylsulfonyl (these are the same as those consisting of <substituent group α> in the above formula (I), and are hereinafter referred to as <substituent group α> when $R_2$ is explained) and/or a substituent selected from the group consisting of lower alkyl, lower alkenyl, aryl and aralkyl {said these four substituents may have one or more substituents, the same or different, selected from <substituent group α>}.

Further, in the aforesaid $R_2$, said saturated aliphatic heterocycle is preferably a 5- to 7-membered saturated aliphatic heterocycle selected from the group consisting of

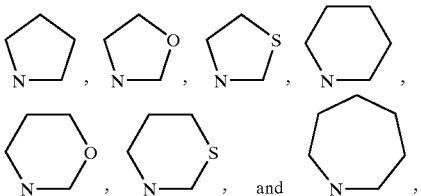

more preferably, a 5- or 6-membered saturated aliphatic heterocycle selected from the group consisting of

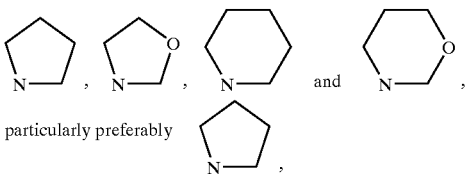

particularly preferably

wherein preferably $R_2$, together with Z, forms N, S or O or CO, or $R_2$ is hydrogen atom; and more preferably $R_2$, together with Z, forms N or S.

In the aforesaid $R_2$, <substituent group α> is preferably hydroxy, halogen atom, nitro, carboxyl, carbamoyl, lower alkanoyl, lower alkoxy, lower alkoxycarbonyl, lower alkylcarbonyloxy, lower alkylcarbamoyl, di-lower alkylcarbamoyl, amino, lower alkylamino, di-lower alkylamino, lower alkanoylamino, aroylamino, lower alkylsulfonylamino, lower alkylsulfonyl and sulfamoyl;

more preferably, hydroxy, halogen atom, nitro, carboxyl, carbamoyl, lower alkoxy, lower alkoxycarbonyl, lower alkoxycarbonyloxy, lower alkylcarbamoyl, di-lower alkylcarbamoyl, amino, lower alkylamino, di-lower alkylamino, lower alkanoylamino, lower alkylsulfonylamino and lower alkylsulfonyl;

particularly preferably, hydroxy, halogen atom, nitro, carboxyl, lower alkoxy, lower alkoxycarbonyl and lower alkylcarbonyloxy.

$R_3$ and $R_4$ are, which are the same or different, hydrogen atom, halogen atom, hydroxy, amino; or lower alkyl, aryl or aralkyl. Said lower alkyl, aryl or aralkyl may have one or more substituents, which are the same or different, selected from the group consisting of hydroxy, cyano, halogen atom, nitro, carboxyl, carbamoyl, formyl, lower alkanoyl, hydroxyl-lower alkyl, cyano-lower alkyl, halo-lower alkyl, carboxy-lower alkyl, carbamoyl-lower alkyl, lower alkoxy, lower alkoxycarbonyl, lower alkylcarbonyloxy, lower alkylcarbamoyl, di-lower alkylcarbamoyl, carbamoyloxy, lower alkylcarbamoyloxy, di-lower alkylcarbamoyloxy, amino, lower alkylamino, di-lower alkylamino, tri-lower alkylammonio, amino-lower alkyl, lower alkylamino-lower alkyl, di(lower alkylamino)-lower alkyl, tri(lower alkylammonio)-lower alkyl, lower alkanoylamino, aroylamino, lower alkanoylamidino lower alkyl, lower alkyl-sulfonylamino, hydroxyimino, lower alkoxyimino, lower alkylthio, lower alkylsulfinyl and lower alkylsulfonyl (these are the same as those consisting of <substituent group α> and <substituent group γ> in the above formula (I), and are hereinafter referred to as <substituent group α> and <substituent group γ> when $R_3$ and $R_4$ are explained), wherein $R_3$ and $R_4$, which are the same or different, are each preferably hydrogen atom, halogen atom, hydroxy, amino or lower alkyl, particularly preferably hydrogen atom.

Furthermore, in the aforesaid $R_3$ and $R_4$, the <substituent group α> is preferably hydroxy, halogen atom, nitro, carboxyl, carbamoyl, lower alkoxy, lower alkoxycarbonyl, lower alkylcarbonyloxy, lower alkanoyl, amino, lower alkylamino, di-lower alkylamino, lower alkylsulfonylamino and lower alkylsulfonyl;

more preferably hydroxy, halogen atom, nitro, carboxyl, carbamoyl, lower alkoxy, lower alkoxycarbonyl, lower alkylcarbonyloxy, amino, lower alkylamino, di-lower alkylamino, lower alkyl-sulfonylamino and lower alkylsulfonyl;

particularly preferably hydroxyl, halogen atom, nitro, carboxyl, lower alkoxy, lower alkoxycarbonyl and lower alkylcarbonyloxy.

Further in the above $R_3$ and $R_4$, the <substituent group γ> is preferably hydroxy-loweralkyl and halo-loweralkyl.

$R_5$ and $R_6$ may be the same or different, and each represents hydrogen atom; a substituent selected from the group consisting of hydroxy, cyano, halogen atom, nitro, carboxyl, carbamoyl, formyl, lower alkanoyl, hydroxy-lower alkyl, cyano-lower alkyl, halo-lower alkyl, carboxyl-lower alkyl, carbamoyl-lower alkyl, lower alkoxy, lower alkoxycarbonyl, lower alkylcarbamoyl, lower alkylcarbamoyl, di-lower alkylcarbamoyl, carbamoyloxy, lower alkylcarbamoyloxy, di-lower alkylcarbamoyloxy, amino, lower alkylamino, di-lower alkylamino, tri-lower alkylammonio, amino-lower alkyl, lower alkylamino-lower alkyl, di-lower alkylamino-lower alkyl, tri-lower alkylammonio-lower alkyl, lower alkanoylamino, aroylamino, lower alkanoylamidino-lower alkyl, lower alkylsulfonylamino, hydroxyimino and lower alkoxyimino, these groups being the same as <substituent group α> and <substituent group γ> of the above formula (I), and <substituent group α> and <substituent group γ> being used in the following explanation of $R^5$ and $R^6$; the formula: $Y_1$—W—$Y_2$—$R_p$ in which $Y_1$, W, $Y_2$ and $R_p$ are mentioned later; or an aliphatic or aromatic ring substituent selected from the group consisting of $C_3$–$C_8$ cycloalkyl, $C_5$–$C_8$ cycloalkenyl and aryl; or a 5- to 6-membered aromatic or aliphatic heterocycle containing at least one of N, S or O, which is selected from the group consisting of pyrrolyl, pyrrolidyl, thienyl, furyl, thiazolyl, imidazolyl, pyrazolyl, oxazolyl, isoxazolyl, pyridyl, pyrimidinyl, pyrazinyl, piperidyl, piperazinyl and morpholinyl, which groups being the same as <substituent group β> in the above formula(I) and <substituent group β> being used in the following explanation of $R_5$ and $R_6$.

In the above $R_5$ and $R_6$ said aliphatic or aromatic ring substituent or said aromatic or aliphatic heterocycle may have lower alkyl; lower alkyl which is substituted by $C_3$–$C_8$ cycloalkyl or aryl; or $C_3$–$C_8$ cycloalkyl.

In the above formula: $Y_1$—W—$Y_2$—$R_p$, $R_p$ is hydrogen atom; or lower alkyl, cyclo-lower alkyl, lower alkenyl, lower alkynyl or aryl; or an aromatic heterocycle selected from the group consisting of imidazolyl, isoxazolyl, isoquinolyl, isoindolyl, indazolyl, indolyl, indolidinyl, isothiazolyl, ethylenedioxyphenyl, oxazolyl, pyridyl, pyrazyl, pyrazinyl, pyrimidinyl, pyridazinyl, pyrazolyl, quinoxalinyl, quinolyl, dihydroisoindolyl, dihydroindolyl, thionaphthenyl, naphthyridinyl, phenazinyl, benzoimidazolyl, benzoxazolyl, benzothiazolyl, benzotriazolyl, benzofuranyl, thiazolyl, thiadiazolyl, thienyl, pyrrolyl, furyl, furazanyl, triazolyl and methylenedioxyphenyl, which groups being the same as <substituent group δ> in the above formula(I) and <substituent group δ> being used in the following explanation of $R_5$ and $R_6$; or an aliphatic heterocycle selected from the group consisting of imidazolidinyl, tetrahydrofuranyl, piperazinyl, piperidyl, pyrrolidyl, pyrrolinyl, morpholino, tetrahydroquinolyl and tetrahydroisoquinolyl, which groups being the same as <substituent group ε> in the above formula(I) and <substituent group ε> being used in the following explanation of $R^5$ and $R^6$.

In the above $R_p$, said lower alkyl, said cyclo-lower alkyl, said lower alkenyl, said lower alkynyl or said aryl may have one or more substituent(s), which is/are same or different, selected from the group consisting of hydroxy, cyano, halogen atom, nitro, carboxyl, carbamoyl, formyl, lower alkanoyl, lower alkoxy, lower alkoxycarbonyl, lower alkoxycarbonyloxy, lower alkylcarbamoyl, di-lower alkylcarbamoyl, carbamoyloxy, lower alkylcarbamoyloxy, di-lower alkylcarbamoyloxy, amino, lower alkylamino, di-lower alkylamino, tri-lower alkylammonio, lower alkanoylamino, aroylamino, lower alkanoylamidino, lower alkylsulfonylamino, hydroxyimino, lower alkoxyimino, lower alkylthio, lower-alkyl sulfinyl, lower-alkyl sulfonyl and sulfamoyl, which groups being the same as <substituent group α> in the above formula(I), and <substituent group α> being used in the following explanation of $R_p$.

Also in the above $R_p$, the <substituent group δ> is preferably a group consisting of imidazolyl, isoxazolyl, isoquinolyl, isoindolyl, indolyl, isothiazolyl, oxazolyl, pyridyl, pyrazyl, pyrazolyl, quinolyl, dihydroisoindolyl, dihydroindolyl, benzoimidazolyl, benzoxazolyl, benzothiazolyl, benzofuranyl, thiazolyl, thienyl, pyrrolyl, furyl, triazolyl and methylenedioxyphenyl, which is hereinafter described as <substituent group $δ_1$>, and is more preferably a group consisting of imidazolyl, isoxazolyl, isoquinolyl, isoindolyl, indolyl, pyridyl, pyrazyl, pyrazolyl, quinolyl, dihydroisoindolyl, benzoimidazolyl, thienyl, pyrrolyl, furyl, triazolyl and methylenedioxyphenyl, which is hereinafter described as <substituent group $δ_2$>.

Furthermore, in the above $R_p$, <substituent group ε> is preferably a group consisting of piperazinyl, piperidyl, pyrrolidyl, morpholino, tetrahydroquinolyl and tetrahydroisoquinolyl, which is hereinafter described as <substituent group $ε_1$>, and is more preferably a group consisting of piperazinyl, piperidyl, pyrrolidyl, morpholino, tetrahydroquinolyl and tetrahydroisoquinolyl, which is hereinafter described as the <substituent group $ε_2$>.

Preferred example of $R_p$ is given below, that is, $R_p$ is preferably hydrogen atom; or lower alkyl, cyclo-lower alkyl or aryl; or aromatic heterocycle selected from the <substituent group $δ_1$> or aliphatic heterocycle selected from the <substituent group $ε_1$>.

More preferred example of $R_p$ is hydrogen atom; or lower alkyl, cyclo-lower alkyl or aryl; or aromatic heterocycle selected from the <substituent group $δ_2$> or aliphatic heterocycle selected from the <substituent group $ε_2$>.

Particularly preferable $R_p$ is lower alkyl or phenyl.

In the above formula: $Y_1$—W—$Y_2$—$R_p$, W is a member selected from the group consisting of a single bond, oxygen atom, sulfur atom, sulfinyl, sulfonyl, $NR_q$, $SO_2NR_q$, $N(R_q)SO_2NR_r$, $N(R_q)SO_2$, $CH(OR_q)$, $CONR_q$, $N(R_q)CO$, $N(R_q)CONR_r$, $N(R_q)COO$, $N(R_q)CSO$, $N(R_q)COS$, $C(R_q)$=$CR_r$, C≡C, CO, CS, OC(O), OC(O)$NR_q$, OC(S)$NR_q$, SC(O), SC(O)$NR_q$ or C(O)O, wherein $R_q$ and $R_r$ are each hydrogen atom, lower alkyl, aryl or aralkyl.

Among the above groups, a single bond, oxygen atom, sulfur atom, sulfonyl, $NR_{qa}$, $SO_2NR_{qa}$, $N(R_{qa})SO_2$, $CH(OR_{qa})$, $CONR_{qa}$, $N(R_{qa})CO$ or CO, wherein $R_{qa}$ is hydrogen atom or lower alkyl, is preferable; a single bond, oxygen atom or sulfonyl is more preferable; and a single bond or oxygen atom is particularly preferable.

Furthermore in the above formula: $Y_1$—W—$Y_2$—$R_p$, $Y_1$ and $Y_2$ may be the same or different and each represents a single bond or linear or branched lower alkylene, among which a single bond or methylene is preferable.

Preferred examples of $R_5$ and $R_6$ are given below.

That is, $R_5$ and $R_6$ are the same or different and are each preferably hydrogen atom;

a substituent selected from the group consisting of hydroxy, halogen atom, nitro, carboxyl, hydroxy-lower alkyl, halo-lower alkyl, lower alkoxy, lower alkoxycarbonyl, lower alkylcarbonyloxy, amino, lower alkylamino and di-lower alkylamino;

the formula: $Y_1$—W—$Y_2$—$R_p$ (wherein $R_p$ is lower alkyl or phenyl which may have a substituent, W is a single bond, oxygen atom or sulfonyl, and $Y_1$ and $Y_2$ are each the same or different and are each a single bond or lower alkylene);

or a 5- to 6-membered aliphatic heterocycle containing at least one nitrogen atom, selected from the group β, and particularly preferred example is hydrogen atom;

a substituent selected from the group consisting of hydroxy, halogen atom, nitro, carboxyl, hydroxyl-loweralkyl, halo-lower alkyl, lower alkoxy, lower alkoxycarbonyl and lower alkylcarbonyloxy;

the formula: $Y_1$—W—$Y_2$—$R_p$, (wherein $R_p$ is lower alkyl or phenyl which may have a substituent, W is a single bond or oxygen atom; $Y_1$ and $Y_2$ are the same or different and are each a single bond or methylene); or an aliphatic heterocycle selected from pyrrolidyl, piperidyl and piperazinyl.

Furthermore, in the above $R_5$ and $R_6$, <substituent group α> is preferably a group consisting of hydroxy, halogen atom, nitro, carboxyl, carbamoyl, lower alkoxy, lower alkoxycarbonyl, lower alkylcarbonyloxy, lower alkanoyl, lower alkoxy, lower alkylcarbamoyl, amino, lower alkylamino, di-lower alkylamino, lower alkanoylamino, aroylamino, lower alkylsulfonylamino, lower alkylsulfonyl and sulfamoyl, more preferably a group consisting of hydroxy, halogen atom, nitro, carboxyl, lower alkoxy, lower alkoxycarbonyl, lower alkylcarbonyloxy, carbamoyl, lower alkoxy, lower alkylcarbamoyl, amino, lower alkylamino, di-lower alkylamino, lower alkanoylamino, aroylamino, lower alkylsulfonylamino, lower alkylsulfonyl and sulfamoyl, and particularly preferably a group consisting of hydroxy, halogen atom, nitro, carboxyl, lower alkoxy, lower alkoxycarbonyl and lower alkylcarbonyloxy.

Additionally, in the above $R_5$ and $R_6$, the <substituent group β> is preferably a group consisting of pyrrolidyl, pyridyl, pyrimidinyl, piperidyl, piperazinyl, and morpholinyl, and more preferably a group consisting of pyrrolidyl, piperidyl and piperazinyl.

Also in the above $R_5$ and $R_6$, the <substituent group γ> is preferably hydroxy-lower alkyl or halo-lower alkyl.

Among the compounds of the general formula (I) according to the present invention, including a pharmaceutical acceptable salt or ester thereof, the preferred compound is:

(1) a pyrazinone derivative of the above formula (I), which is represented by the general formula (I-a):

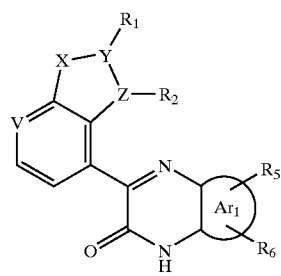

(I-a)

(wherein $Ar_1$, X, Y, Z, V, $R_1$, $R_2$, $R_5$, $R_6$, <substituent group α>, <substituent group β>, <substituent group γ>, <substituent group δ> and <substituent group ε> have each the same meaning as defined above), and a pharmaceutically acceptable salt or ester thereof, (2) the compound defined in the above (1), wherein <substituent group α> is hydroxyl, halogen atom, nitro, carboxyl, lower alkoxy, lower alkoxycarbonyl and lower alkylcarbonyloxy; <substituent group β> is pyrrolidyl, pyridyl, pyrimidinyl, piperidyl, piperazinyl and morpholinyl; and <substituent group γ> is hydroxyl-lower alkyl, and halo-lower alkyl, (3) the compound defined in the above (2), wherein $Ar_1$ is phenyl, pyridyl or pyrimidinyl, $R_5$ and $R_6$ are each the same or different and are each hydrogen atom;

a substituent selected from the group consisting of <substituent group α> and <substituent group γ>;

the formula: $Y_1-W-Y_2-R_p$ (wherein $R_p$ is lower alkyl or phenyl {said phenyl group may have one or more substituents, which are the same or different, selected from <substituent group α>}, W is a single bond, oxygen atom or sulfonyl, $Y_1$ and $Y_2$ are each the same or different and are each a single bond or lower alkylene; or a 5- to 6-membered aliphatic heterocycle containing at least one nitrogen atom, selected from <substituent group β> (said aliphatic heterocycle may have lower alkyl; lower alkyl which is substituted by $C_5$–$C_6$ cycloalkyl or phenyl; or $C_5$–$C_6$ cycloalkyl), (4) the compound defined in the above (3), wherein X is CO and Y is N, (5) the compound defined in the above (4), wherein $R_1$ is lower alkyl (said lower alkyl may have one or more substituents, which are the same or different, selected from <substituent group α>); or an aliphatic or aromatic cyclic substituent selected from the group consisting of $C_5$–$C_6$ cycloalkyl, $C_5$–$C_6$ cycloalkenyl, and phenyl (said aliphatic or aromatic ring substituent may have one or more groups selected from the group consisting of a substituent selected from <substituent group α> and/or a lower alkyl which may be substituted by one or more substituents, which are the same or different, selected from <substituent group α>), or lower alkyl substituted by said aliphatic or aromatic ring substituent; or an aromatic or aliphatic heterocycle containing at least one nitrogen selected from <substituent group β> (said aromatic or aliphatic heterocycle may have one or more substituents selected from the group consisting of a substituent of <substituent group α> and/or a lower alkyl group which may be substituted by one or more substituents, which are the same or different, selected from phenyl and <substituent group β>), or lower alkyl substituted by said aromatic or aliphatic heterocycle, (6) the compound defined in the above (5), wherein Z is N, S, or O, and V is CH, (7) the compound defined in the above (5), wherein Z is N, S, or O, and V is N, (8) the compound defined in the above (5), wherein Z is CH, V is CH, and $R_2$ is hydrogen atom, (9) the compound defined in the above (5), wherein Z is taken together with $R_2$ to form Co, and V is CH

(10) the compound defined in the above (1), wherein $Ar_1$ is phenyl or pyridyl;

X is CO; Y is N; Z is N or S; V is CH;

$R_1$ is a lower alkyl (said lower alkyl may have one or more substituents, which are the same or different, selected from <substituent group α>); or an aliphatic or aromatic ring substituent selected from the group consisting of $C_5$–$C_6$ cycloalkyl and phenyl (said aliphatic or aromatic ring substituent may have one or more substituents, which are the same or different, selected from <substituent group α> and/or lower alkyl optionally substituted by one or more substituents, which are the same or different, selected from <substituent group α>), or lower alkyl substituted by said aliphatic or aromatic ring substituent; or an aromatic or aliphatic heterocycle containing at least one nitrogen, selected from <substituent group β> (said aromatic or aliphatic heterocycle may have one or more substituents, which are the same or different, selected from the group consisting of <substituent group α> and/or and lower alkyl optionally substituted by one or more substituent, which are the same or different, selected from phenyl and <substituent group β>), or lower alkyl substituted by said aromatic or aliphatic heterocycle; and, $R_5$ and $R_6$ are each the same or different and are each hydrogen atom;

a substituent selected from the group consisting of <substituent group α> and <substituent group γ>;

the formula: $Y_1-W-Y_2-R_p$ (wherein $R_p$ is lower alkyl or phenyl (said phenyl group may have one or more substituents, which are the same or different, selected from <substituent group α>}, W is a single bond or an oxygen atom, Y₁ and Y₂ are each the same or different and are each a single bond or lower alkylene); or a 5- or 6-membered aliphatic heterocycle having at least one nitrogen atom, selected from <substituent group β> (said aliphatic heterocycle may have lower alkyl; lower alkyl which is substituted by C₅–C₆ cycloalkyl or phenyl; or C₅–C₆ cycloalkyl),

(11) the compound defined in the above (10), wherein the <substituent group α> is hydroxy, cyano, halogen atom, nitro, carboxyl, carbamoyl, lower alkanoyl, lower alkoxy, lower alkoxycarbonyl, lower alkylcarbonyloxy, lower alkylcarbamoyl, di-lower alkylcarbamoyl, carbamoyloxy, lower alkylcarbamoyloxy, amino, lower alkylamino, di-lower alkylamino, tri-lower alkylammonio, lower alkanoylamino, aroylamino, lower alkylsulfonylamino, hydroxyimino, lower alkylthio, lower alkylsulfonyl and sulfamoyl, the <substituent group β> is pyrrolyl, pyrrolidyl, thiazolyl, pyrazolyl, oxazolyl, isoxazolyl, pyridyl, pyrimidinyl, pyrazinyl, piperidyl, piperazinyl and morpholinyl, and the <substituent group γ> is hydroxy-loweralkyl, halo-lower alkyl, carbamoyl-lower alkyl, amino-lower alkyl, lower alkylamino-lower alkyl and tri-lower alkylammonio-lower alkyl,

(12) the compound defined in the above (1), wherein the pyrazinone derivative is 9-(3-oxo-3,4-dihydroquinoxalin-2-yl)-1,2,3,9b-tetrahydro-5H-pyrrolo[2,1-a]isoindol-5-one, 9-(3-oxo-6,7-dimethyl-3,4-dihydroquinoxalin-2-yl)-1,2,3,9b-tetrahydro-5H-pyrrolo[2,1-a]isoindol-5-one, 3-(2-cyclopentyl-1-oxo-2,3-dihydro-1H-isoindol-4-yl)-7-methylquinoxalin-2(1H)-one, 3-(2-cyclopentyl-3-oxo-2,3-dihydro-1,2-benzisothiazol-7-yl) quinoxalin-2(1H)-one, 3-(2-(4-hydroxycyclohexyl)-3-oxo-2,3-dihydro-1,2-benzisothiazol-7-yl)quinoxalin-2(1H)-one, 3-(2-(2,2,2-trifluoroethyl)-3-oxo-2,3-dihydro-1,2-benzisothiazol-7-yl)quinoxalin-2(1H)-one, 7-(1-benzylpyrrolidin-3-yl)-3-(2-cyclopenytyl-1-oxo-2,3-dihydro-1H-isoindol-4-yl)quinoxalin-2(1H)-one, 3-(2-cyclopentyl-3-oxo-2,3-dihydro-1,2-benzisothiazol-7-yl)pyrido[2,3-b]pyrazin-2(1H)-one, 5-hydroxy-3-[2-(2,2,2-trifluroethyl)-3-oxo-2,3-dihydro-1,2-benzisothiazol-7-yl]quinoxalin-2(1H)-one, 5-hydroxy-3-[2-(4-hydroxycyclohexyl)-3-oxo-2,3-dihydro-1,2-benzisothiazol-7-yl]quinoxalin-2(1H)-one, 3-(2-cyclopentyl-3-oxo-2,3-dihydro-1,2-benzisothiazol-7-yl]pyrido[3,4-b]pyrazin-3(4H)-one, 3-(2-cyclopentyl-3-oxo-2,3-dihydro-1,2-benzisothiazol-7-yl]pyrido[2,3-b]pyrazin-3(4H)-one, 7-(pyrrolidin-3-yl)-3-[2-(4-hydroxycyclohexyl)-3-oxo-2,3-dihydro-1,2-benzisothiazol-7-yl]quinoxalin-2(1H)-one, 3-[3-oxo-2-(2,2,2-trifluoro-1-(hydroxymethyl)ethyl)-2,3-dihydro-1,2-benzisothiazol-7-yl]quinoxalin-2(1H)-one, 3-(2-cyclopentyl-3-oxo-2,3-dihydroisothiazolo[4,5-b]pyridin-7-yl)quinoxalin-2(1H)-one or 3-(2-cyclopentyl-3-oxo-2,3-dihydro-1H-indazol-7-yl)-5-hydroxyquinoxalin-2(1H)-one, and the like.

A preferred example of a compound of the general formula (I) is a compound represented by the general formula (I-p1):

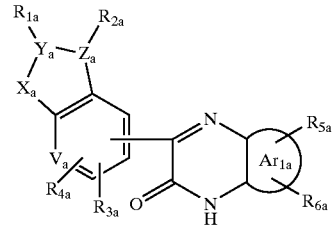

(I-p1)

[wherein Ar₁ₐ is aryl or a 5- to 6-membered aromatic heterocycle selected from the group consisting of pyridyl, pyrrolyl, pyrazolyl and thienyl, which is fused to the adjacent pyrazinone ring at the positions of 5 and 6;

Xa is CO or SO₂; Yₐ is N; Zₐ is CH, N, S or O (with the proviso that Zₐ is taken together with R₂ₐ to form N, S or O when Zₐ is not CH), Vₐ is CH or N;

R₁ₐ is a lower alkyl which may have one to three substituent(s) selected from the group consisting of hydroxy, halogen atom, carboxyl, carbamoyl, lower alkanoyl, lower alkoxy, lower alkylcarbamoyl, di-lower alkylcarbamoyl, amino, lower alkylamino, di-lower alkylamino, lower alkanoylamino, aroylamino, lower alkylsulfonylamino, lower alkylsulfonyl and sulfamoyl; or an aliphatic or aromatic ring substituent selected from the group consisting of C₃–C₈ cycloalkyl and aryl, which may have one to three substituent(s) selected from the group consisting of hydroxy, halogen atom, carboxyl, carbamoyl, lower alkanoyl, lower alkoxy, lower alkylcarbamoyl, di-lower alkylcarbamoyl, amino, lower alkylamino, di-lower alkylamino, lower alkanoylamino, aroylamino, lower alkylsulfonylamino and lower alkylsulfonyl, and lower alkyl(s) optionally substituted by the said ring substituent; or a 5- to 6-membered aliphatic heterocycle containing at least one of N, S or O, which is selected from the group consisting of pyrrolidyl, thiazolyl, imidazolyl, oxazolyl, isoxazolyl, pyridyl, pyrazinyl, piperiyl, piperazinyl and morpholinyl, or lower alkyl substituted by the said heterocycle;

R₂ₐ is hydrogen atom or a lower alkyl which may have one or two substituents selected from the group consisting of hydroxy, cyano and lower alkoxy; or R₂ₐ, together with Zₐ to which R₂ₐ binds, Yₐ and R₁ₐ, may have at least one hetero atom selected from S and O which are different from Yₐ and/or Zₐ and form a 5- or 7-membered saturated aliphatic heterocycle selected from the group consisting of

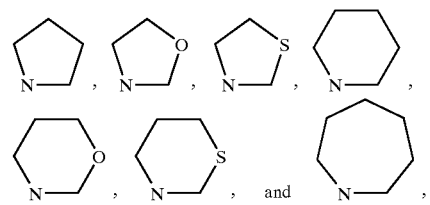

which may have one to three substituents selected from (1) a substituent selected from the group consisting of hydroxy, halogen atom, carboxyl, carbamoyl, lower alkanoyl, lower alkoxy, lower alkylcarbamoyl, di-lower alkylcarbamoyl, amino, lower alkylamino, di-lower alkylamino, lower alkanoylamino, aroylamino, lower alkylsulfonylamino and lower alkylsulfonyl, and (2) lower alkyl, (3) aryl and (4) aralkyl wherein the groups (2) to (4) may be optionally substituted by the aforesaid substituent, $R_{3a}$ and $R_{4a}$ are the same or different and are each hydrogen atom, halogen atom, hydroxy or amino; or lower alkyl which may have one to two substituents selected from the group consisting of hydroxy, halogen atom, carboxyl, carbamoyl, lower alkanoyl, hydroxyl-loweralkyl, halo-lower alkyl, amino, lower alkylamino, di-lower alkylamino, lower alkylsulfonylamino and lower alkylsulfonyl, $R_{5a}$ and $R_{6a}$ are the same or different and are each hydrogen atom, hydroxy, halogen atom, lower alkoxy, amino, lower alkylamino, di-lower alkylamino, or the formula: $Y_{1a}-W_a-Y_{2a}-R_{pa}$ {wherein $R_{pa}$ is hydrogen atom; or a lower alkyl; a cyclo-lower alkyl; an aryl; an aromatic heterocycle selected from the group consisting of imidazolyl, isoxazolyl, isoquinolyl, isoindolyl, indolyl, isothiazolyl, oxazolyl, pyridyl, pyrazyl, pyrazolyl, quinolyl, dihydroisoindolyl, dihydroindolyl, benzoimidazolyl, benzoxazolyl, benzothiazolyl, benzofuranyl, thiazolyl, thienyl, pyrrolyl, furyl, triazolyl and methylenedioxyphenyl; or an aliphatic heterocycle selected from the group consisting of piperazinyl, piperidyl, pyrrolidyl, morpholino, tetrahydroquinolyl and tetrahydroisoquinolyl, which may have one to four substituents selected from the group consisting of hydroxy, halogen atom, carbamoyl, lower alkanoyl, lower alkoxy, lower alkylcarbamoyl, amino, lower alkylamino, di-lower alkylamino, lower alkanoylamino, aroylamino, lower alkylsulfonylamino, lower alkylsulfonyl and sulfamoyl; and $W_a$ is a single bond, oxygen atom, sulfur atom, sulfonyl, $NR_{qa}$, $SO_2NR_{qa}$, $N(R_{qa})SO_2$, $CH(OR_{qa})$, $CONR_{qa}$, $N(R_{qa})CO$ or $CO$ (wherein $R_{qa}$ is hydrogen atom or lower alkyl), and $Y_{1a}$ and $Y_{2a}$ have each the same meaning as defined for $Y_1$ and $Y_2$}, with the proviso that the case where $X_a$ is CO, and $Y_a$ and $Z_a$ are concurrently CH is excluded].

The more preferred compound than the compound of the formula (I-p1) is a compound represented by the general formula (I-p2):

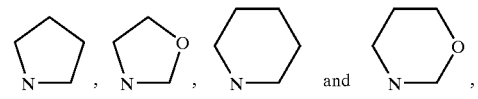
(I-p2)

[wherein $Ar_{1b}$ is aryl which is fused to the adjacent pyrazinone ring at the positions of 5 and 6, $X_b$ is CO or $SO_2$, $Y_b$ is N, $Z_b$ is CH, N, S or O (with the proviso that $Z_b$ is taken together with $R_{2b}$ to form N, S or O when $Z_b$ is not CH), $V_b$ is CH, $R_{1b}$ is a lower alkyl which may have one to three substituent(s) selected from the group consisting of hydroxy, halogen atom, carboxyl, carbamoyl, lower alkoxy, lower alkylcarbamoyl, di-lower alkylcarbamoyl, amino, lower alkylamino, di-lower alkylamino, lower alkanoylamino, lower alkylsulfonylamino, lower alkylsulfonyl and sulfamoyl; $C_3-C_8$ cycloalkyl having optionally one to three substituents selected from the group consisting of hydroxy, halogen atom, carboxyl, carbamoyl, lower alkoxy, lower alkylcarbamoyl, di-lower alkylcarbamoyl, amino, lower alkylamino, di-lower alkylamino, lower alkanoylamino, lower alkylsulfonylamino and lower alkylsulfonyl; and/or lower alkyl which may be optionally substituted by the said substituent; lower alkyl substituted by the said $C_3-C_8$ cycloalkyl; 5- or 6-membered aliphatic heterocycle having at least one of nitrogen, sulfur or oxygen atom, selected from the group consisting of pyrrolidyl, pyridyl, pyrazinyl, piperidyl, piperazinyl and morpholinyl; or lower alkyl substituted by the said heterocycle, $R_{2b}$ is hydrogen atom or a lower alkyl which may have one to two substituents selected from hydroxy, cyano and lower alkoxy, or $R_{2b}$, together with $Z_b$ to which $R_{2b}$ binds, $Y_b$, and $R_{1b}$, may have at least one hetero atom selected from S and O which are different from $Y_b$ and/or $Z_b$ and form a 5- or 6-membered saturated aliphatic heterocycle selected from the group consisting of

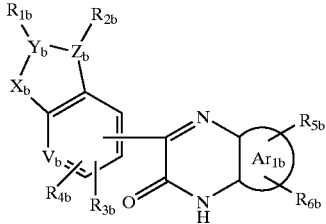

which may have one to three substituents selected from a substituent selected from the group consisting of hydroxy, halogen atom, carboxyl, carbamoyl, lower alkoxy, lower alkylcarbamoyl, di-lower alkylcarbamoyl, amino, lower alkylamino, di-lower alkylamino, lower alkanoylamino, lower alkylsulfonylamino and lower alkylsulfonyl, and lower alkyl which may be optionally substituted by the aforesaid substituent, $R_{3b}$ and $R_{4b}$ are the same or different and are each hydrogen atom or halogen atom or lower alkyl which may have one to two substituents selected from the group consisting of hydroxy, halogen atom, carboxyl, carbamoyl, hydroxyl-loweralkyl, halo-lower alkyl, amino, lower alkylamino, di-lower alkylamino, lower alkylsulfonylamino and lower alkylsulfonyl, $R_{5b}$ and $R_{6b}$ are the same or different and are each hydrogen atom, hydroxy, halogen atom, lower alkoxy, amino, lower alkylamino, di-lower alkylamino, or the formula: $Y_{1b}-W_b-Y_{2b}-R_{pb}$ {wherein $R_{pb}$ is hydrogen atom; a lower alkyl; a cyclo-lower alkyl; an aryl; an aromatic heterocycle selected from the group consisting of imidazolyl, isoxazolyl, isoquinolyl, isoindolyl, indolyl, pyridyl, pyrazyl, pyrazolyl, quinolyl, dihydroisoindolyl, benzoimidazolyl, thienyl, pyrrolyl, furyl, triazolyl and methylenedioxyphenyl; or an aliphatic heterocycle selected from the group consisting of piperazinyl, piperidyl, pyrrolidyl, morpholino, tetrahydroquinolyl and tetrahydroisoquinolyl, which may have 1 to 4 substituent(s) selected from the group consisting of hydroxy, halogen atom, carbamoyl, lower alkoxy, lower alkylcarbamoyl, amino, lower alkylamino, di-lower alkylamino, lower alkanoylamino, aroylamino, lower alkylsulfonylamino, lower alkylsulfonyl and sulfamoyl; and $W_b$ is a single bond, oxygen atom, sulfonyl, $NR_{qb}$, $SO_2NR_{qb}$, $N(R_{qb})SO_2$, $CH(OR_{qb})$, $CONR_{qb}$, $N(R_{qb})CO$ or CO (wherein $R_{qb}$ is hydrogen atom or lower alkyl), and $Y_{1b}$ and $Y_{2b}$ have each the same meaning as defined for $Y_1$ and $Y_2$), with the proviso that the case where $X_b$ is CO, and $Y_b$ and $Z_b$ are concurrently CH is excluded].

The preparation method of the compound of the general formula (I) according to the present invention is given below.

The compound of the general formula (I) can be prepared by the following Preparation Method A, Preparation Method B or Preparation Method C.

Preparation Method A

The compound represented by the general formula (II):

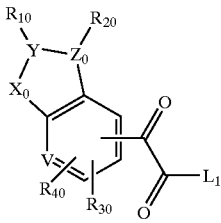

(II)

[wherein $X_0$ is CO, SO, $SO_2$ or $NCOR_0$ (in which $R_0$ is hydrogen atom, or lower alkyl, aryl or aralkyl (said lower alkyl, aryl or aralkyl may have one or more substituents, which are the same or different, selected from the group consisting of hydroxy which may be protected and carboxyl which may be protected, carbamoyl and sulfamoyl), Y is CH or N, $Z_0$ is CH, C, N, S or O (provided that when $Z_0$ is C, then $Z_0$ is taken together with $R_{20}$ to form CO, or when $Z_0$ is S or O, then $Z_0$ is taken together with $R_{20}$ to form S or O, respectively), with the proviso that the case when $X_0$ is CO and both Y and $Z_0$ are concurrently CH is excluded, V is CH or N, $L_1$ is a leaving group such as lower alkoxy (e.g. methoxy and ethoxy), $R_{10}$ is hydrogen atom; or a lower alkyl, lower alkenyl or lower alkynyl (said lower alkyl, said lower alkenyl or said lower alkynyl may have one or more substituents, which are the same or different, selected from <substituent group $\alpha_0$>); or an aliphatic or aromatic ring substituent selected from the group consisting of $C_3$–$C_8$ cycloalkyl, $C_5$–$C_8$ cycloalkenyl and aryl (said aliphatic or aromatic ring substituent may have one or more substituents selected from a substituent selected from <substituent group $\alpha_0$>, and/or a substituent selected from the group consisting of lower alkyl and lower alkenyl which may be substituted by one or more substituents, which are the same or different, selected from <substituent group $\alpha_0$>), or lower alkyl substituted by said aliphatic or aromatic ring substituent; or a 5- or 6-membered aromatic or aliphatic heterocycle which contains at least one of N, S or O, selected from <substituent group β> (said aromatic or aliphatic heterocycle may have one or more substituents selected from a substituent selected from <substituent group α>, and/or lower alkyl which may be substituted by one or more substituents, which are the same or different, selected from aryl and <substituent group β>), or lower alkyl which is substituted by said aromatic or aliphatic heterocycle, $R_{20}$ is hydrogen atom or lower alkyl (said lower alkyl may have one or more substituents, which are the same or different, selected from the group consisting of optionally protected hydroxy, cyano and lower alkoxy); or When n is 0, $R_{20}$, together with $Z_0$ to which $R_{20}$ binds, Y and $R_{10}$, may have at least one hetero atom selected from S and O, which are different from Y and/or $Z_0$ and form a 5- to 7-membered saturated aliphatic heterocycle selected from the group consisting of:

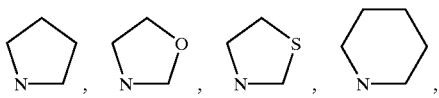

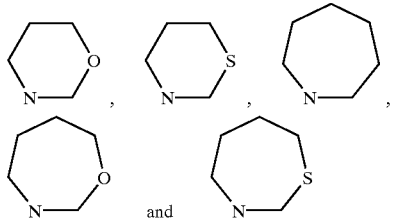

and (said saturated aliphatic heterocycle may have one or more substituents selected from the group consisting of a substituent of <substituent group α> and/or a substituent selected from lower alkyl, lower alkenyl, aryl and aralkyl {said substituent may have one or more substituents, which are the same or different, selected from <substituent group $\alpha_0$>}, provided that when $Z_0$ is C, then $Z_0$ is taken together with $R_{20}$ to form CO, or when $Z_0$ is S or O, then $Z_0$ is taken together with $R_{20}$ to form S or O, respectively.), $R_{30}$ and $R_{40}$ are each the same or different and are each hydrogen atom, halogen atom, optionally protected hydroxy, optionally protected amino acid; or lower alkyl, aryl or aralkyl (said lower alkyl, aryl and aralkyl may have one or more substituents, which are the same or different, selected from the group consisting of <substituent group $\alpha_0$> and <substituent group $\gamma_0$>, The meaning of <substituent group $\alpha_0$> and <substituent group $\gamma_0$> is given below, and <substituent group β>has the same meaning as defined in the above formula (I), <Substituent Group $\alpha_0$>:

optionally protected hydroxy, cyano, halogen atom, nitro, optionally protected carboxyl, carbamoyl, formyl, lower alkanoyl, lower alkoxy, lower alkoxycarbonyl, lower alkylcarbonyloxy, lower alkylcarbamoyl, di-lower alkylcarbamoyl, carbamoyloxy, lower alkylcarbamoyloxy, di-lower alkylcarbamoyloxy, optionally protected amino, lower alkylamino, di-lower alkylamino, tri-lower alkylammonio, lower alkanoylamino, aroylamino, lower alkanoylamidino, lower alkyl-sulfonylamino, optionally protected hydroxyimino, lower alkoxyimino, lower alkylthio, lower alkylsulfinyl, lower alkylsulfonyl and sulfamoyl.

<Substituent Group $\gamma_0$>:

optionally protected hydroxy-lower alkyl, cyano-lower alkyl, halo-lower alkyl, optionally protected carboxyl-lower alkyl, carbamoyl-lower alkyl, optionally protected amino-lower alkyl, lower alkyl-amino-lower alkyl, di(lower alkylamino)-lower alkyl, and tri(lower alkyl-ammonio)-lower alkyl]

is reacted with a compound of the general formula (III):

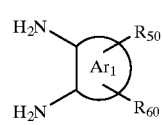

(III)

[wherein $Ar_1$ is an aryl or a 5- or 6-membered aromatic heterocycle selected from the group consisting of pyridyl, pyrimidinyl, pyrrolyl, pyrazolyl, thienyl and pyrazinyl, said aryl or heterocycle being fused at the positions of 5 and 6 of the pyrazinone ring, $R_{50}$ and $R_{60}$ are each the same or different and are each hydrogen atom;

a substituent selected from the group consisting of <substituent group $\alpha_0$> and <substituent group $\gamma_0$>;

the formula: $Y_1$—W—$Y_2$—$R_{p0}$ (wherein $R_{p0}$ is hydrogen atom; or lower alkyl, cyclo-lower alkyl lower alkenyl, lower alkynyl or aryl {said lower alkyl, cyclo lower alkyl lower alkenyl, lower alkynyl or aryl may have one or more substituents, which are the same or different, selected from <substituent group $\alpha_0$>}; or an aromatic heterocycle selected from <substituent group δ>; or an aliphatic heterocycle selected from <substituent group ε>, W is a single bond, oxygen atom, sulfur atom, sulfinyl, sulfonyl, $NR_{q0}$, $SO_2NR_{q0}$, $N(R_{q0})SO_2NR_{r0}$, $N(R_{q0})SO_2$, $CH(OR_{q0})$, $CONR_{q0}$, $N(R_{q0})CO$, $N(R_{q0})CONR_{r0}$, $NR_{q0}COO$, $N(R_{q0})CSO$, $N(R_{q0})COS$, $C(R_{q0})=CR_{r0}$, C≡C, CO, CS, OC(O), OC(O)$NR_{q0}$, OC(S)$NR_{q0}$, SC(O), SC(O)$NR_{q0}$ or C(O)O {wherein $R_{q0}$ and $R_{r0}$ are each hydrogen atom, lower alkyl, aryl or aralkyl}, $Y_1$ and $Y_2$ are each the same or different and are each a single bond or a straight or branched lower alkylene); or an aliphatic or aromatic ring substituent selected from the group consisting of $C_3$–$C_8$ cycloalkyl, $C_5$–$C_8$ cycloalkenyl and aryl (said aliphatic or aromatic ring group may have lower alkyl; lower alkyl which is substituted by $C_3$–$C_8$ cycloalkyl or aryl; or $C_3$–$C_8$ cycloalkyl), or a 5- to 6-membered aromatic or aliphatic heterocycle containing at least one of N, S or O, selected from <substituent group β> (said aromatic or aliphatic heterocycle may be substituted by lower alkyl; lower alkyl which is substituted by $C_3$–$C_8$ cycloalkyl or aryl; or $C_3$–$C_8$ cycloalkyl), and the <substituent group $\alpha_0$>, <substituent group β>, <substituent group $\gamma_0$>, <substituent group δ> and <substituent group ε> have each the same meaning as defined above] to give a compound of the general formula (IV):

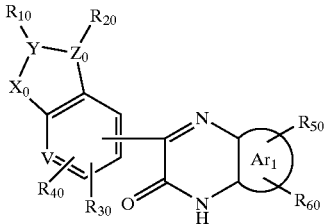

(IV)

(wherein $Ar_1$, $X_0$, Y, $Z_0$, V, $R_{10}$, $R_{20}$, $R_{30}$, $R_{40}$, $R_{50}$, $R_{60}$, <substituent group $\alpha_0$>, <substituent group β>, <substituent group $\gamma_0$>, <substituent group δ> and <substituent group ε> have each the same meaning as defined above), followed by optional removal of the protecting group to give a compound of the general formula (I):

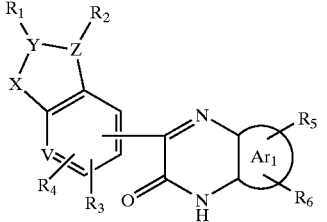

(I)

(wherein $Ar_1$, X, Y, Z, V, $R_1$, $R_2$, $R_3$, $R_4$, $R_5$, $R_6$, <substituent group α>, <substituent group β>, <substituent group γ>, <substituent group δ> and <substituent group ε> have each the same meaning as defined above).

The compound of the above formula (II) is reacted with the compound of the above formula (III) in such a manner that the compound of the formula (III) is employed in 1 to 2 moles, preferably 1 to 1.2 moles, relative to 1 mole of the compound of the formula (II). The reaction usually may be carried out in an ether such as tetrahydrofuran or dioxane, an aromatic hydrocarbon such as benzene or toluene, an alcohol such as ethanol or isopropyl alcohol or a mixture thereof, preferably in dioxane, toluene or ethanol, more preferably in toluene or ethanol.

In the above case, the reaction temperature is usually 0° C. to the boiling point of the solvent used, preferably 20 to 120° C., more preferably 120° C., though it is appropriately chosen depending on the starting materials to be used. The reaction is usually completed within 1 to 24 hours, preferably 12 to 16 hours, more preferably 15 hours, and the reaction time may be appropriately adjusted to make it longer or shorter.

In the above compound of the formula (II) and the above compound of the formula (III), when a functional group such as hydroxy, amino or carboxyl, or a substituent containing the said functional group (e.g. hydroxyl-lower alkyl, amino-lower alkyl or carboxy-lower alkyl) is present, it is preferred that the reaction is carried out after the substituent such as hydroxy, amino, carboxyl, hydroxyl-lower alkyl, amino-lower alkyl or carboxy-lower alkyl is appropriately protected with a hydroxyl-protecting group, an amino-protecting group or a carboxyl-protecting group. Such protecting group in the compound of the above formula (IV) obtained after the reaction is then optionally removed to give the compound of the above formula (I).

Examples of the hydroxyl-protecting group are lower alkylsilyl such as tert-butyldimethylsilyl or tert-butyldiphenylsilyl; lower alkoxymethyl such as methoxymethyl or 2-methoxyethoxymethyl; lower alkylsilyl-lower alkoxy such as 2-(trimethylsilyl)ethoxymethyl; aralkyl such as benzyl or p-methoxybenzyl; or acyl such as formyl or acetyl, among which tert-butyldimethylsilyl, 2-(trimethylsilyl)ethoxymethyl, acetyl or etc. is especially preferable.

Examples of the amino-protecting group are aralkyl such as benzyl, p-nitrobenzyl, p-methoxybenzyl or 3,4-dimethoxybenzyl; acyl such as formyl or acetyl; lower alkoxycarbonyl such as ethoxycarbonyl or tert-butoxycarbonyl; lower alkylsilyl-lower alkoxymethyl such as 2-(trimethylsilyl)ethoxymethyl; or aralkyloxycarbonyl such as benzyloxycarbonyl or p-nitrobenzyloxycarbonyl, among which p-nitrobenzyl, tert-butoxycarbonyl, benzyloxycarbonyl, 3,4-dimethoxybenzyl, 2-(trimethylsilyl) ethoxymethyl, or etc. is especially preferable.

Examples of the carboxyl-protecting group are lower alkyl such as methyl, ethyl or tert-butyl; or aralkyl such as benzyl or p-methoxybenzyl, among which methyl, ethyl, benzyl and the like are especially preferable.

Removal of the protecting group can be carried out according to the method described in PROTECTIVE GROUP IN ORGANIC SYNTHESIS (T. W. Greene, John Wiley & Sons, Inc, 1981) or other similar methods such as solvolysis using an acid or a base, chemical reduction using a metal complex hydride, and catalytic reduction using a palladium carbon catalyst or Raney nickel catalyst, though it depends on the kind of protecting groups and the stability of compounds used.

In the reaction between the compound of the formula (II) and the compound of the formula (III), when the compound of the above formula (I) is produced in a form of regioisomer mixtures, depending on the substitution position of $R_{50}$ and $R_{60}$ on $Ar_1$, such isomers are separated in a usual manner and optionally deprotected to yield the compound of the above formula (I) with a desirable stereo configuration. Alternatively, deprotection of the resultant isomer mixture, followed by separation in a usual manner may afford the compound of the general formula (I) with a desirable stereo configuration.

In order to regioselectively prepare the compound of the formula (IV) as a single compound from the compound of the formula (II), it is preferred to use in place of the compound of the formula (III), a compound of the general formula (III-c):

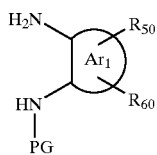

(III-c)

(wherein PG is an amino-protecting group, and $Ar_1$, $R_{50}$, $R_{60}$, <substituent group $\alpha_0$>, <substituent group $\beta$>, <substituent group $\gamma_0$>, <substituent group $\delta$> and <substituent group $\epsilon$> have each the same meaning as defined above) which can take a desirable stereo configuration and in which one of the amino groups in the 1,2-diamino moiety is protected.

The regioselective preparation of the aforementioned compound of the formula (I), when $Ar_1$ in the compound of the formula (III-c) is aryl (to be more precise, phenyl) as a typical example, is given below.

That is, a compound of the formula (II):

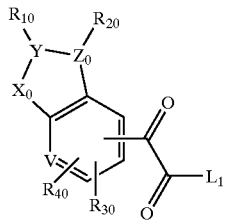

(II)

(wherein $X_0$, Y, $Z_0$, V, $L_1$, $R_{10}$, $R_{20}$, $R_{30}$, $R_{40}$, <substituent group $\alpha_0$>, <substituent group $\beta$> and <substituent group $\gamma_0$> have each the same meaning as defined above) is reacted with a compound of the general formula (III-$C_0$):

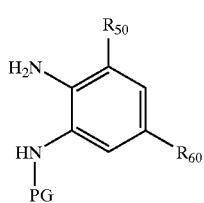

(III-$C_0$)

(wherein $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above) to obtain regioselectively a compound of the general formula (IV-$C_0$)

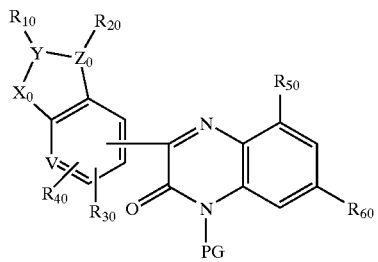

(IV-$C_0$)

(wherein $X_0$, Y, $Z_0$, V, $R_{10}$, $R_{20}$, $R_{30}$ $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above). Then the protecting group is removed from the compound of the formula (IV-$C_0$), thereby to give a compound of the formula (I-$C_0$):

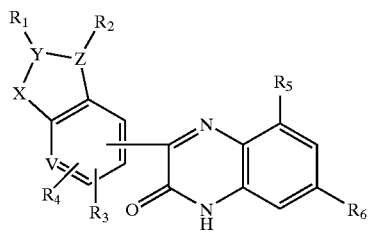

(I-$C_0$)

(wherein X, Y, Z, V, $R_1$, $R_2$, $R_3$, $R_4$, $R_5$, $R_6$, <substituent group $\alpha$>, <substituent group $\beta$>, <substituent group $\gamma$>, <substituent group $\delta$> and <substituent group $\epsilon$> have each the same meaning as defined above).

Preparation Method B

This method is to provide the desired compounds by formation of the mother skeleton, i.e., the pyrazinone ring, followed by appropriate introduction of various functional groups thereto.

A compound of the general formula (V-d):

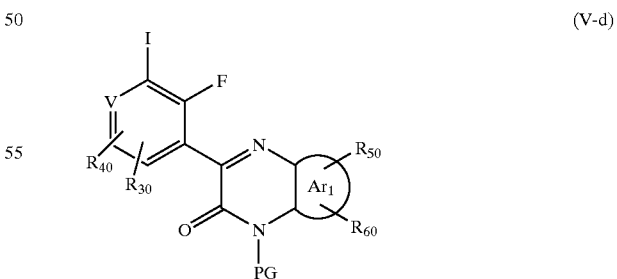

(V-d)

(wherein $Ar_1$, V, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above) can be prepared by reacting a compound of the general formula (II-d):

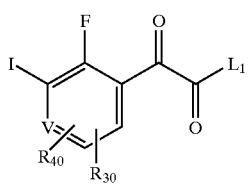

(II-d)

(wherein V, $R_{30}$, $R_{40}$, $L_1$, <substituent group $\alpha_0$> and <substituent group $\gamma_0$> have each the same meaning as defined above) with a compound of the general formula (III-c):

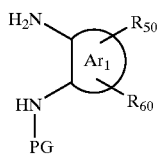

(III-c)

(wherein $Ar_1$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above).

In the above reaction, the compound of the above formula (II-d) is reacted with the compound of the formula (III-c) in such a manner that the compound of the formula (III-c) is employed in 1 to 2 moles, preferably 1 to 1.2 moles, relative to 1 mole of the compound of the formula (II-d). The reaction may usually be carried out in ethers such as tetrahydrofuran or dioxane, aromatic hydrocarbons such as benzene or toluene, alcohols such as ethanol or isopropyl alcohol or a mixture thereof, preferably in dioxane, toluene or ethanol, more preferably in toluene or ethanol.

In the above case, the reaction temperature is usually 0° C. to the boiling point of the solvent used, preferably 20 to 120° C., more preferably 120° C., though it is appropriately chosen depending on the starting materials to be used. The reaction is usually completed within 1 to 24 hours, preferably 12 to 16 hours, more preferably 15 hours, and the reaction time may be appropriately adjusted to make it longer or shorter.

Then, the compound of the formula (V-d) obtained in the above is reacted in a mixed solvent of dimethylformamide-alcohol with carbon monoxide in the presence of a palladium catalyst to be subjected to alkoxycarbonylation, whereby the compound of the general formula (V-e):

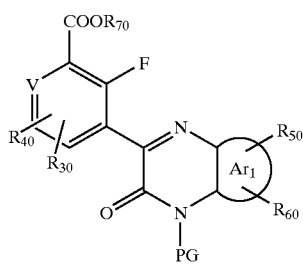

(V-e)

(wherein $R_{70}$ is lower alkyl, and $Ar_1$, V, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above) can be prepared.

The alkoxycarbonylation of the compounds of the above formula (V-d) is carried out usually in a mixed solvent of amides (e.g. dimethylformamide, dimethylacetamide, 1-methyl-2-pyrrolidinone, etc.) and alcohols (e.g. methanol, ethanol, etc.), preferably in dimethylformamide-methanol, in the presence of a palladium catalyst.

In the above reaction, the reaction temperature is usually 0° C. to the boiling point of the solvent used, preferably 40 to 120° C., more preferably 60° C., though it is appropriately chosen depending on the starting materials to be used. The reaction is complete usually within 1 to 24 hours, preferably 5 to 12 hours, more preferably within 10 hours, and the reaction time may be appropriately made longer or shorter.

Definite preparation method of the compounds of the general formula (I) having benzo- or pyrido-fused heterocycles attached to the pyrazinone is given below on each typical example.

Preparation Method B-1

The desired compounds of the general formula (I) where X is CO, Y is N and Z is S can be prepared by use of the compounds of the above formula (V-e).

That is, the compound of the above formula (V-e) is reacted with benzylmercaptan to give a sulfide derivative; the benzoic acid ester moiety in the sulfide derivative is hydrolyzed to give a compound of the general formula (VI):

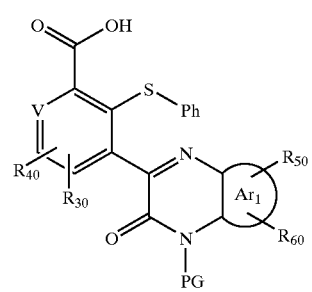

(VI)

(wherein $Ar_1$, V, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above); the compound of the above formula (VI) is condensed with an amine of the general formula (VII):

$R_{10}$—$NH_2$ (VII)

(wherein $R_{10}$ has the same meaning as defined above); and the resultant compound is subjected to oxidation to give a compound of the general formula (VIII):

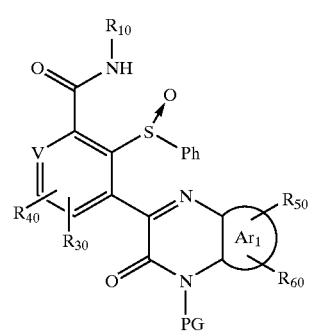

(VIII)

(wherein $Ar_1$, V, $R_{10}$, $R_{30}$, $R_{40}$, $R_{50}$, $R_{60}$, PG, <substituent group $\alpha 0$>, <substituent group $\beta$>, <substituent group $\gamma 0$>, <substituent group δ> and <substituent group ε> have each the same meaning as defined above).

In the above reaction, the reaction between the compound of the above formula (V-e) and benzylmercaptan is carried out in the presence of a base wherein the base and the thiol compound are each used in 1 to 2 moles, preferably 1 to 1.2 moles, per mole of the compound of the above formula (V-e). The reaction is usually conducted in ethers (e.g. tetrahydrofuran, dioxan), aromatic hydrocarbons (e.g. benzene, toluene), amides (e.g. dimethylformamide) or a mixture thereof, preferably in tetrahydrofuran or dimethylformamide. Examples of the base are potassium tert-butoxide and lithium hexamethyl disilazide.

In the above reaction, the reaction temperature is usually 0° C. to the boiling point of the solvent used, preferably 20 to 100° C., though it is appropriately chosen depending on the starting materials to be used. The reaction is usually complete within 1 to 24 hours, preferably 2 to 10 hours, and the reaction time may be appropriately made longer or shorter.

The condensation reaction between the carboxylic acid derivative of the above formula (VI) and the amine of the above formula (VII) is carried out in the presence of a coupling reagent wherein 1 to 2 moles, preferably 1 to 1.2 moles, of the compound of the above formula (VII) and the coupling reagent are each used, relative to one mole of the compound of the above formula (VI). The reaction is usually performed in ethers (e.g. tetrahydrofuran, dioxan), amides (e.g. dimethylformamide), halogenated solvents (e.g. dichloromethane, chloroform) or a mixture thereof, preferably in tetrahydrofuran, dimethylformamide or chloroform. The coupling reagent mentioned above includes, for example, DCC, EDCI, DMC and DPPA, and the like.

In the above reaction, the reaction temperature is usually 0° C. to the boiling point of the solvent used, preferably 0 to 40° C., more preferably room temperature, though it is appropriately chosen depending on the starting materials to be used. The reaction is usually complete within 1 to 24 hours, preferably 1 to 12 hours, and the reaction time may be appropriately made longer or shorter.

The oxidation reaction of the sulfide in the compound obtained after the condensation reaction between the compound of the above formula (VI) and the compound of the above formula (VII) is carried out using a peroxide, e.g. an oxidizing agent such as mCPBA, wherein the oxidizing agent is used in 1 to 2 moles, preferably 1 to 1.2 moles, per mole of the sulfide. The reaction may be usually conducted in a halogenated solvent such as dichloromethane or chloroform.

In the above oxidation step, the reaction temperature is usually 0° C. to the boiling point of the solvent used, preferably 0° C. to room temperature, though it is appropriately chosen depending on the starting materials to be used. The reaction is usually complete within 1 to 24 hours, preferably 2 to 12 hours, and the reaction time may be appropriately adjusted to make it longer or shorter.

Then, the compound of the above formula (VIII) is subjected to intramolecular cyclization under acidic conditions to give a compound of the general formula (IV-d)

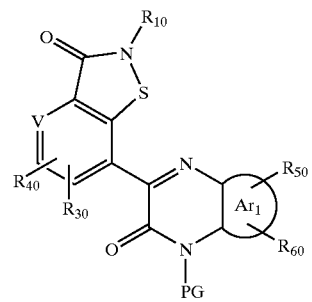

(IV-d)

(wherein $Ar_1$, V, $R_{10}$, $R_{30}$, $R_{40}$, $R_{50}$, $R_{60}$, PG, <substituent group $\alpha_0$>, <substituent group β>, <substituent group $\gamma_0$>, <substituent group δ> and <substituent group ε> have each the same meaning as defined above), followed by optional removal of the protecting group in the compound of the above formula (IV-d) to give a compound of the general formula (I-d):

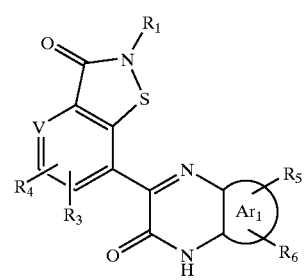

(I-d)

(wherein $Ar_1$, V, $R_1$, $R_3$, $R_4$, $R_5$, $R_6$, PG, <substituent group α>, <substituent group β>, <substituent group γ>, <substituent group δ> and <substituent group ε> have each the same meaning as defined above), i.e., a compound of the general formula (I) wherein X is CO, Y is N and Z is S.

The intramolecular cyclization reaction of the compound of the above formula (VIII) is carried out in a halogenated solvent such as chloroform, using 1 to 2 moles, preferably 1.2 moles, of trichloroacetic anhydride. The reaction time is 5 minutes to 2 hours, preferably 30 minutes, and the reaction temperature is −78° C. to room temperature.

Preparation Method B-2a

Using the compound of the above formula (V-e), there is provided a desired compound of the general formula (I) wherein X is CO, Y is N and Z is N, as shown below.

That is, the desired compound can be prepared by treating the compound of the above formula (V-e) with hydrazine, whereby the benzoic acid ester moieties are reacted with hydrazine to give a benzohydrazide; subjecting the resultant hydrazide without isolation to one pot intramolecular cyclization to give a compound of the general formula (IV-ee):

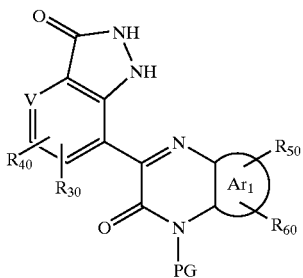

(IV-ee)

(wherein $Ar_1$, V, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above); reacting the compound of the above formula (IV-ee) with an alkyl halide derivative of the general formula (IX):

$$R_{10}\text{—}X \qquad (IX)$$

(wherein $R_{10}$ has the same meaning as defined above, and X is a bromine atom or an iodine atom) to give a compound of the general formula (IV-e):

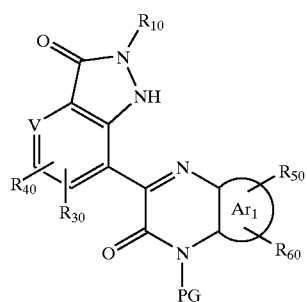

(IV-e)

(wherein $Ar_1$, V, $R_{10}$, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above); and optionally removing the protecting group of the compound of the above formula (IV-e) to give a compound of the general formula (I-e):

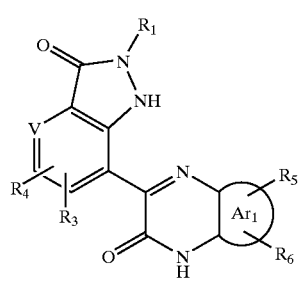

(I-e)

(wherein $Ar_1$, V, $R_1$, $R_3$, $R_4$, $R_5$, $R_6$, <substituent group $\alpha$>, <substituent group $\beta$>, <substituent group $\gamma$>, <substituent group $\delta$> and <substituent group $\epsilon$> have each the same meaning as defined above), i.e., a compound of the general formula (I) wherein X is CO, Y is N and Z is N (and $R_2$ is H).

In the above reaction, the compound of the above formula (V-e) is reacted with hydrazine, wherein hydrazine mono hydrate is employed in 1 mole to excess moles, preferably 1.2 to 3 moles, per mole of the compound of the above formula (V-e). The reaction is usually carried out in an alcohol such as methanol, ethanol or isopropyl alcohol.

In the above reaction, the reaction temperature is usually 0° C. to the boiling point of the solvent to be used, preferably 20° C. to 150° C., more preferably 120° C., though it is appropriately chosen depending on the starting materials to be used. The reaction is usually complete within 1 to 24 hours, preferably 12 to 16 hours, more preferably 15 hours, and the reaction time may be appropriately adjusted to it make longer or shorter.

The reaction between the compound of the formula (IV-ee) and the compound of the above formula (IX) is usually carried out in an alcohol (e.g. methanol, ethanol, isopropyl alcohol), wherein the compound of the above formula (IX) is used in 1 mole to excess moles, preferably 1.2 to 3 moles, relative to one mole of the compound of the formula (IV-ee).

In the above reaction, the reaction temperature is usually 80° C. to 150° C., preferably 120° C., though it is appropriately chosen depending on the starting materials to be used. The reaction is usually complete within 1 to 24 hours, preferably 1 to 5 hours, more preferably 2 hours, and the reaction time may be appropriately adjusted to make it longer or shorter.

Preparation Method B-2b

As an alternative method, the compound of the above formula (I-e) can be prepared according to the following method. That is, the benzoic acid ester moiety in the compound of the above formula (V-e) is hydrolyzed in a conventional manner to give a carboxylic acid derivative of the general formula (X):

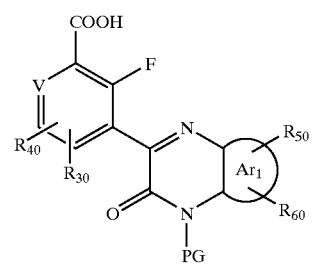

(X)

(wherein $Ar_1$, V, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above). Then, the compound of the above formula (X) is condensed with a hydrazine derivative protected by Boc, of the general formula (XXIII):

$$R_{10}\text{—NHNHBoc} \qquad (XXIII)$$

(wherein $R_{10}$ has the same meaning as defined above and Boc is tert-butyloxycarbonyl) in the presence of a coupling reagent to give an amide compound.

Then, the resultant amide compound is treated with an acid to remove the protecting group Boc and heated in an organic solvent such as dimethylformamide whereby intramolecular cyclization takes place to yield a compound of the general formula (IV-e), which is optionally deprotected to give a compound of the above formula (I-e), i.e., a compound of the general formula (I) wherein X is CO, Y is N and Z is N($R_2$=H).

The condensation reaction between the carboxylic acid derivative of the above formula (X) and the hydrazine derivative protected by Boc, of the general formula (XXIII)

is carried out in the same manner as described in Preparation Method B-1. Removal of Boc group can be conducted by treatment with an acid such as hydrochloric acid-methanol or hydrochloric acid-dioxane in a conventional manner. The subsequent intramolecular cyclization reaction is usually carried out in an amide solvent such as dimethylformamide, dimethylacetamide or N-methylpyrrolidone.

In the above reaction, the reaction temperature is usually 100° C. to 150° C., preferably 120° C., though it is appropriately chosen depending on the starting materials to be used. The reaction is usually complete within 1 to 24 hours, preferably 1 to 5 hours, more preferably 2 hours, and the reaction time may be appropriately adjusted to make it longer or shorter.

Preparation Method B-3

A desired compound of the general formula (I) wherein X is CO, Y is N and Z is O can be prepared by the following method using a compound of the above formula (V-e).

That is, the benzoic acid ester moiety in the compound of the above formula (V-e) is hydrolyzed to give a compound of the general formula (X):

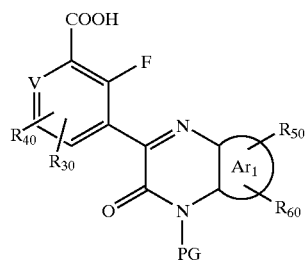
(X)

(wherein $Ar_1$, V, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above); the compound of the above formula (X) is condensed with an oxime derivative of the general formula (XI):

$R_{10}$—NHO—PG     (XI)

(wherein $R_{10}$ and PG have each the same meaning as defined above); the protecting group PG in the resultant product is removed; the deprotected product is subjected to intramolecular cyclization to give an isoxazolinone derivative of the general formula (IV-f):

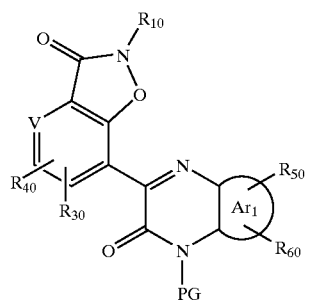
(IV-f)

(wherein $Ar_1$, V, $R_{10}$, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above); and the protecting group in the compound of the above formula (IV-f) is optionally removed to give a compound of the general formula (I-f):

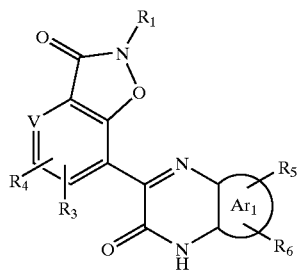
(I-f)

(wherein $Ar_1$, V, $R_1$, $R_3$, $R_4$, $R_5$, $R_6$, <substituent group $\alpha$>, <substituent group $\beta$>, <substituent group $\gamma$>, <substituent group $\delta$> and <substituent group $\epsilon$> have each the same meaning as defined above), i.e., a compound of the general formula (I) wherein X is CO, Y is N and Z is O.

The above condensation reaction is carried out in the same manner as Preparation Method B-1, and the intramolecular cyclization after deprotection is conducted in the same manner as Preparation Method B-2b.

Preparation Method B-4

By use of a compound of the above formula (X), a desired compound of the general formula (I) wherein X is CO, Y is N and Z is CH can be prepared as follows:

That is, the compound of the above formula (X) is condensed with an α-amino acid derivative of the general formula (VII-b):

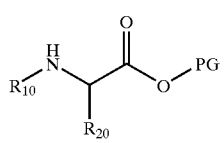
(VII-b)

(wherein $R_{10}$, $R_{20}$ and PG have each the same meaning as defined above); the resultant compound is subjected to intramolecular cyclization under basic conditions to give a compound of the general formula (VIII-b):

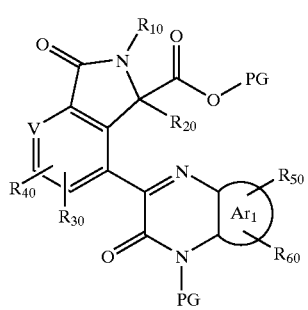
(VIII-b)

(wherein $Ar_1$, V, $R_{10}$, $R_{20}$, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above); the carboxyl-protecting group PG on the pyrrolidinone ring of the compound of the above formula (VIII-b) is deprotected under acidic or basic conditions in a conventional manner; the carboxyl group of the resultant compound is decarboxylated to give a compound of the general formula (IV-gg):

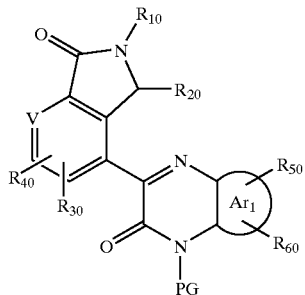

(IV-gg)

(wherein $Ar_1$, V, $R_{10}$, $R_{20}$, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above); and the protecting group in the compound of the above formula (IV-gg) is optionally removed, thereby to give a compound of the general formula (I-gg):

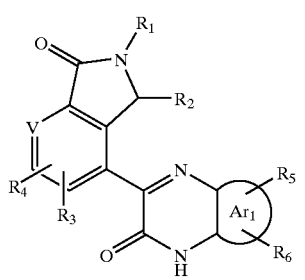

(I-gg)

(wherein $Ar_1$, V, $R_1$, $R_2$, $R_3$, $R_4$, $R_5$, $R_6$, <substituent group $\alpha$>, <substituent group $\beta$>, <substituent group $\gamma$>, <substituent group $\delta$> and <substituent group $\epsilon$> have each the same meaning as defined above), i.e., a compound of the general formula (I) wherein X is CO, Y is N and Z is CH.

Here, the condensation reaction between the compound of the above formula (X) and the compound of the above formula (VII-b) is carried out according to the method as described in Preparation Method B-1. The subsequent intramolecular cyclization is conducted by treating the amide derivative obtained above with a base (e.g. lithium bis(trimethylsilyl)amide), wherein the base is employed in 1 to 10 moles, preferably 2 to 5 moles. The reaction is usually carried out in an ether (e.g. ether, tetrahydrofuran). The reaction temperature is preferably −78° C. to room temperature. The reaction is complete usually for 5 minutes to 3 hours, preferably 30 minutes to 2 hours, and the reaction time may be made longer or shorter.

Preparation Method B-5

An amide derivative of the general formula (XXIV):

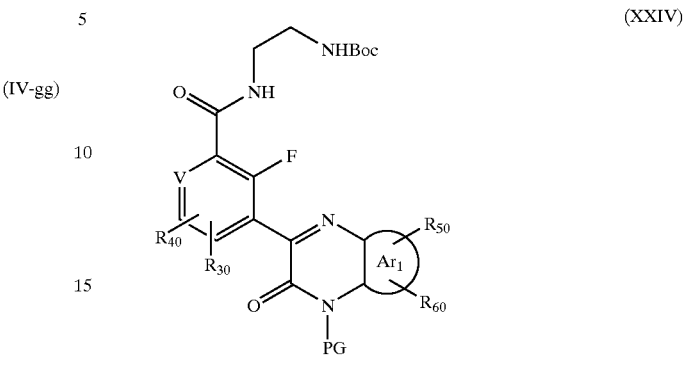

(XXIV)

(wherein $Ar_1$, V, $R_{30}$, $R_{40}$, $R_{50}$, $R_{60}$, PG, Boc, <substituent group $\alpha_0$>, <substituent group $\beta$>, <substituent group $\gamma_0$>, <substituent group $\delta$> and <substituent group $\epsilon$> have each the same meaning as defined above) can be prepared by condensing a carboxylic acid derivative of the above formula (X), obtained in Preparation Method B-2b, with an N-Boc-aminoethylamine.

Subsequently, the compound of the above formula (XXIV) is treated with an acid such as hydrochloric acid-methanol to remove Boc group; the resultant compound is subjected to intramolecular cyclization reaction under heating in a solvent such as dimethylformamide to give a 1,4-benzodiazepinone derivative; and the protecting group is optionally removed from the product to give a compound of the general formula (I-g):

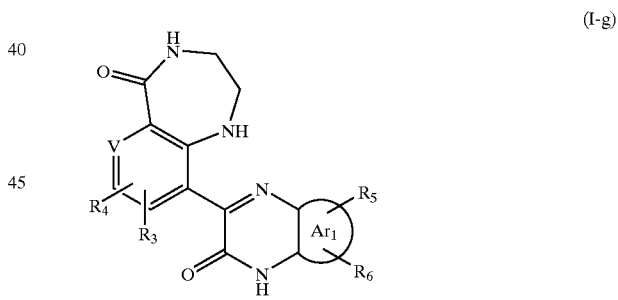

(I-g)

(wherein $Ar_1$, V, $R_3$, $R_4$, $R_5$, $R_6$, <substituent group $\alpha$>, <substituent group $\beta$>, <substituent group $\gamma$>, <substituent group $\delta$> and <substituent group $\epsilon$> have each the same meaning as defined above)

Preparation Method C

Commercially available 2,6-dibromophenol derivative is protected with SEM group (2-(trimethylsilyl)ethoxymethyl) and the resultant compound is then reacted with an organometal reagent (e.g. n-butyllithium) at low temperature in an ether (e.g. tetrahydrofuran). Then, the compound thus obtained is allowed to react with a chlorooxoacetate derivative or an oxalic acid diester derivative to give a compound of the general formula (XXV):

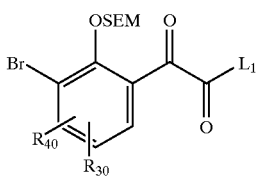

(XXV)

(wherein SEM, $L_1$, $R_{30}$, $R_{40}$, <substituent group $\alpha_0$> and <substituent group $\gamma_0$> have each the same meaning as defined above), which is then derivatized according to the method of Preparation Method B to yield a benzoic acid derivative. The ester moiety in the benzoic acid derivative is then hydrolyzed to give a salicylic acid derivative of the general formula (XXVI):

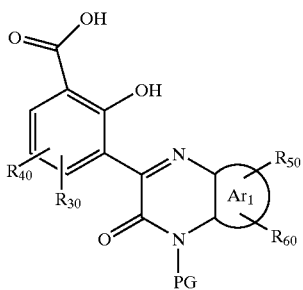

(XXVI)

(wherein $Ar_1$, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> have each the same meaning as defined above).

Then, the carboxylic acid of the above formula (XXVI) is condensed with a commercially available amino alcohol to give an amide compound, which is then subjected to intramolecular cyclization reaction through the common Mitsunobu reaction to yield a 1,4-benzoxazepine derivative. Optional deprotection of the resultant 1,4-benzoxazepine derivative can produce a compound of the general formula (I-h):

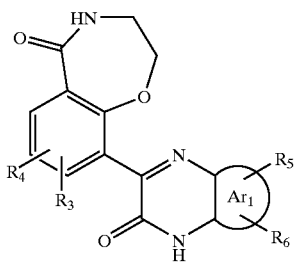

(I-h)

(wherein $Ar_1$, $R_3$, $R_4$, $R_5$, $R_6$, <substituent group $\alpha$>, <substituent group $\beta$>, <substituent group $\gamma$>, <substituent group $\delta$> and <substituent group $\epsilon$> have each the same meaning as defined above).

The compounds of the general formulae (II), (II-d), (III), (III-c), (VII), (VII-b), (IX), (XI) and (XXIII) used for the preparation of the compounds of the general formula (I) are known or can be prepared by per se known methods using known compounds.

Specific explanation of the compounds of the general formulae (II), (II-d), (III), (III-c), (VII), (VII-b), (IX), (XI) and (XXIII) is given below.

Aryloxoacetate derivatives of the general formula (II):

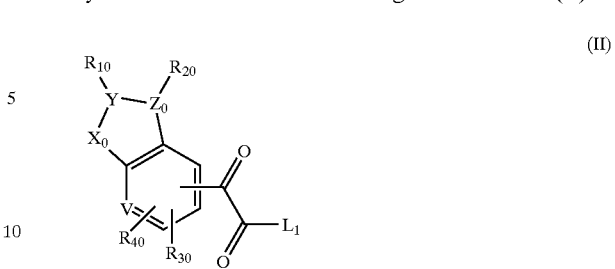

(II)

(wherein $X_0$, Y, $Z_0$, V, $R_{10}$, $R_{20}$, $R_{30}$, $R_{40}$, <substituent group $\alpha_0$>, and <substituent group $\gamma_0$> have each the same meaning as defined above) are commercially available. These compounds can also be prepared by reacting an iodo aryl derivative of the general formula (XXI):

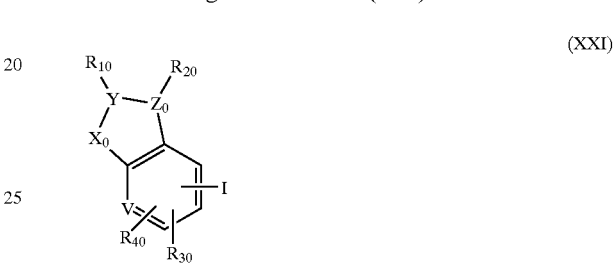

(XXI)

(wherein $X_0$, Y, $Z_0$, V, $R_{10}$, $R_{20}$, $R_{30}$, $R_{40}$, <substituent group $\alpha_0$>, <substituent group $\beta$>, <substituent group $\gamma_0$> <substituent group $\delta$> and <substituent group $\epsilon$> have each the same meaning as defined above) with an organometal reagent (e.g. n-butyl lithium) in an ether solvent (e.g. tetrahydrofuran) at low temperature and then reacting the resultant compound with a chlorooxoacetate derivative, wherein the compound of the general formula (XXI) can be prepared by reacting an arylamine obtained according to Reference Example 1, with a nitrite and then reacting the resultant diazonium salt with an iodide ion (J. March, Advanced Organic Chemistry, Wiley-Interscience Publication).

Also, the compounds of the general formula (II-d):

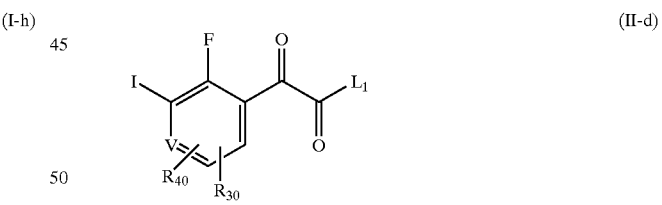

(II-d)

(wherein $L_1$, $R_{30}$, $R_{40}$, <substituent group $\alpha_0$> and <substituent group $\gamma_0$> have each the same meaning as defined above) can be prepared similarly according to the method as mentioned above. That is, such compounds can be prepared by reacting a commercially available 2-fluoro-1-iodobenzene derivative or 3-fluoro-4-iodopyridine derivative (these compounds can be prepared similarly according to the method as described in P. Rocca, Tetrahedron 49, 49–64 (1993)) with an organometal reagent (e.g. lithium diisopropylamine) in an ether solvent (e.g. tetrahydrofuran) at low temperature, followed by reacting the resultant compound with a chlorooxoacetate derivative or an oxalic acid diester.

Also, 1,2-diaminoaryl compounds of the general formula (III) are commercially available. Alternatively, such compounds can be prepared by reduction of a nitro derivative with a metal (e.g. iron) under acidic conditions (J. March, Advanced Organic Chemistry, Wiley-Interscience Publication).

Further, the compounds of the general formula (III-c) can be prepared by introducing a protecting group into one amino group of 1,2-diaminoaryl compound of the general formula (III) (T. W. Green, Protective Groups in Organic Synthesis (John Wiley & Sons)). Also, the compounds of the general formula (III-c) can be prepared by reacting a commercially available 1-fluoro-2-nitroaryl derivative with 2,3-dimethoxybenzyl-amine under heating, so that substitution reaction takes place on the fluoro group, and then reducing the nitro group of the resultant compound into an amino group, with a metal under acidic conditions.

The amines of the general formula (VII) are commercially available. Alternatively, such compounds can be prepared by reducing an oxime derived from a commercially available ketone, with lithium aluminum hydride (J. March, Advanced Organic Chemistry, (Wiley-Interscience Publication)). In the case where a reactive functional group is present on $R_{10}$ in the compounds of the general formula (VII), if necessary, optional protection with a suitable protecting group is conducted and then they are served for the reaction (T. W. Green, Protective Groups in Organic Synthesis (John Wiley & Sons)).

The compounds of the general formula (VII-b) are commercially available. Alternatively, such compounds can be prepared by reacting a commercially available tert-butyl 2-bromoacetate derivative with a commercially available amine in the presence of a base (e.g. triethylamine) (J. March, Advanced Organic Chemistry, (Wiley-Interscience Publication)).

The alkyl halides of the general formula (IX) are also commercially available.

The compounds of the general formula (XI) can be prepared by protecting a commercially available hydroxylamine derivative with t-butyldimethylsilyl chloride (T. W. Green, Protective Groups in Organic Synthesis (John Wiley & Sons)).

Hydrazine derivatives protected by Boc, of the general formula (XXIII) can be prepared by reacting a commercially available amine as a starting material with N-Boc-trichloromethyl-oxazolizine according to the method by J. Vidal, et. al (Tetrahedron Letters, 39, 8845–8848, 1998).

A 50% inhibition concentration ($IC_{50}$ value) against activity of Cdk4 and Cdk6 and cell growth on the compounds of the present invention is determined in order to specifically show the utility of the present invention.

Cdk4 Inhibition (1) Preparation of Cyclin D2-Cdk4 cDNAs of Cdk4 and its activating factor cyclin D2 were respectively introduced into an expression vector of baculovirus, to obtain recombinant baculovirus, which was then co-infected to an insect cell Sf9 to express an active complex of cyclin D2-Cdk4. The cells were recovered, dissolved and the enzymes were purified by HPLC column chromatography [The Embo Journal, 15, 7060–7069 (1996)].

(2) Determination of Cyclin D2-Cdk4 Activity

In the determination of cyclin D2-Cdk4 activity, a synthetic peptide Arg-Pro-Pro-Thr-Leu-Ser-Pro-Ile-Pro-His-Ile-Pro-Arg corresponding to the amino acid sequence No. 775–787 of RB protein was used as a substrate [The EMBO Journal, 15, 7060–7069 (1996)].

The reaction was carried out using the Kitagawa's method [Oncogene, 7, 1067–1074 (1992)] which had been partially modified. Purified cyclin D2-Cdk4, 100 μM substrate peptide, 50 μM non-labeled adenosine triphosphate (ATP) and 1 μCi [γ-33P]-labeled ATP(2000–4000 Ci/mmole) were added to a reaction buffer (referred to as R buffer) consisted of 20 mM Tris-HCl buffer (pH 7.4), 10 mM magnesium chloride, 4.5 mM 2-mercaptoethanol, 1 mM ethylene glycol bis(β-aminoethyl ether)-N,N,N',N'-tetraacetic acid (EGTA) to make total volume 21.1 μl. The mixture was incubated at 30° C. for 45 minutes, after which time 350 mM phosphate buffer (10 μl) was added to the reaction solution to stop the reaction. The peptide substrate was adsorbed on P81 paper and its radioactivity was measured by liquid scintillation counter. The [γ-33P]-labeled ATP was purchased from Daiichi Pure Chemicals.

Addition of test compounds to the reaction system was carried out in such a manner that they were dissolved in dimethyl sulfoxide and then an aliquot (1.1 μl) was added. A control group was used and prepared by addition of dimethyl sulfoxide (1.1 μl) only to the reaction system.

The compounds in the following Working Examples were chosen as typical compounds of the present invention, and their $IC_{50}$ values against cyclin D2-Cdk4 activity were determined. The results are shown in the table below.

TABLE 1

| Compound Name | $IC_{50}$ (μM) |
|---|---|
| Compound of Working Example 1 | 0.12 |
| Compound of Working Example 3 | 0.13 |
| Compound of Working Example 22 | 0.040 |
| Compound of Working Example 28 | 0.051 |
| Compound of Working Example 32 | 0.098 |
| Compound of Working Example 36 | 0.091 |
| Compound of Working Example 38 | 0.010 |
| Compound of Working Example 40 | 0.10 |
| Compound of Working Example 58 | 0.003 |
| Compound of Working Example 83 | 0.014 |
| Compound of Working Example 85 | 0.032 |
| Compound of Working Example 88 | 0.001 |
| Compound of Working Example 89 | 0.017 |
| Compound of Working Example 91 | 0.001 |
| Compound of Working Example 93 | 0.003 |
| Compound of Working Example 95 | 0.005 |
| Compound of Working Example 97 | 0.012 |
| Compound of Working Example 98 | 0.003 |
| Compound of Working Example 103 | 0.035 |
| Compound of Working Example 105 | 0.004 |
| Compound of Working Example 109 | 0.030 |
| Compound of Working Example 110 | 0.025 |
| Compound of Working Example 115 | 0.60 |

These results clearly show that the compounds of the present invention possess strong inhibitory activities against cyclin D2-Cdk4.

Inhibition of Cdk6

(1) Preparation of Cyclin D3-Cdk6

In the same manner as with cyclin D2-Cdk4, cDNAs of Cdk6 and its activating factor cyclin D3 were respectively introduced into an expression vector of baculovirus to obtain a recombinant vaculovirus, which was then co-infected to an insect cell Sf9 to express an active complex of cyclin D3-Cdk6. The cells were recovered, dissolved and the enzymes were purified on HPLC column chromatography.

(2) Determination of Cyclin D3-Cdk6 Activity

A synthetic peptide Arg-Pro-Pro-Thr-Leu-Ser-Pro-Ile-Pro-His-Ile-Pro-Arg was used as a substrate for the determination of cyclin D3-Cdk6 activity.

The reaction was carried out using the Kitagawa's method [Oncogene, 7, 1067–1074 (1992)] which had been partially modified. Purified cyclin D3-Cdk6, 100 μM substrate peptide, 50 μM non-labeled ATP and 1 μCi [γ-33P]-labeled ATP (2000–4000 Ci/mmole) were added to R buffer to make total volume 21.1 μl. The mixture was reacted at 30° C. for 45 minutes, after which time 350 mM phosphate buffer (10 μl) was added to the reaction solution to stop the reaction. The peptide substrate was adsorbed on P81 paper and its radioactivity was measured by liquid scintillation counter.

Addition of test compounds to the reaction system was carried out in such a manner that they are dissolved in dimethyl sulfoxide and then an aliquot (1.1 μl) was added. A control group was used and obtained by addition of dimethyl sulfoxide (1.1 μl) only to the reaction system.

The compound in the Working Example 3 was a typical compound of the present invention, and its $IC_{50}$ value against cyclin D2-Cdk6 activity was determined. The results are shown in the table below.

TABLE 2

| Compound Name | $IC_{50}$ (μM) |
|---|---|
| Compound of Working Example 3 | 0.088 |

The result clearly shows that the compound of the present invention possesses strong inhibitory activity against cyclin D3-Cdk6.

As mentioned above, since the compounds of the present invention possess strong inhibitory activities against Cdk4 and/or Cdk6, they are useful as inhibitors of Cdk4 and/or Cdk6, particularly inhibitors of Cdk4. Further, such inhibitors of Cdk4 and/or Cdk6 may contain a pharmaceutically acceptable carrier or a diluent.

Inhibition of Cell Growth (1) Method of Cell Culture

Clinically isolated cancer cell lines T98G and U-2OS were cultured in Dulbecco's modified Eagle's medium containing 10% fetal calf serum at 37° C. in the presence of 5% carbon dioxide under an atmosphere of saturated steam.

(2) Determination of Inhibition of Cell Growth

Inhibition of cell growth was examined by measuring the amount of formazan formation according to the method annexed in WST-8 Kit for determination of cell growth. The WST-8 Kit was purchased from Kishida Chemical Co., Ltd. Cell culture medium (50 μl each) containing $7 \times 10^2$ or $1 \times 10^3$ live cells of T98G or U-2OS was dispensed into each well of 96-well cell culture dish. The cells were pre-cultured overnight, and on the next day, a DMSO solution of the compound of Working Example 3 was made into a dilution series of solutions with DMSO. Then, the diluted solution series or DMSO only as a control of no addition of the drug were respectively added to the medium for cell culture. Finally, culture medium (50 μl each) containing the above diluted solution series of the compounds or DMSO only were added respectively to the cells which had been pre-cultured in 96-well dish, and then the cells were cultured for 3 days.

After addition of WST-kit solution (10 μl each) to each well, color reaction was carried out for 1 to 4 hours in the presence of 5% carbon dioxide under atmosphere of steam. Absorbance at 450 nm was measured using 650 nm as a control wavelength, and compared with the control group. The results on 50% inhibition of cell growth ($IC_{50}$) of compounds obtained in Working Examples 1 and 3 are shown in the following tab.

TABLE 3

| Compound Name | $IC_{50}$ (μM) T98G Cell | $IC_{50}$ (μM) U-2 OS Cell |
|---|---|---|
| Compound of Working Example 1 | 0.30 | 10.33 |
| Compound of Working Example 3 | 0.18 | 10.21 |

The compounds of the present invention are useful as anti-cancer agents for treatment of cancers, because they possess strong inhibition of cell growth. That is, pharmaceutical compositions containing pyrazinone derivatives or their pharmaceutically acceptable salts or esters of the present invention, or anti-cancer agents containing pyrazinone derivatives or their pharmaceutically acceptable salts or esters of the present invention are effective for the treatment of patients with cancers. Also, such compositions and anti-cancer agents may contain pharmaceutically acceptable carriers or diluents. In the above statement, "pharmaceutically acceptable carriers or diluents" means excipients (e.g. fat, bees wax, semi-solid or liquid polyol, natural or hydrogenated (hardened) oil); water (e.g. distilled water, especially distilled water for injection); physiological saline, alcohols (e.g. ethanol), glycerol, polyol, aqueous glucose, mannitol, vegetable oil or the like; and additives (e.g. fillers, disintegrating agents, binders, lubricants, wetting agents, stabilizers, emulsifiers, dispersing agents, preservatives, sweeteners, pigments, condiments or perfumes, thickening agents, diluting agents, buffers, solvents or solubilizers, agents for attaining storage effect, salts for adjusting osmotic pressure, coating agents or anti-oxidants).

Suitable examples of tumors against which therapeutic effect of the compounds of the present invention may be expected are, for example, human solid cancers. Examples of the human solid cancers are brain cancer, head and neck cancer, esophagus cancer, thyroid cancer, small cell cancer, non-small cell cancer, breast cancer, stomach cancer, gallbladder/bile duct cancer, hepatic cancer, pancreatic cancer, colon cancer, rectal cancer, ovarian cancer, chorioepithelioma, uterine cancer, cervical cancer, renal pelvic/ureteral cancer, bladder cancer, prostate cancer, penile cancer, testicular cancer, embryonal cancer, Wilms cancer, skin cancer, malignant melanoma, neuroblastoma, osteosarcoma, Ewing's sarcoma and soft tissue sarcoma.

When the compounds of the present invention are used as an anti-cancer agent, they may be used in the form of salts. Typical examples of such pharmaceutically acceptable salts are salts with an alkali metal such as sodium or potassium.

Such pharmaceutically acceptable salts of the present invention can be prepared by combination of common methods employed in the field of organic chemistry. More specifically, a solution of compounds of the present invention, in a free form, is neutralized with an alkali solution.

The esters of the compounds of the present invention include, for example, methyl ester and ethyl ester. These esters can be prepared by esterification of a free carboxyl group in conventional manner.

The dosage form of the compounds of the present invention can be chosen from a variety of forms, and include, for example, oral formulations (e.g. tablets, capsules, powders, granules, solutions) and sterilized liquid parenteral formulations (e.g. solutions, suspensions).

Here, the solid pharmaceutical preparations may be formulated into tablets, capsules, granules or powders, with or without a suitable additive, in a conventional manner. Such additive includes, for example, sugars (e.g. lactose, glucose); starches (e.g. corn starch, wheat, rice); fatty acids (e.g. stearic acid); inorganic salts (e.g. sodium metasilicate, magnesium aluminate, anhydrous calcium phosphate); synthetic polymers (e.g. polyvinylpyrrolidone, polyalkylene glycol); fatty acid salts (e.g. calcium stearate, magnesium stearate): alcohols (e.g. stearyl alcohol, benzyl alcohol); synthetic cellulose derivatives (e.g. methylcellulose, carboxymethyl cellulose, ethyl cellulose, hydroxypropylmethyl cellulose); and other additives commonly used (e.g. water, gelatin, talc, vegetable oil, gum arabic).

These solid preparations such as tablets, capsules, granules or powders may contain generally an effective component in 0.1 to 100 w/w %, preferably 5 to 100 w/w %, more preferably 5 to 85 w/w %, and particularly preferably 5 to 30 w/w %.

The liquid preparations such as suspensions, syrups or injections can be prepared by using a suitable additive (e.g.

water, alcohols, or vegetable-derived oils such as soy bean oil, peanut oil or sesame oil) commonly used for the production of liquid preparations.

Especially, examples of solutions or diluents for administering parenteral preparations intramuscularly, intravenously or subcutaneously are distilled water for injection, aqueous solution of lidocaine hydrochloride (for intramuscular injection), physiological saline, aqueous glucose solution, ethanol, injectable solutions via intravenous route (e.g. aqueous solutions of citric acid or sodium citrate), electrolytic solutions (e.g. intravenous drip infusion, intravenous injection) and a mixed solution thereof.

Further, these injectable preparations can take a previously-dissolved form as well as a powder with or without additives which is to be dissolved when used. These injectable solutions usually may contain an active ingredient in 0.1 to 10 w/w %, preferably 1 to 5 w/w %.

Furthermore, the solutions for oral administration such as suspensions or syrups may contain an active ingredient in 0.5 to 10 w/w %, preferably 1 to 5 w/w %.

The preferred practical dosage of the present compounds may be adjusted depending on the kind of compounds, the kind of incorporated compositions, the frequency of their application, specific affected part to be alleviated, and the conditions of patients. For example, the daily dose for adult via oral route is 10 to 500 mg, preferably 10 to 200 mg. In the case of parenteral administration, preferably intravenous injection, the daily dosage for adults is 10 to 100 mg, preferably 10 to 30 mg. Although the dosages varies depending on the administration route and the conditions of patients, it is administered in single or two to five divisions, preferably two to three divisions.

BEST MODE FOR CARRYING OUT THE PRESENT INVENTION

The present invention will be described in more detail in conjunction with Working Examples hereinafter, but it is to be construed that the present invention is not limited thereto.

Thin-layer chromatography in Working Examples and Reference Examples was carried out using silica $gel_{60}F_{254}$ (Merck) as a plate and a UV detector as a detection method. Wakogel™C-300 or C-200 (Wako Pure Chemical Industries, Ltd.) was used as silica gel for the column chromatography. High performance liquid chromatography was conducted using HP1100 series (Hewlett-Packard (HP)). Mass spectrum was measured by use of JMS-SX102A (JEOL Ltd.) or QUATTROII (Micromass Ltd.). Determination of NMR spectrum by use of deutero chloroform, deutero methanol or deutero dimethyl sulfoxide was carried out with Gemini-200 spectrometer (200 MHz; Varian Inc.), Gemini-300 spectrometer (200 MHz; Varian Inc.) or VXR-300 spectrometer (300 MHz; Varian Inc.), respectively using tetramethylsilane (TMS), methanol or dimethyl sulfoxide as an internal standard. All δ values were expressed in terms of ppm.

The abbreviations in the determination of NMR spectrum are as follows:

s: singlet d: doublet dd: double doublet t: triplet dt: double triplet q: quartet m: multiplet br: broad J: coupling constant Hz: herz $CDCl_3$: deutero chloroform DMSO-$d_6$: deutero dimethyl sulfoxide Next, compounds in Working Examples of the present invention are shown in the following table.

TABLE 4

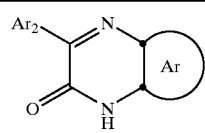

| Working Example No. | Ar2 | Ar |
|---|---|---|
| 1 | 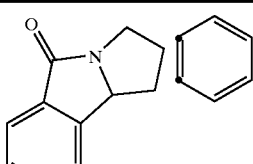 | 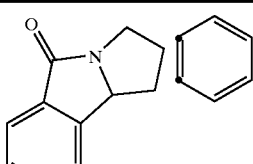 |
| 2 | " | 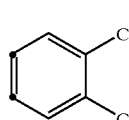 |
| 3 | " | 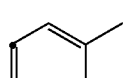 |

TABLE 4-continued

| Working Example No. | Ar2 | Ar |
|---|---|---|
| 4 | " | methyl benzoate, methyl benzoate |
| 5 | " | chlorobenzene, chlorobenzene |
| 6 | " | toluene, toluene |
| 7 | " | phenol, phenol |
| 8 | pyrrolo-isoindolone | 2-hydroxybenzoic acid, benzoic acid |
| 9 | " | nitrobenzene, nitrobenzene |
| 10 | " | pyridine, pyridine |
| 11 | " | pyridine, pyridine |

TABLE 4-continued
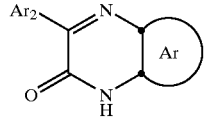
| Working Example No. | Ar2 | Ar |
|---|---|---|
| 12 | " | 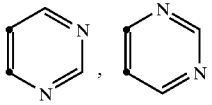 |
| 13 | " | 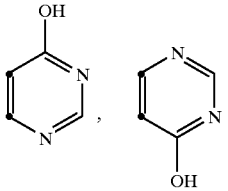 |
| 14 | 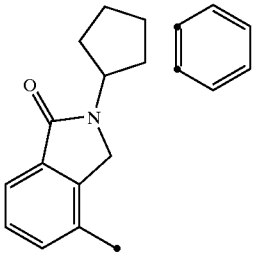 | 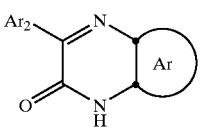 |
TABLE 5
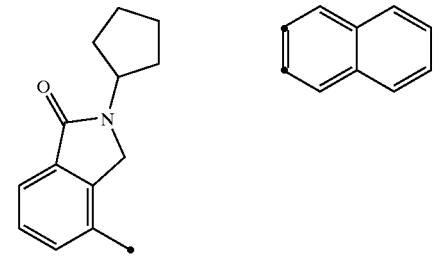
| Working Example No. | Ar2 | Ar |
|---|---|---|
| 15 | 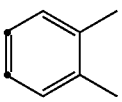 | 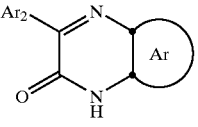 |
| 16 | " | 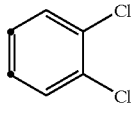 |
TABLE 5-continued
| Working Example No. | Ar2 | Ar |
|---|---|---|
| 17 | " | 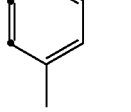 |
| 18 | " | 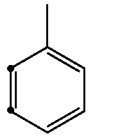 |
| 19 | " | |

TABLE 5-continued
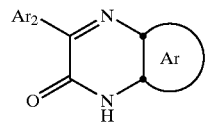
| Working Example No. | Ar2 | Ar |
|---|---|---|
| 20 | " | 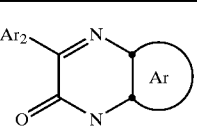 |
| 21 | " | 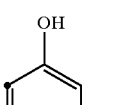 |
| 22 | 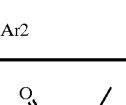 | 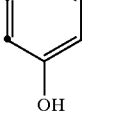 |
| 23 | 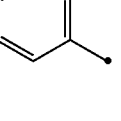 | 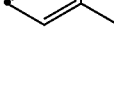 |
| 24 | 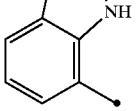 | " |
| 25 | 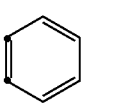 | " |
TABLE 5-continued
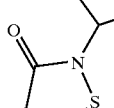
| Working Example No. | Ar2 | Ar |
|---|---|---|
| 26 |  | " |
| 27 | 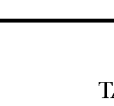 | " |
| 28 | 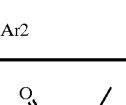 | idem |
TABLE 6
| Working Example No. | Ar2 | Ar |
|---|---|---|
| 29 | 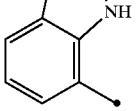 | 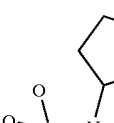 |

TABLE 6-continued
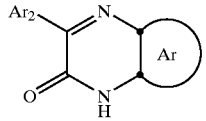
| Working Example No. | Ar2 | Ar |
|---|---|---|
| 30 | 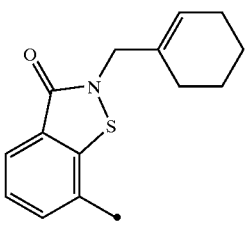 | " |
| 31 | 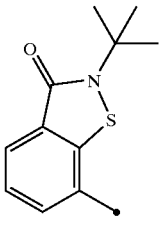 | " |
| 32 | 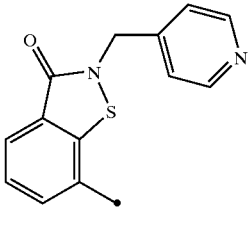 | " |
| 33 | 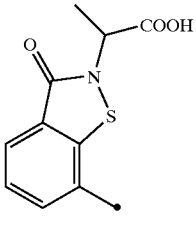 | " |
| 34 | 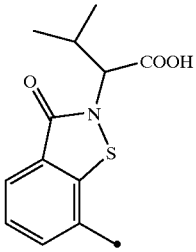 | " |
| 35 | 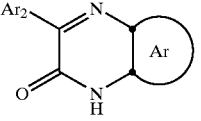 | " |
| 36 | 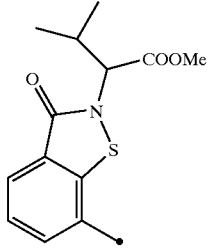 | 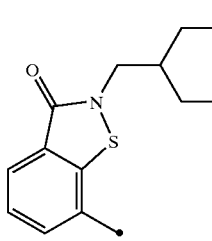 |
| 37 | 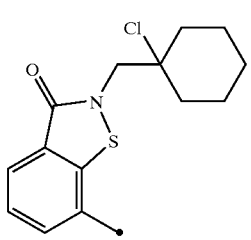 | " |
| 38 | 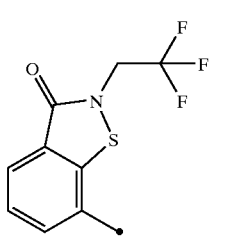 | " |
| 39 | 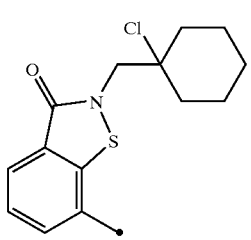 | " |

TABLE 6-continued

![structure: Ar2-C(=N)-C(=O)-NH ring fused to Ar]

| Working Example No. | Ar2 | Ar |
|---|---|---|
| 40 | 2-cyclopentyl-benzo[d]isoxazol-3(2H)-one-7-yl | " |
| 41 | 2-benzyl-isoindolin-1-one-7-yl | " |
| 42 | 2-butyl-benzo[d]isothiazol-3(2H)-one-7-yl | idem |

TABLE 7

![structure: Ar2-C(=N)-C(=O)-NH ring fused to Ar]

| Working Example No. | Ar2 | Ar |
|---|---|---|
| 43 | 2-isobutyl-isoindolin-1-one-7-yl | phenyl |
| 44 | 2-neopentyl-isoindolin-1-one-7-yl | " |
| 45 | 2-isopentyl-isoindolin-1-one-7-yl | " |
| 46 | 2-(2-methoxyethyl)-isoindolin-1-one-7-yl | " |
| 47 | 2-(butan-2-yl)-isoindolin-1-one-7-yl | " |
| 48 | 2-(pentan-2-yl)-isoindolin-1-one-7-yl | " |

TABLE 7-continued

| Working Example No. | Ar2 | Ar |
|---|---|---|
| 49 | (1-ethylpropyl-isoindolinone) | " |
| 50 | (isobutyl-isoindolinone) | (phenyl) |
| 51 | (cyclopropyl-isoindolinone) | " |
| 52 | (cyclobutyl-isoindolinone) | " |
| 53 | (propyl-isoindolinone) | " |
| 54 | (pyridin-4-ylmethyl-isoindolinone) | " |
| 55 | (2-morpholinoethyl-isoindolinone) | " |
| 56 | (1-(hydroxymethyl)cyclopentyl-benzisothiazolone) | idem |

TABLE 8

| Working Example No. | Ar2 | Ar |
|---|---|---|
| 57 | (1-(hydroxymethyl)cyclohexyl-benzisothiazolone) | (phenyl) |

TABLE 8-continued

| Working Example No. | Ar2 | Ar |
|---|---|---|
| 58 | *trans-4-hydroxycyclohexyl-isoindolinone* | " |
| 59 | *2-hydroxycyclohexyl-isoindolinone* | " |
| 60 | *N-isopropyl-benzisothiazolone* | " |
| 61 | *1-ethoxycarbonylpiperidin-4-yl-isoindolinone* | " |
| 62 | *(R)-1-benzylpyrrolidin-3-yl-isoindolinone* | " |
| 63 | *(S)-1-benzylpyrrolidin-3-yl-isoindolinone* | " |
| 64 | *methyl (S)-2-(isoindolin-2-yl)-3-methylbutanoate* | phenyl |
| 65 | *ethyl (S)-2-(isoindolin-2-yl)propanoate* | " |
| 66 | *2-cyclopentyl-3-methylisoindolinone* | " |

TABLE 8-continued
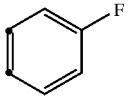
| Working Example No. | Ar2 | Ar |
|---|---|---|
| 67 | 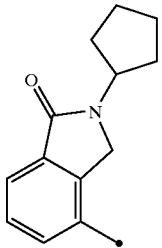 | 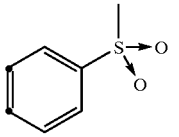 |
| 68 | " | 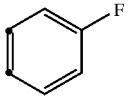 |
| 69 | " | 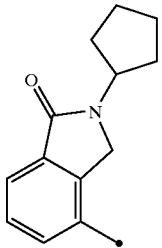 |
| 70 | " | 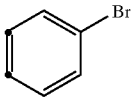 |
TABLE 9
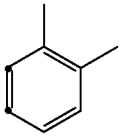
| Working Example No. | Ar2 | Ar |
|---|---|---|
| 71 | 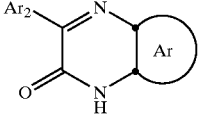 | 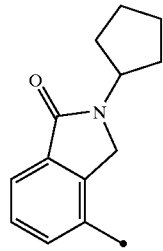 |
| 72 | " | 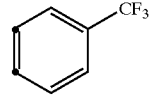 |
| 73 | " |  |

TABLE 9-continued
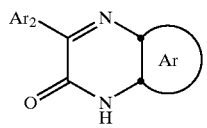
| Working Example No. | Ar2 | Ar |
|---|---|---|
| 74 | " | 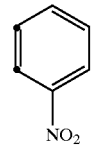 |
| 75 | " | 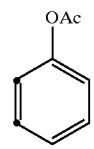 |
| 76 | " | 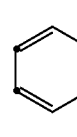 |
| 77 | " | 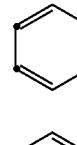 |
| 78 | 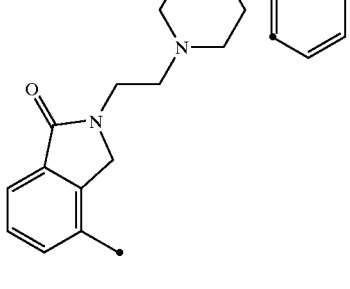 |  |
| 79 | 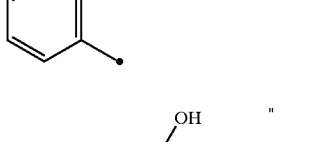 | " |
| 80 | 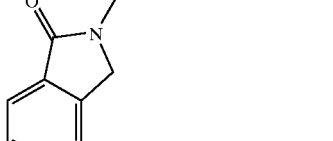 | " |

TABLE 9-continued
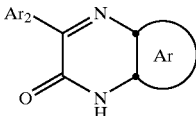
| Working Example No. | Ar2 | Ar |
|---|---|---|
| 81 | 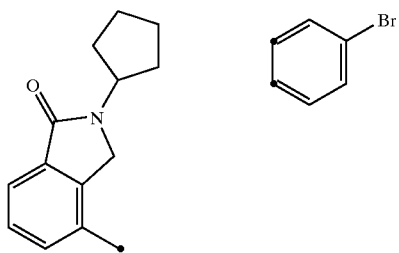 | 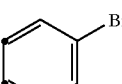 |
| 82 | " | 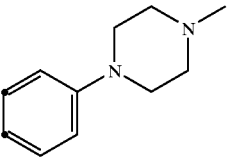 |
| 83 | " | 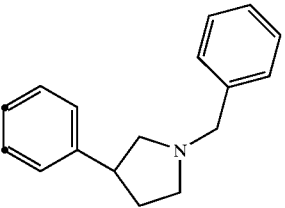 |
| 84 | " | 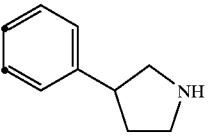 |
TABLE 10
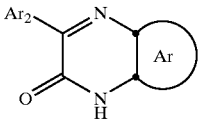
| Working Example No. | Ar2 | Ar |
|---|---|---|
| 85 | 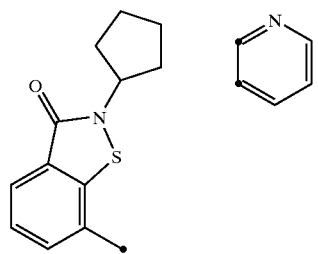 |  |

TABLE 10-continued
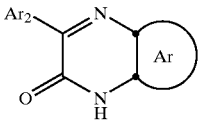
| Working Example No. | Ar2 | Ar |
|---|---|---|
| 86 | 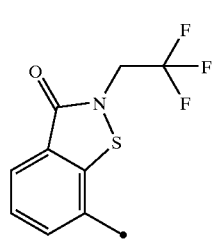 | " |
| 87 | 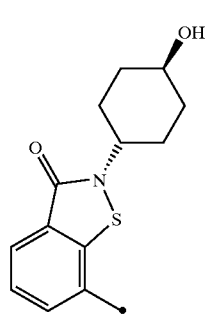 | " |
| 88 | 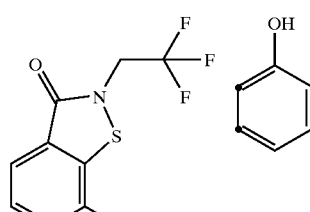 | 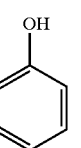 |
| 89 | " | 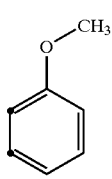 |
| 90 | " | 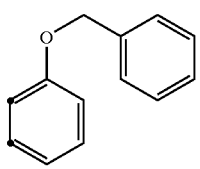 |

TABLE 10-continued
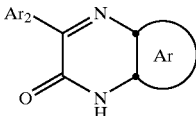
| Working Example No. | Ar2 | Ar |
|---|---|---|
| 91 | 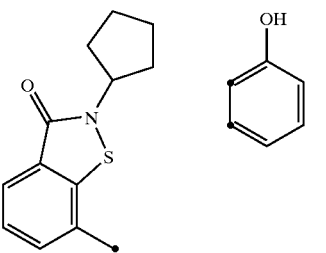 |  |
| 92 | 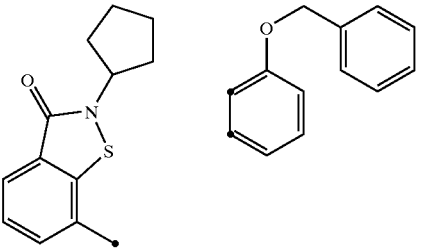 |  |
| 93 | 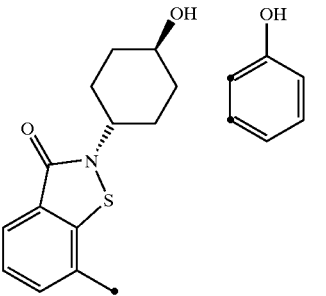 |  |
| 94 | " | 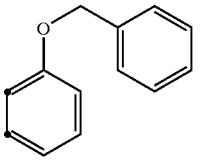 |
| 95 | 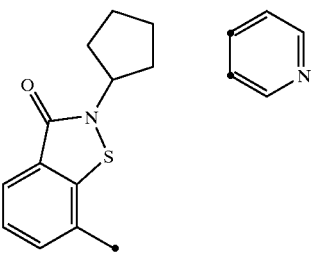 |  |
| 96 | " |  |

TABLE 10-continued
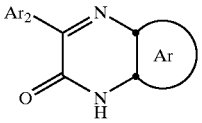
| Working Example No. | Ar2 | Ar |
|---|---|---|
| 97 | " |  |
| 98 | " | 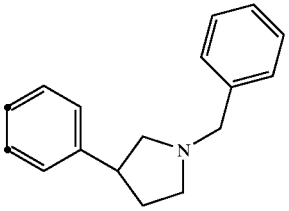 |
TABLE 11
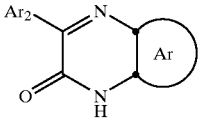
| Working Example No. | Ar2 | Ar |
|---|---|---|
| 99 | 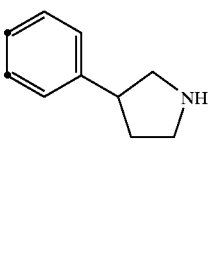 | 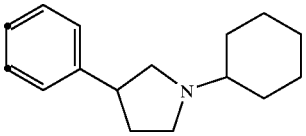 |
| 100 | " | 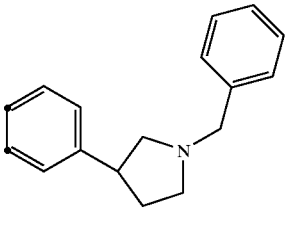 |
| 101 |  |  |

TABLE 11-continued
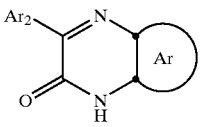
| Working Example No. | Ar2 | Ar |
|---|---|---|
| 102 | " | 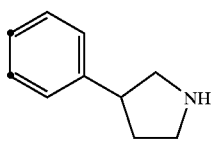 |
| 103 | " | 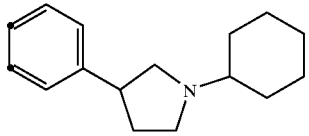 |
| 104 | 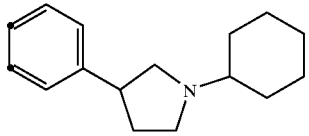 | 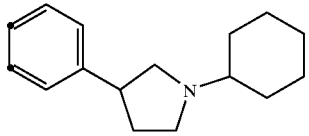 |
| 105 | " | 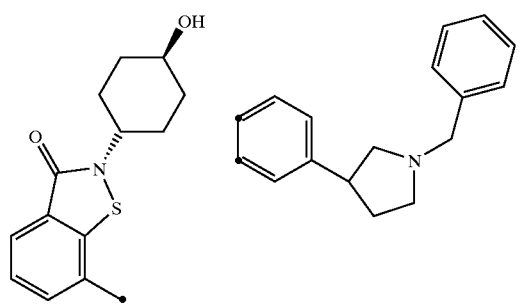 |
| 106 | 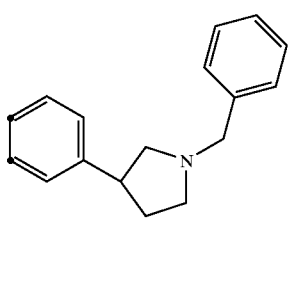 | 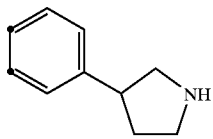 |
| 107 | 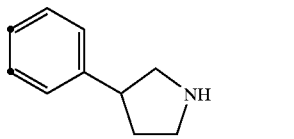 | 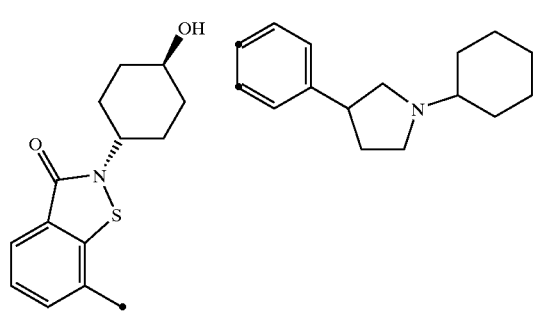 |

TABLE 11-continued
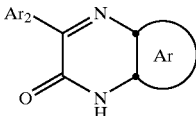
| Working Example No. | Ar2 | Ar |
|---|---|---|
| 108 | 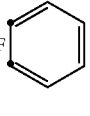 |  |
| 109 | 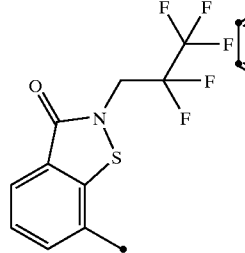 | " |
| 110 | 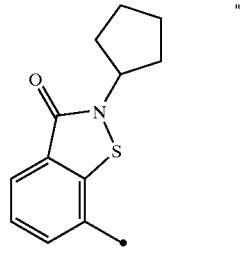 | 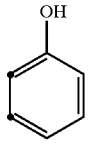 |
| 111 |  | " |
| 112 | " | 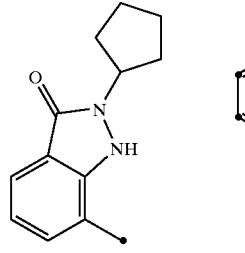 |

TABLE 12

| Working Example No. | Ar2 | Ar |
|---|---|---|
| 113 | 1-methyl-3-oxo-2,3-dihydro-1H-indazol-7-yl (with NH) | CH$_3$-phenyl |
| 114 | 1-oxo-2,3,4,5-tetrahydro-1H-benzo[b][1,4]oxazepin-9-yl | phenyl |
| 115 | 1-oxo-2,3,4,5-tetrahydro-1H-benzo[b][1,4]diazepin-9-yl | idem |

WORKING EXAMPLE 1

9-(3-oxo-3,4-dihydroquinoxaline-2-yl)-1,2,3,9b-tetrahydro-5H-pyrrolo[2,1-a]isoindol-5-one 1) 9-iodo-1,2,3,9b-tetrahydro-5H-pyrrolo[2,1-a]isoindol-5-one The compound (9-amino-1,2,3,9b-tetrahydro-5H-pyrrolo-[2,1-a]isoindol-5-one) (7.28 g, 38.7 mmol) obtained in Reference Example 1 was dissolved in a mixture of acetic acid (19.3 ml) and concentrated hydrochloric acid (7.7 ml) at 0° C. An aqueous solution (13.5 ml) of sodium nitrite (2.94 g, 42.6 mmol) was gradually added to the solution at the same temperature under stirring. After addition of water and ethyl acetate to the reaction solution at the same temperature, an aqueous solution (40 ml) of potassium iodide (7.71 g) was dropwise added thereto, and the mixture was stirred at 0° C. for an hour. Saturated aqueous Na$_2$S$_2$O$_3$ solution was added to the reaction mixture, and the mixture was stirred at room temperature for 30 minutes, then extracted with ethyl acetate. The organic layer was washed with saturated aqueous sodium hydrogen carbonate and saturated aqueous sodium chloride. After drying the extract over magnesium sulfate, the extract was filtered. The filtrate was concentrated, and the residue was purified by silica gel column chromatography (hexane-ethyl acetate, 5:1 to 1:1) to give the title compound (5.95 g) as a colorless solid.

2) Ethyl (5-oxo-1,2,3,9b-tetrahydro-5H-pyrrolo[2,1-a]isoindol-9-yl)oxoacetate

The compound (1.16 g, 3.88 mmol) obtained in 1) was dissolved in tetrahydrofuran (100 ml), and to this solution was gradually added n-butyllithium (1.5M hexane solution 3.10 ml) at −78° C. under nitrogen gas. Ethyloxalyl chloride (867 μl) in tetrahydrofuran (10 ml) was added thereto at the same temperature. After stirring the mixture for 5 minutes, the temperature of the mixture was raised to room temperature. After addition of saturated aqueous ammonium chloride at the same temperature, the mixture was extracted with ethyl acetate. The organic layer was washed with saturated aqueous sodium chloride, dried with anhydrous magnesium sulfate, filtered, and concentrated in vacuo. The residue was purified by silica gel column chromatography (hexane-ethyl acetate, 1:2) to give the title compound 212 mg as a colorless oil.

3) The compound (100 mg, 0.366 mmol) obtained in 2) and 1,2-phenylenediamine (47 mg, 0.449 mmol) was dissolved in ethanol 1 ml. The mixture was heated in a sealed tube at 100° C. for 12 hours. The reaction mixture was concentrated in vacuo, and the residue was purified by thin-layer chromatography (chloroform-methanol, 19:1) to give the title compound (35 mg) of Working Example 1 as a yellow solid.

(Preparation Method A)
$^1$H-NMR(DMSO-d$_6$)δ:1.00–1.20(1H,m),2.12–2.31(3H,m),3.22–3.64(2H,m),5.25–5.32(1H,m),6.35–8.51(7H,m),12.7(1H,s).
mass: 318(M+1)$^+$.

In the following Working Examples, compounds of Working Examples 2 to 13 were prepared according to the method in Working Example 1 (Preparation method A), but in Working Examples 4 to 13 the objective compounds were obtained as a mixture of regioisomers.

WORKING EXAMPLE 2

$^1$H-NMR(CDCl$_3$)δ:1.02–1.28(1H,m),2.10–2.35(3H,m),3.20–3.80(2H,m),5.20–5.32(1H,m),7.34(1H,s),7.45–8.48(4H,m).
mass: 387(M+1)$^+$.

WORKING EXAMPLE 3

$^1$H-NMR(CDCl$_3$)δ:1.18–1.38(1H,m),2.20–2.38(3H,m),2.39(3H,s), 2.40(3H,s),3.40–3.85(2H,m),5.36–5.65(1H,m),7.09(1H,s),7.58–8.01(4H,m),11.2(1H,s).
mass: 346(M+1)$^+$.

WORKING EXAMPLE 4 mass: 376(M+1)$^+$.

WORKING EXAMPLE 5 mass: 352(M+1)$^+$.

WORKING EXAMPLE 6 mass: 332(M+1)$^+$.

WORKING EXAMPLE 7 mass: 334(M+1)$^+$.

WORKING EXAMPLE 8 mass: 362(M+1)$^+$.

WORKING EXAMPLE 9 mass: 363(M+1)$^+$.

WORKING EXAMPLE 10 mass: 319(M+1)$^+$.

WORKING EXAMPLE 11 mass: 319(M+1)⁺.

WORKING EXAMPLE 12 mass: 320(M+1)⁺.

WORKING EXAMPLE 13 mass: 336(M+1)⁺.

WORKING EXAMPLE 14

3-(2-cyclopentyl-1-oxo-2,3-dihydro-1H-isoindol-4-yl)quinoxalin-2(1H)-one 1) 2-cyclopentyl-4-nitro-1H-isoindole-1,3(2H)-dione To a solution of 3-nitrophthalimide (3.85 g, 20.0 mmol), cyclopentanol (2.24 g, 26.0 mmol) and triphenylphosphine (6.87 g, 26.2 mmol) in tetrahydrofuran 30 ml was dropwise added 40% toluene solution (11.4 ml) of diethyl azocarboxylate under stirring in a nitrogen stream. The mixture was concentrated in vacuo, and the precipitate formed upon addition of ether was filtered off. After the filtrate was concentrated in vacuo, the residue was purified by silica gel column chromatography (hexane-ethyl acetate, 3:1) to give the title compound (3.87 g) as a colorless solid.

2) 2-cyclopentyl-3-hydroxy-4-nitroisoindolin-1-one

To a tetrahydrofuran solution (50 ml) of the compound (3.87 g, 14.9 mmol) obtained in 1) was added sodium borohydride (1.71 g, 45.2 mmol) under stirring at 0° C. After dropwise addition of methanol (25 ml), the mixture was stirred at the same temperature for an hour. The reaction solution was allowed to warm up to room temperature, and 1M potassium hydrogen sulfate was added thereto. The mixture was extracted with ethyl acetate. The organic layer was washed with saturated aqueous sodium chloride, dried over anhydrous sodium sulfate, filtered, and concentrated to give the title compound (4.67 g) as a pale yellow solid.

3) 4-amino-2-cyclopentylisoindolin-1-one

To a methanol-tetrahydrofuran (1:1) solution (200 ml) of the compound (4.65 g) obtained in 2) was added 20% palladium hydroxide on carbon catalyst (310 mg), and the mixture was stirred at room temperature for 12 hours under atmosphere of hydrogen gas. The insoluble material was filtered off through a Celite Pad and the filtrate was concentrated. The residue was purified by silica gel column chromatography (hexane-ethyl acetate, 2:1 to 1:3) to give the title compound (652 mg) as a pale yellow oil.

4) 4-iodo-2-cyclopentylisoindolin-1-one

The compound (0.620 g, 2.87 mmol) obtained in 3) was dissolved in a mixture of acetic acid (1.5 ml) and concentrated hydrochloric acid (0.6 ml) at 0° C. An aqueous solution (1.5 ml) of sodium nitrite (0.231 g, 3.35 mmol) was gradually added to the above solution at the same temperature under stirring. After addition of water and ethyl acetate, an aqueous solution (3 ml) of potassium iodide (0.584 g, 3.52 mmol) was dropwise added, and then the mixture was stirred at 0° C. for 30 minutes. To the reaction solution was added saturated aqueous $Na_2S_2O_3$ solution and the mixture was extracted with ethyl acetate. The organic layer was washed with saturated aqueous sodium hydrogen carbonate and saturated aqueous sodium chloride. After drying the extract over magnesium sulfate, the extract was filtered. The filtrate was concentrated, and the residue was purified by silica gel column chromatography (hexane-ethyl acetate, 2:1) to give the title compound (0.605 g) as a yellow oil.

5) 2-cyclopentyl-4-(tributylstannyl)isoindolin-1-one

Bis(tributyltin) (0.232 ml, 0.459 mmol) and tetrakis(triphenylphosphine)palladium(0) (17.7 mg, 0.0153 mmol) were added to a solution of the compound (100 mg, 0.306 mmol) obtained in 4) in dioxane (5 ml) under atmosphere of nitrogen gas. The mixture was stirred at 120° C. for 12 hours, and the reaction solution was filtered through a Celite Pad. The filtrate was concentrated, and purified by silica gel column chromatography (hexane-ethyl acetate, 10:1 to 1:1) to give the title compound (85 mg) as a pale yellow oil.

6) Ethyl(2-cyclopentyl-1-oxo-2,3-dihydro-1H-isoindol-4-yl)oxoacetate

Ethyloxalyl chloride (0.0137 ml, 0.122 mmol) and $Pd_2(dba)_3$ (12.7 mg, 0.0122 mmol) were added to a toluene solution (2.5 ml) of the compound obtained in 5) under atmosphere of nitrogen gas and the mixture was stirred at 70° C. for an hour. After cooling down the mixture to room temperature, the mixture was filtered through a Celite Pad and the filtrate was concentrated. The residue was dissolved in ethyl acetate, and washed with saturated aqueous potassium fluoride. The organic layer was dried over magnesium sulfate, filtered, concentrated, and purified by silica gel thin-layer chromatography (hexane-ethyl acetate, 2:1) to give the title compound (12.2 mg) as a colorless oil.

7) 1,2-phenylenediamine (5.3 mg, 0.049 mmol) was added to a solution of the compound (12.2 mg, 0.0405 mmol) obtained in 6) in ethanol (1.5 ml), and the mixture was stirred at 120° C. for 12 hours. After concentrating the mixture, the residue was purified by silica gel thin-layer chromatography (hexane-ethyl acetate, 1:1) to give the compound (8.7 mg) of Working Example 14 as a pale brown solid.

(Preparation Method A)

$^1$H-NMR(CDCl$_3$)δ:1.54–1.82(6H,m),2.01–2.16(2H,m), 4.83(2H,s),4.79–4.83(1H,m),7.31(1H,d,J=8.4 Hz),7.41(1H,t,J=7.8 Hz),7.56(1H,d,J=7.2 Hz),7.63(1H,t,J=7.8 Hz),7.91(1H,d,J=7.5 Hz),8.00(1H,d,J=7.8 Hz),8.73(1H,d,J=8.1 Hz),11.0(1H,brs).

mass: 346(M+1)⁺

In the following Working Examples, the compounds of Working Examples 15 to 21 were synthesized according to the method as in Working Example 14 (Preparation Method A).

WORKING EXAMPLE 15 mass: 396(M+1)⁺

WORKING EXAMPLE 16 mass: 374(M+1)⁺

WORKING EXAMPLE 17 mass: 414(M+1)⁺

WORKING EXAMPLE 18 mass: 360(M+1)⁺

WORKING EXAMPLE 19 mass: 360(M+1)⁺

WORKING EXAMPLE 20 mass: 362(M+1)⁺

WORKING EXAMPLE 21 mass: 362(M+1)⁺

WORKING EXAMPLE 22

3-(2-cyclopentyl-1-oxo-2,3-dihydro-1H-isoindol-4-yl)-7-methylquinoxalin-2(1H)-one 1) 1-(2,4-dimethoxybenzyl)-3-(2-cyclopentyl-1-oxo-2,3-dihydro-1H-isoindol-4-yl)-7-methylquinoxalin-2(1H)-one (2-(2,4-dimethoxybenzylamino)-4-methylaniline) (18.0 mg, 0.0664 mmol) obtained in Reference Example 2) was added to an ethanol solution (1.0 ml) of the compound (ethyl(2-cyclopentyl-1-oxo-2,3-dihydro-1H-isoindol-4-yl)-oxoacetate) (20.0 mg, 0.0661 mmol) obtained in Working Example 14-6). The mixture was stirred at 120° C. to 140° C. for 10 hours. The residue obtained by concentrating the mixture in vacuo was purified by silica gel thin-layer chromatography (hexane-ethyl acetate, 2:1) to give the title compound (25.8 mg) as a brown solid.

$^1$H-NMR(DMSO-d$_6$)δ:1.63–1.99(m,6H),1.97–2.11(m,2H),2.46(s,3H),3.76(s,3H),3.97(s,3H),4.57–4.88(m,3H),5.50(s,2H),6.35(dd,1H,J=8.3 Hz,2.2 Hz),6.52(d,1H,J=2.1 Hz),6.96(d,1H,J=8.2 Hz),7.13–7.30(m,2H),7.58(t,1H,J=8.1 Hz),7.76(d,1H,J=8.2 Hz),7.94(dd,1H,J=1.58 Hz,7.7 Hz),8.63(d,1H,J=8.0 Hz).

2) Trifluoroacetic acid (1.0 ml) was added to the compound (25.8 mg) obtained in 1). The mixture was stirred at 120° C. for 30 minutes, and concentrated in vacuo. The resulting residue was purified by silica gel thin-layer chromatography (chloroform-methanol, 20:1) to give the compound (8.6 mg) of Working Example 22 as a yellow solid. (Preparation Method A)

$^1$H-NMR(DMSO-d$_6$)δ:1.58–1.91(6H,m),2.43(3H,s),4.55–4.62(1H,m), 4.79(2H,s),7.13(1H,s),7.19(1H,d,J=7.8 Hz),7.55–7.78(3H,m),8.52(1H,t,J=7.8 Hz),12.59(1H,brs).

mass: 360(M+1)$^+$

WORKING EXAMPLE 23

3-(2-cyclopentyl-1,1-dioxide-2,3-dihydro-1,2-benzisothiazol-4-yl)quinoxalin-2(1H)-one 1) 4-nitro-2H-1,2-benzoisothiazol-3-one 1,1-dioxide was prepared according to the method described in the literature "J. Heterocyclic Chem., 23, 1253–1255 (1986)".

2) The compound of Working Example 23 was synthesized and obtained as a pale brown solid according to the method described in Working Example 14, using the compound obtained in 1).
(Preparation Method A)

$^1$H-NMR(CDCl$_3$)δ:1.58–1.95(6H,m),2.08–2.18(2H,m), 3.96(1H,m),4.76(2H,s),6.71(1H,s),7.35(1H,d,J=7.8 Hz), 7.43(1H,t,J=7.5 Hz),7.62(1H,t,J=7.8 Hz),7.68(1H,t,J=7.8 Hz),7.88(1H,d,J=6.9 Hz),7.92(1H,d,J=7.8 Hz),8.65(1H,d,J=7.8 Hz)11.96(1H,brs).

mass: 382(M+1)$^+$

WORKING EXAMPLE 24

3-(3-oxo-2,3-dihydro-1H-indazole-7-yl)quinoxalin-2(1H)-one

1) Ethyl [methoxy(methyl)amino]oxoacetate

Ethyloxalyl chloride (15.2 g, 92.7 mmol) and N,O-dimethylhydroxylamine hydrochloride (9.00 g, 92.3 mmol) were added to chloroform (180 ml) at 0° C. To the mixture was gradually added triethylamine (18.6 g, 184 mmol) under stirring. After the mixture was allowed to warm up to room temperature, the mixture was stirred for 30 minutes, and then methanol (30 ml) was added thereto. The reaction solution was concentrated in vacuo to give a residue, to which was added tetrahydrofuran. The resulting precipitates were filtered off, and the filtrate was concentrated. The residue was distilled to give the title compound (7.47 g) as a pale yellow oil.

2) Ethyl (2-fluoro-3-iodophenyl)oxoacetate n-Butyllithium (1.5M hexane solution 13.34 ml) was added to diisopropylamine (2.88 ml, 20.0 mmol) in tetrahydrofuran (40 ml) at −78° C. under atmosphere of nitrogen gas while stirring. The temperature of the mixture was raised to 0° C., and then cooled to −78° C. 1-Fluoro-2-iodobenzene (2.34 ml, 20.0 mmol) was gradually added to the mixture under stirring, and the compound (3.22 g, 20.0 mmol) obtained in 1) in tetrahydrofuran (40 ml) was added dropwise thereto. The mixture was stirred for an hour. After addition of acetic acid and saturated aqueous ammonium chloride, the mixture was extracted with ethyl acetate. The organic layer was washed with saturated aqueous sodium chloride, dried over magnesium sulfate, filtered, and concentrated. The residue was purified by silica gel column chromatography (hexane-ethyl acetate, 20:1 to 4:1) to give the title compound (2.00 g) as a colorless oil.

3) 3-(2-fluoro-3-iodophenyl)quinoxalin-2(1H)-one

The compound (1010 mg, 3.00 mmol) obtained in 2) and 1,2-phenylenediamine (389 mg, 3.60 mmol) were dissolved in ethanol (15 ml). The solution was heated in a sealed tube at 120° C. for 15 hours. The reaction solution was cooled to 0° C., and the precipitate was removed by filtration and washed with ethanol. The filtrate was concentrated in vacuo to give the title compound (922 mg) as a colorless solid.

4) Methyl 2-fluoro-3-(3-oxo-3,4-dihydroquinoxalin-2-yl)benzoate

Sodium hydrogen carbonate (275 mg, 3.27 mmol) was added to the compound (400 mg) obtained in 3) in a mixture of dimethylformamide (20 ml) and methanol (8 ml) under nitrogen gas. After adding palladium acetate (II) (49 mg, 0.218 mmol) and 1,1-bis(diphenylphosphino)ferrocene (DPPF) (121 mg, 0.218 mmol) to the reaction mixture at the room temperature in a stream of nitrogen, the atmosphere in the system was substituted for carbon monoxide. The reaction solution was stirred at 70° C. for 17 hours, and then cooled to room temperature. The reaction solution was filtered through a Celite Pad. The filtrate was concentrated to give a crude product, which was purified by silica gel column chromatography (hexane-ethyl acetate, 5:1 to 2:1) to give the title compound (87 mg) as a colorless solid.

5) The compound (87 mg) obtained in 4) and hydrazine monohydrate (0.5 ml) were added to methanol (2 ml). The mixture was stirred in a sealed tube at 150° C. for 15 hours. After cooling the reaction mixture to room temperature, the resulting precipitates were collected by filtration, and washed with methanol to give the compound (22 mg) of Working Example 24 as a yellow solid.
(Preparation Method B-2a)

$^1$H-NMR(DMSO-d$_6$)δ:7.10–7.19(1H,m),7.30–7.41(2H,m),7.50–7.60 (1H,m),7.85(1H,d,J=7.8 Hz),8.41(1H,d,J=7.8 Hz),9.19(1H,d,J=7.8 Hz),10.8(1H,bs),11.9(1H,s).

mass: 279(M+1)$^+$

WORKING EXAMPLE 25

3-(2-(2-cyclohexenyl)-3-oxo-2,3-dihydro-1H-indazol-7-yl)quinoxaline-2(1H)-one

The compound (3-(3-oxo-2,3-dihydro-1H-indazol-7-yl)-quinoxalin-2(1H)-one) (10 mg) obtained in Working Example 24 and 3-bromocyclohexene (30 ml) were added to dimethylformamide (1.0 ml). The mixture was stirred in a sealed tube at 150° C. for 2 hours. After cooling the mixture to room temperature, the mixture was concentrated to give a residue, which was purified by thin-layer silica gel chromatography (chloroform-methanol, 9:1) to give the compound (3.3 mg) of Working Example 25 as a yellow solid. (Preparation Method B-2a)

$^1$H-NMR(CDCl$_3$)δ:1.70–2.38(6H,m),5.28–5.38(1H,m) 5.80–5.90(1H,m),6.23–6.35(1H,m),7.25–7.62(4H,m),7.77 (1H,d,J=7.8 Hz),8.08 (1H,d,J=7.8 Hz),9.20(1H,d,J=7.8 Hz), 9.79(1H,s),10.9(1H,bs).

mass: 359(M+1)$^+$

The following compounds of Working Example 26 and 27 were produced by the method similar to Working Example 25 (Preparation method B-2a).

WORKING EXAMPLE 26

$^1$H-NMR(DMSO-d$_6$)δ:3.50(3H,s),7.20–7.61(4H,m),7.82 (1H,d,J=7.7 Hz),8.21(1H,d,J=7.9 Hz),9.12(1H,d,J=7.9 Hz), 10.6(1H,bs),12.7(1H,bs).

mass: 293(M+1)$^+$

WORKING EXAMPLE 27

$^1$H-NMR(DMSO-d$_6$)δ:5.21(2H,s),7.20–7.41(8H,m), 7.56–7.61(1H,m),7.89(1H,d,J=7.8 Hz),8.10(1H,d,J=7.8 Hz),9.10(1H,d,J=7.8 Hz),10.6(1H,s),12.6(1H,bs).

mass: 369(M+1)$^+$

WORKING EXAMPLE 28

3-(2-cyclopentyl-3-oxo-2,3-dihydro-1,2-benzisotiazol-7-yl)quinoxalin-2(1H)-one 1) 3-(2-fluoro-3-iodophenyl)-1-[(2-(trimethylsilyl)-ethoxymethyl)]quinoxalin-2(1H)-one Sodium hydride 8.0 mg(60%, 0.266 mmol) was added to the compound (3-(2-fluoro-3-iodophenyl)quinoxalin-2(1H)-one) (50 mg, 0.137 mmol) obtained in Working Example 24-3) and 2-trimethylsilylethoxymethyl chloride (48 ml, 0.274 mmol) in tetrahydrofuran (4 ml) at 0° C. The mixture was allowed to warm up to room temperature, and stirred for 2 hours. The reaction solution was concentrated and purified by thin-layer silica gel chromatography (hexane-ethyl acetate, 10:1) to give the title compound (68 mg) as a colorless oil.

2) Methyl 2-fluoro-3-[3-oxo-4-(2-(trimethylsilyl)-ethoxymethyl)-3,4-dihydroquinoxalin-2-yl]benzoate Sodium hydrogen carbonate (34 mg, 0.411 mmol) was added to the compound (70 mg, 0.137 mmol) obtained in 1) in a mixture of dimethylformamide (0.7 ml) and methanol (0.7 ml) under nitrogen gas. After addition of palladium (II) acetate (6.0 mg, 0.027 mmol) and DPPF (15 mg, 0.027 mmol) to the reaction solution at room temperature under a nitrogen atmosphere, the reaction system was substituted for carbon monoxide. Then, the mixture was stirred at 70° C. for 2 hours, cooled to room temperature, and concentrated in vacuo to give a crude material. The crude product was purified by thin-layer silica gel chromatography (hexane-ethyl acetate, 1:1) to give the title compound (49 mg) as a colorless oil.

3)Methyl 2-benzylthio-3-[3-oxo-4-(2-(trimethylsilyl)-ethoxymethyl)-3,4-dihydroquinoxalin-2-yl]benzoate Benzylmercaptan (142 μl, 1.21 mmol) was dissolved in dimethylformamide (3 ml), and to the solution was added potassium t-butoxide (136 mg, 1.21 mmol) at room temperature. The mixture was stirred for 5 minutes, and the compound (259 mg, 0.604 mmol), obtained in 2), in dimethylformamide (1 ml) was added thereto. The mixture was stirred at 100° C. for 2 hours, cooled to room temperature, and concentrated in vacuo. The residue was purified by thin-layer silica gel chromatography to give the title compound (114 mg) as a colorless oil.

4)2-benzylthio-3-[3-oxo-4-(2-(trimethylsilyl) ethoxymethyl)-3,4-dihydroquinoxalin-2-yl]-N-cyclopentylbenzamide 1-(3-Dimethylaminopropyl)-3-ethylcarbodiimide hydrochloride (EDCI) (121 mg, 0.630 mmol) was added to the carboxylic acid derivatives (109 mg, 0.210 mmol) prepared by hydrolyzing the compound obtained in 3) by the common method, cyclopentylamine (63 μl, 0.630 mmol) and 4-dimethylaminopyridine (DMAP) (77 mg, 0.630 mmol) in chloroform (1 ml). The mixture was stirred at room temperature for 2 days, and then concentrated. The residue was purified by thin-layer silica gel chromatography (hexane-ethyl acetate, 1:2) to give the title compound (97 mg) as a pale yellow oil.

5) 2-benzylsulfinyl-3-[3-oxo-4-(2-(trimethylsilyl) ethoxymethyl)-3,4-dihydroquinoxalin-2-yl]-N-cyclopentylbenzamide m-Chloroperoxybenzoic acid (MCPBA) (29 mg, 0.166 mmol) was added to the compound (97 mg, 0.166 mmol) obtained in 4) in chloroform (3 ml). The mixture was stirred for 1.5 hours, and concentrated. The residue was purified by thin-layer silica gel chromatography (hexane-ethyl acetate, 1:2) to give the title compound (85 mg) as a pale yellow oil.

6)3-(2-cyclopentyl-3-oxo-2,3-dihydro-1,2-benzisothiazol-7-yl)-1-[2-(trimethylsilyl) ethoxymethyl]-quinoxalin-2(1H)-one Trichloroacetic anhydride (17 μl, 0.091 mmol) was added to the compound (50 mg, 0.083 mmol) obtained in 5) in chloroform (2 ml) at −78° C. After stirring the mixture for 5 minutes, the mixture was warmed to room temperature, and concentrated. The residue was purified by thin-layer silica gel chromatography (hexane-ethyl acetate, 1:2) to give the title compound (35 mg) as a yellow oil.

7) 4N HCl-dioxane was added to the compound (20 mg, 0.041 mmol) obtained in 6), and the mixture was stirred at 100° C. for an hour. After cooling the mixture to room temperature, the mixture was concentrated in vacuo. The residue was purified by thin-layer silica gel chromatography (chloroform-methanol 19:1) to give the compound 11 mg of Working Example 28 as a yellow solid.
(Preparation Method B-1)

$^1$H-NMR(DMSO-d$_6$)δ:1.60–2.20(8H,m),4.78–4.90(1H, m),7.38–7.44(2H,m),7.55–7.70(2H,m),8.00–8.10(2H,m), 9.58(1H,dd,J=7.8 Hz,1.1Hz),12.9(1H,bs).

mass: 364(M+1)$^+$

The following compounds of Working Examples 29 to 39 were prepared according to the method as described in Working Example 28 (Preparation method B-1).

WORKING EXAMPLE 29 mass: 338(M+1)$^+$

WORKING EXAMPLE 30 mass: 390(M+1)$^+$

WORKING EXAMPLE 31 mass: 352(M+1)⁺

WORKING EXAMPLE 32 mass: 387(M+1)⁺

WORKING EXAMPLE 33 mass: 368(M+1)⁺

WORKING EXAMPLE 34 mass: 396(M+1)⁺

WORKING EXAMPLE 35 mass: 410(M+1)⁺

WORKING EXAMPLE 36 mass: 393(M+1)⁺

WORKING EXAMPLE 37 mass: 426(M+1)⁺

WORKING EXAMPLE 38 mass: 378(M+1)⁺

WORKING EXAMPLE 39 mass: 366(M+1)⁺

WORKING EXAMPLE 40

3-(2-cyclopentyl-3-oxo-2,3-dihydro-1,2-benzisoxazol-7-yl)quinoxalin-2(1H)-one

1) N-cyclopentyl-O-tert-butyldimethylsilylhydroxylamine

Imidazole (882 mg) and tert-butylmethylsilyl chloride (903 mg) were added to N-cyclopentylhydroxylamine (650 mg, 6.43 mmol) in dimethylformamide (10 ml). The mixture was stirred at room temperature for 3 hours. After diluting the mixture with ethyl acetate and hexane, the organic layer was washed with water and saturated aqueous sodium chloride. The organic layer was dried over magnesium sulfate, filtered, and concentrated in vacuo. The residue was purified by silica gel chromatography (hexane-ethyl acetate, 20:1 to 10:1) to give the title compound (722 mg) as a colorless oil.

2) 2-fluoro-3-[3-oxo-4-(2-(trimethylsilyl)ethoxymethyl)-3,4-dihydroquinoxalin-2-yl]benzoic Acid 5N Sodium hydroxide (0.50 ml) was added to the compound (methyl 2-fluoro-3-[3-oxo-4-(2-(trimethylsilyl)ethoxymethyl)-3,4-dihydroquinoxaline-2-yl]benzoate) (283 mg) obtained in Working Example 28-2) in methanol (2 ml). The mixture was stirred at room temperature for 2 hours. After adding the mixture to 5N hydrochloric acid, the mixture was extracted with chloroform. The organic layer was dried over magnesium sulfate, filtered, and concentrated in vacuo to give the title compound (285 mg) as a crude material, which was served in the subsequent reaction without purification.

3) 2-fluoro-3-[3-oxo-4-(2-(trimethylsilyl)ethoxymethyl)-3,4-dihydroquinoxalin-2-yl]-N-cyclopentyl-O-tert-butyldimethylsilylbenzohydroxamide Triethylamine (300 μl) and the compound (176 mg, 0.817 mmol) obtained in 1) were added to a chloroform solution of the compound (283 mg, 0.688 mmol) obtained in 2). To the mixture was added 2-chloro-1,3-dimethylimidazolinium chloride (191 mg) while stirring. The mixture was stirred at room temperature for 12 hours, and diluted with chloroform. The organic layer was washed with 1N hydrochloric acid and aqueous sodium hydrogen carbonate. The solution was dried over magnesium sulfate, filtered, and concentrated in vacuo. The residue was purified by silica gel chromatography (hexane-ethyl acetate, 4:1) to give the title compound (234 mg) as a colorless oil.

4) 2-fluoro-3-[3-oxo-4-(2-(trimethylsilyl)ethoxymethyl)-3,4-dihydroquinoxalin-2-yl]-N-cyclopentylbenzo-hydroxamide 1.0M Tetrahydrofuran solution (0.50 ml) of tetrabutylammonium fluoride (TBAF) was added to the compound (230 mg) obtained in 3) in tetrahydrofuran (5 ml). The mixture was stirred at room temperature for an hour, and diluted with ethyl acetate. The organic layer was washed with water and saturated aqueous ammonium chloride, dried over magnesium sulfate, filtered, and concentrated in vacuo. The residue was purified by silica gel column chromatography (hexane-ethyl acetate, 4:1 to 1:1) to give the title compound (180 mg) as a colorless oil.

5) Potassium tert-butoxide (27.6 mg) was added to the compound (41.0 mg, 82.4 mmol) obtained in 4) in dimethylformamide (1.0 ml), and the mixture was stirred at 80° C. for 30 minutes. After cooling the mixture to room temperature, the mixture was diluted with ethyl acetate and hexane. The organic layer was washed with water and aqueous ammonium chloride, and dried over magnesium sulfate. The solution was filtered and the filtrate was concentrated in vacuo. The residue was dissolved in dichloromethane (1.0 ml). After addition of trifluoroacetic acid (TFA) (0.50 ml) thereto, the mixture was stirred. The reaction solution was concentrated in vacuo, and the precipitates formed upon addition of water were collected by filtration, then washed with ether to give the compound (32 mg) of Working Example 40 as a yellow solid.
(Preparation Method B-3)
¹H-NMR(CDCl₃)δ:1.67–1.71(2H,m),1.87–2.12(6H,m), 5.05–5.13(1H,m),7.33–7.49(3H,m),7.61(1H,t,J=8.5 Hz), 7.94–8.01(2H,m),8.50(1H,t,J=7.5 Hz).

mass: 348(M+1)⁺

WORKING EXAMPLE 41

3-(2-benzyl-1-oxo-2,3-dihydro-1H-isoindol-4-yl)-quinoxalin-2(1H)-one

1) 2-fluoro-3-[3-oxo-4-(2-(trimethylsilyl)ethoxymethyl)-3,4-dihydroquinoxalin-2-yl]benzoic Acid The compound (methyl 2-fluoro-3-[3-oxo-4-(2-(trimethylsilyl)ethoxymethyl)-3,4-dihydroquinoxalin-2-yl]-banzoate) (1.00 g, 2.33 mmol) obtained in Working Example 28-2) was dissolved in a mixture of methanol 10 ml-tetrahydrofuran (10 ml). After addition of aqueous 1N sodium hydroxide (10 ml) at room temperature, the mixture was stirred at the same temperature for 2 hours. The reaction solution was neutralized with 1N hydrochloric acid and extracted with chloroform. The organic layer was washed with water and saturated aqueous sodium chloride, dried over anhydrous magnesium sulfate, filtered, and concentrated in vacuo to give the title compound (967 mg) as a colorless solid.

2) Ethyl N-benzyl-N-[2-fluoro-3-(3-oxo-4-(2-(trimethylsilyl)ethoxymethyl)-3,4-dihydroquinoxalin-2-yl)-benzoyl]-aminoacetate A solution of N-benzylglycine ethyl ester (50 µl, 0.265 mmol), triethylamine (101 µl, 0.723 mmol) and dimethylchloroimidazolium chloride (49 mg, 0.289 mmol) in chloroform (1 ml) was added to the compound (100 mg, 0.241 mmol) obtained in 1) in chloroform (1 ml) at room temperature, and the mixture was stirred at the same temperature for an hour. The reaction solution was concentrated and the resulting residue was purified by thin-layer silica gel chromatography (hexane-ethyl acetate, 1:1) to give the title compound (115 mg) as a pale yellow oil.

3) Ethyl 2-benzyl-3-oxo-7-(3-oxo-4-[2-(trimethylsilyl)ethoxymethyl]-3,4-dihydroquinoxalin-2-yl)isoindoline-1-carboxylate Lithium bis(trimethylsilyl)amide-11.0M tetrahydrofuran solution (212 ml, 0.212 mmol) was added to the compound (25 mg, 0.0424 mmol) obtained in 2) in tetrahydrofuran (1 ml) at room temperature under an argon atmosphere. The mixture was stirred at the same temperature for 5 minutes, after which time was added acetic acid. The reaction mixture was concentrated in vacuo, and the residue was purified by thin-layer silica gel chromatography (hexane-ethyl acetate 1:1) to give the title compound (18 mg) as a pale yellow amorphous.

4) The compound 18 mg obtained in 3) was dissolved in a mixture of methanol (1 ml)-tetrahydrofuran (1 ml). To the solution was added aqueous 1N sodium hydroxide 1 ml at room temperature, and the mixture was stirred at the same temperature for an hour. After neutralization with 1N hydrochloric acid, the reaction solution was extracted with chloroform. The organic layer was washed with saturated aqueous sodium chloride, dried over magnesium sulfate, filtered, and concentrated to give a pale yellow oil. The oil was, without purification, dissolved in 4.0M hydrogen chloride-dioxane solution. The solution was stirred at 100° C. for an hour, concentrated in vacuo to give a residue, which was purified by thin-layer silica gel chromatography (hexane-ethyl acetate 1:1) to give the compound 11 mg of Working Example 41 as a white solid.
(Preparation Method B-4)
$^1$H-NMR(DMSO-d$_6$)δ:4.72(2H,s),4.76(2H,s),7.21–7.40 (7H,m),7.50–7.90(4H,m),8.55(1H,d,J=7.6 Hz),12.6(1H,s)
mass: 368(M+1)$^+$ The following compounds of Working Examples 42 to 55 were produced according to the method as described in Working Example 41 (Preparation method B-4).

WORKING EXAMPLE 42
mass: 334(M+1)$^+$

WORKING EXAMPLE 43
mass: 334(M+1)$^+$

WORKING EXAMPLE 44
mass: 348(M+1)$^+$

WORKING EXAMPLE 45
mass: 348(M+1)$^+$

WORKING EXAMPLE 46
mass: 336(M+1)$^+$

WORKING EXAMPLE 47
mass: 334(M+1)$^+$

WORKING EXAMPLE 48
mass: 348(M+1)$^+$

WORKING EXAMPLE 49
mass: 348(M+1)$^+$

WORKING EXAMPLE 50
mass: 348(M+1)$^+$

WORKING EXAMPLE 51
mass: 318(M+1)$^+$

WORKING EXAMPLE 52
mass: 332(M+1)$^+$

WORKING EXAMPLE 53
mass: 320(M+1)$^+$

WORKING EXAMPLE 54
mass: 369(M+1)$^+$

WORKING EXAMPLE 55
mass: 391(M+1)$^+$

The following compounds of Working Examples 56 to 59 were produced according to the method as described in Working Example 28 (Preparation Method B-1).

WORKING EXAMPLE 56
$^1$H-NMR(DMSO-d$_6$)δ:1.20(2H,m),1.79(4H,m),2.20(1H,m),2.40(1H,m),3.79(2H,d,J=5.6 Hz),4.97(1H,t,J=5.6 Hz),7.39–7.46(2H,m),7.59–7.66(2H,m),8.00–8.03(2H,m),9.56(1H,m),12.76(1H,s)
mass: 394(M+1)$^+$

WORKING EXAMPLE 57
$^1$H-NMR(DMSO-d$_6$)δ:1.20–1.58(10H,m),3.81(2H,s),4.79(1H,s),7.40–7.46(2H,m),7.59–7.67(2H,m),8.07–9.00(2H,m),9.57(1H,dd,J=1.0 Hz,7.5 Hz),12.84(1H,brs)
mass: 408(M+1)$^+$

WORKING EXAMPLE 58
$^1$H-NMR(DMSO-d$_6$)δ:1.31–1.42(2H,m),1.86–2.00(6H,m),3.60(1H,m),4.29(1H,m),4.63(1H,m),7.38–7.44(2H,m),7.61(1H,m),7.65(1H,t,J=7.5 Hz),8.06(1H,dd,J=1.5 Hz,7.5 Hz),8.17(1H,dd,J=1.0 Hz, 8.1Hz), 9.59(1H,dd,J=1.5 Hz,7.5 Hz),12.80(1H,brs)
mass: 394(M+1)$^+$

WORKING EXAMPLE 59
$^1$H-NMR(DMSO-d$_6$)δ:1.29–1.47(3H,m),1.70–1.86(2H,m),2.03(1H,m),3.95(1H,m),4.19(1H,m),4.83(1H,m),7.39–7.45(2H,m),7.61(1H,m), 7.65(1H,t,J=8.1 Hz),8.06(1H,dd,J=1.0 Hz,7.5 Hz),8.17(1H,dd,J=1.0 Hz,8.1 Hz),9.60(1H,dd,J=1.0 Hz,8.1 Hz),12.81(1H,brs)
mass: 394(M+1)$^+$ The following compounds of Working Examples 60 to 66 were produced according to the method as described in Working Examples 41 (Preparation Method B-4).

WORKING EXAMPLE 60 mass: 320(M+1)$^+$

WORKING EXAMPLE 61 mass: 433(M+1)$^+$

WORKING EXAMPLE 62 mass: 437(M+1)$^+$

WORKING EXAMPLE 63 mass: 437(M+1)$^+$

WORKING EXAMPLE 64 mass: 392(M+1)$^+$

WORKING EXAMPLE 65 mass: 378(M+1)$^+$

WORKING EXAMPLE 66 mass: 360(M+1)$^+$

The following compounds of Working Example 67 to 75 were produced according to the method described in Working Example 22 (Preparation Method A).

WORKING EXAMPLE 67 mass: 364(M+1)$^+$

WORKING EXAMPLE 68 mass: 424(M+1)$^+$

WORKING EXAMPLE 69 mass: 424(M+1)$^+$

WORKING EXAMPLE 70 mass: 374(M+1)$^+$

WORKING EXAMPLE 71 mass: 374(M+1)$^+$

WORKING EXAMPLE 72 mass: 414(M+1)$^+$

WORKING EXAMPLE 73 mass: 391(M+1)$^+$

WORKING EXAMPLE 74 mass: 391(M+1)$^+$

WORKING EXAMPLE 75 mass: 404(M+1)$^+$

The following compounds of Working Examples 76, 77 and 81 were produced according to the method described in Working Example 22 (Preparation Method A).

WORKING EXAMPLE 76

$^1$H-NMR(DMSO-d$_6$)δ:1.26–2.06(8H,m),3.89–4.81(3H,m),7.18–7.38(2H,m),7.63(1H,d,J=8.0 Hz),7.67(1H,t,J=8.0 Hz),7.85(1H,d,J=7.3 Hz),7.83(1H,d,J=8.7 Hz),8.01(1H,d,J=7.6 Hz),8.71(1H,dd,J=1.0 Hz,7.8 Hz).

mass: 380(M+1)$^+$

WORKING EXAMPLE 77 mass: 426(M+1)$^+$

The following compounds of Working Examples 78 to 80 were produced according to the method described in Working Example 14 (Preparation method A).

WORKING EXAMPLE 78 mass: 389 (M+1)$^+$

WORKING EXAMPLE 79 mass: 360(M+1)$^+$

WORKING EXAMPLE 80 mass: 322 (M+1)$^+$

WORKING EXAMPLE 81 mass: 426 (M+1)$^+$

WORKING EXAMPLE 82

3-(2-cyclopentyl-1-oxo-2,3-dihydro-1H-isoindol-4-yl)-6-N-methylpiperazinoquinoxalin-2(1H)-one A synthetic precursor 1-(2,4-dimethoxybenzyl)-3-(2-cyclopentyl-1-oxo-2,3-dihydro-1H-isoindol-4-yl)-6-bromoquinoxalin-2(1H)-one (30 mg) of Working Example 81, Pd$_2$(dba)$_3$ (8 mg), BINAP (2,2'-bis(diphenylphosphino)-1,1'-binaphthyl) (10 mg), sodium tert-butoxide (17 mg) and N-methylpiperazine (16 mg) were added to tetrahydrofuran (1 ml), and the mixture was heated in a sealed tube at 100° C. for 20 minutes. The reaction solution was concentrated in vacuo and trifluoroacetic acid (2 ml) was added to the residue. The mixture was heated in a sealed tube at 100° C. for 20 minutes. After concentrating the reaction solution in vacuo, the resulting residue was purified by thin-layer silica gel chromatography (chloroform-methanol, 10:1) to give the compound (1.2 mg) of Working Example 82 as a yellow solid.

$^1$H-NMR(DMSO-d$_6$)δ:1.65–1.81(4H,m),1.88–1.96(2H,m),2.30(3H,s),2.55(4H,brs),3.24(4H,brs),4.63(1H,m),4.83(2H,s),7.29–7.32(2H,m),7.43(1H,d,J=8.0 Hz),7.67(1H,t,J=8.0 Hz),7.85(1H,d,J=8.0 Hz),8.48(1H,d,J=8.0 Hz),12.55(1H,brs).

mass: 444(M+1)$^+$.

WORKING EXAMPLE 83

7-(1-benzylpyrrolidin-3-yl)-3-(2-cyclopentyl-1-oxo-2,3-dihydro-1H-isoindol-4-yl)quinoxalin-2(1H)-one 1) 4-vinyl-2-fluoronitrobenzene 4-Chloro-2-fluoronitrobenzene (300 mg, 1.71 mmol), Pb$_2$(dba)$_3$ (236 mg, 0.228 mmol), tributyl (vinyl) tin (333 mg, 1.14 mmol), tri-2-furylphosphine (212 mg, 0.912 mmol) and lithium chloride (193 mg, 4.56 mmol) were added to methylpyrrolidinone (5 ml), and the mixture was stirred in a sealed tube at 120° C. for one hour. The mixture was diluted with chloroform-methanol, and filtered through a Celite Pad. After concentrating the filtrate, the concentrate was dissolved in ethyl acetate and washed with aqueous potassium fluoride. The organic layer was dried over magnesium sulfate, concentrated in vacuo, and purified by thin-layer silica gel chromatography (hexane-ethyl acetate, 5:1) to give the title compound (146 mg) as a pale yellow oil.

2) 4-(N-benzyl-3-pyrrolidyl)-2-fluoronitrobenzene

The vinyl compound (146 mg) in 1) and N-(trimethylsilylmethyl)-N-methoxymethylbenzylamine (1.12 ml) were added to dichloromethane (10 ml). After cooling the mixture to 0° C., trifluoroacetic acid (0.034 ml) was added thereto. The mixture was stirred at room temperature for 30 minutes, and aqueous sodium hydrogen carbonate was added. The mixture was extracted with chloroform, and the extract was washed with water and saturated aqueous sodium chloride. The extract was dried over anhydrous magnesium sulfate, concentrated in vacuo, and purified by thin-layer silica gel chromatography (chloroform-methanol, 80:1) to give the title compound (336 mg) as a pale yellow oil.

3) 4-(N-benzyl-3-pyrrolidyl)-2-(4-methoxybenzyl-amino)nitrobenzene

The compound (336 mg) obtained in 2) and 4-methoxybenzylamine (0.114 ml) were added to methylpyrrolidinone (3 ml), and the mixture was stirred in a sealed tube at 120° C. for 30 minutes. The reaction solution was extracted with ether and the extract was washed with water and brine. The extract was dried over anhydrous magnesium sulfate, concentrated in vacuo to give the title compound (558 mg) as a crude orange oil.

4) 4-(N-benzyl-3-pyrrolidyl)-2-(4-methoxybenzylamino)aniline

The compound (270 mg) obtained above was dissolved in ethanol (20 ml), and iron dust (0.5 g) was added thereto. After addition of concentrated hydrochloric acid (0.5 ml), the mixture was stirred at 120° C. for 5 minutes. The reaction mixture was filtered through a Celite Pad, and washed with chloroform-methanol. The filtrate was then concentrated in vacuo and the thus obtained residue was extracted with chloroform. The extract was washed with aqueous sodium hydrogen carbonate and brine. The extract was dried over anhydrous magnesium sulfate and concentrated in vacuo to give a residue, which was purified by silica gel column chromatography (chloroform-methanol, 80:1) to yield the title compound (111 mg) as a yellow oil.

5) The compound of Working Example 83 was produced by the method similar to Working Example 22, using the compound obtained in 4).
(Preparation Method A)
$^1$H-NMR(CDCl$_3$)δ:1.11–1.94(9H,m),2.31–2.34(1H,m), 2.57–2.91(4H,m), 3.43–3.54(1H,m),3.54–3.56(2H,m),4.70 (2H,s),4.67–4.74(1H,m), 7.07–7.26(7H,m),7.29–7.51(1H, m),7.70(1H,d,J=7.8 Hz),7.87(1H,d,J=7.8 Hz),8.58(1H,d,J= 7.8 Hz).
mass: 505(M+1)$^+$.

WORKING EXAMPLE 84

7-(pyrrolidin-3-yl)-3-(2-cyclopentyl-1-oxo-2,3-dihydro-1H-isoindol-4-yl)quinoxalin-2(1H)-one The compound 8 mg obtained by working up in the same manner as in Working Example 22-1) using the compound obtained in Working Example 83-4) was dissolved in 1,2-dichloroethane (1 ml) To the solution was added 1-chloroethyl chloroformate (10 μl) at 0° C. Then the mixture was heated in a sealed tube at 110° C. for one hour and the reaction solution was concentrated. After addition of methanol (1 ml) thereto, the mixture was heated at 90° C. for 21 hours, and then concentrated to give a residue, to which was added trifluoroacetic acid (0.8 ml). The mixture was stirred in a sealed tube at 120° C. for 10 hours, and then extracted with chloroform. The extract was washed with brine, dried over anhydrous magnesium sulfate, concentrated to give a residue. The residue was purified by thin-layer silica gel chromatography (chloroform-methanol, 20:1) to give the compound (0.52 mg) of Working Example 84.

mass: 415(M+1)$^+$.

The following compounds of Working Examples 85 to 87 were produced according to the method described in Working Example 28 (Preparation method B-1).

WORKING EXAMPLE 85

$^1$H-NMR(DMSO-d$_6$)δ:1.65–1.71(2H,m),1.81–1.87(4H, m),2.03–2.11(2H,m),4.77–4.82(1H,m),7.57–7.68(2H,m), 7.77(1H,d,J=6.6 Hz), 8.07(1H,d,J=7.5 Hz),8.61(1H,d,J=4.8 Hz),9.60(1H,d,J=7.5 Hz),12.93(1H,s).

mass: 365(M+1)$^+$.

WORKING EXAMPLE 86

$^1$H-NMR(DMSO-d$_6$)δ:4.77(2H, q, J=9.3 Hz),7.63–7.68 (1H,m),7.73–7.84(2H,m),8.21(1H,d,J=8.1 Hz),8.63–8.65 (1H,m),9.66(1H,d,J=8.1 Hz),13.02(1H,s).

mass: 379(M+1)$^+$.

WORKING EXAMPLE 87

$^1$H-NMR(DMSO-d$_6$)δ:1.35–1.44(2H,m),1.79–1.89(2H, m),1.90–1.97(4H,m),3.80–3.92(1H,m),4.24–4.28(1H,m), 7.65–7.72(2H,m),7.81(1H,d,J=8.4 Hz),8.12(1H,d,J=6.6 Hz),8.66(1H,d,J=4.5 Hz),9.65(1H,d,J=7.8 Hz),12.97(1H,s), 13.57(1H,s).

mass: 395(M+1)$^+$.

WORKING EXAMPLE 88

5-hydroxy-3-[2-(2,2,2-trifluoroethyl)-3-oxo-2,3-dihydro-1,2-benzisothiazol-7-yl]quinoxalin-2(1H)-one 1) 3-(3-iodo-2-fluorophenyl)-5-tert-butyldimethylsilyloxyquinoxalin-2(1H)-one The keto ester (40.9 g, 0.127 mol) obtained in Working Example 24-2) and acetic acid (6 ml) were added to 3-t-butyldimethylsilyloxy-1,2-phenylenediamine (30.3 g, 0.127 mol) in toluene (400 ml). The mixture was heated under reflux for an hour, and then cooled to room temperature. The reaction mixture was filtered through a Celite Pad, and concentrated in vacuo to give a residue, to which was added hexane. The resulting solid was filtered to give the title compound (40.1 g) as a yellow brown solid.

2) 3-(3-iodo-2-fluorophenyl)-1-(2-(trimethylsilyl)-ethoxymethyl)-5-hydroxyquinoxalin-2(1H)-one The compound (30.0 g, 60.5 mmol) obtained above and 2-trimethylsilylethoxymethyl chloride (13.1 g, 78.6 mmol) were dissolved in tetrahydrofuran (300 ml). To the solution was added sodium hydride (3.14 g, 60% 78.6 mmol) at 0° C., and the mixture was warmed to room temperature. The mixture was stirred for an hour, and then added to aqueous ammonium chloride. The reaction solution was extracted with ethyl acetate. The organic layer was washed with brine, dried over anhydrous magnesium sulfate, concentrated in vacuo and purified by silica gel column chromatography (hexane-ethyl acetate) to give a SEM protected compound (40.2 g) as a pale yellow amorphous. The amorphous was dissolved in tetrahydrofuran (100 ml), and 1.0M tetrabutylammonium fluoride in tetrahydrofuran (90 ml) was added. The mixture was stirred for 15 minutes, and water was added thereto. The mixture was extracted with ethyl acetate. The extract was washed with water and saturated aqueous sodium chloride, dried over anhydrous magnesium sulfate, concentrated in vacuo to give a residue, which was dissolved in 4N hydrogen chloride-dioxane solution. The solution was stirred for 30 minutes, and concentrated in vacuo. Chloroform was added to the concentrate to remove insoluble materials by filtration. The filtrate was concentrated, and the resulting crude residue was purified by silica gel chromatography (hexane-ethyl acetate) wherein the t-butyldimethylsilyl protecting group was deprotected to give the title compound (14 g) as a pale yellow solid.

3) 5-hydroxy-3-[2-(2,2,2-trifluoroethyl)-3-oxo-2,3-dihydro-1,2-benzisothiazol-7-yl]-1-(2-trimethylsilyl)-ethoxymethylquinoxalin-2(1H)-one The title compound was obtained as a yellow solid by derivatization of the compound as the starting material obtained in 2), according to the method as described in Working Example 38 and Working Example 28-2) to 28-6).

4) The 1-trimethylsilylethoxymethyl protecting group of the compound obtained in 3) was deprotected by the method in Working Example 28-7) to give the compound of Working Example 88 as a yellow solid.
(Preparation Method B-1)
$^1$H-NMR(DMSO-$d_6$)δ:4.65(1H,d,J=12.5 Hz),4.73(1H,d,J=12.5 Hz),6.81–6.90(2H,m),7.42(1H,t,J=8.1 Hz),7.73(1H,t,J=7.7 Hz),8.17(1H,d,J=7.7 Hz),9.67(1H,d,J=7.7 Hz),11.1 (1H,s),12.8(1H,s).
mass: 394(M+1)$^+$.

WORKING EXAMPLE 89

5-methoxy-3-[2-(2,2,2-trifluoroethyl)-3-oxo-2,3-dihydro-1,2-benzisothiazol-7-yl]quinoxalin-2(1H)-one Methanol (50 μl), triphenylphosphine (17 mg, 66 μmol) and diethyl azodicarboxylate (29 μl) were added to tetrahydrofuran solution (1 ml) of the compound (5-hydroxy-3-[2-(2,2,2-trifluoroethyl)-3-oxo-2,3-dihydro-1,2-benzisothiazol-7-yl]-1-(2-trimethylsilyl)ethoxymethyl-quinoxalin-2(1H)-one) (10 mg, 22 μmol) obtained in Working Example 88-3). The mixture was stirred at room temperature for 30 minutes. After concentrating the reaction solution, the resulting residue was purified by thin-layer silica gel chromatography (hexane-ethyl acetate 2:1) to give a yellow oil (10 mg). The oil was dissolved in 4N hydrogen chloride-dioxane solution (1 ml), and the solution was stirred in a sealed tube at 100° C. for 2 hours. The solid precipitated upon addition of ether was filtered to give the compound (5 mg) of Working Example 89 as a yellow solid.
$^1$H-NMR(DMSO-$d_6$)δ:4.12(3H,s),4.62–4.82(2H,m),6.95–7.03(2H,m),7.55(1H,t,J=8.3 Hz),7.72(1H,t,J=7.7 Hz),8.13(1H,d,J=7.5 Hz),9.63(1H,d,J=7.9 Hz),12.97(1H,s).
mass: 408(M+1)$^+$.

WORKING EXAMPLE 90

5-benzyloxy-3-[2-(2,2,2-trifluoroethyl)-3-oxo-2,3-dihydro-1,2-benzisothiazol-7-yl]quinoxalin-2(1H)-one The compound (5-hydroxy-3-[2-(2,2,2-trifluoroethyl)-3-oxo-2,3-dihydro-1,2-benzisothiazol-7-yl]-1-(2-trimethylsilyl)ethoxymethylquinoxaline-2(1H)-one) obtained in Working Example 88-3) was used according to the method described in Working Example 89 to give the title compound.
mass: 484(M+1)$^+$.

The following compounds of Working Examples 91 to 94 were produced according to the method described in Working Examples 88 and 89.

WORKING EXAMPLE 91 mass: 380(M+1)$^+$.

WORKING EXAMPLE 92 mass: 471(M+1)$^+$.

WORKING EXAMPLE 93 mass: 410(M+1)$^+$.

WORKING EXAMPLE 94 mass: 500(M+1)$^+$.

According to the procedure described in the Working Example 28 (Preparation Method B-1), the compounds of the Working Examples 95 to 97 described below were synthesized.

WORKING EXAMPLE 95

$^1$H-NMR(DMSO-$d_6$)δ:1.68–1.77(2H,m),1.88–1.98(4H,m), 2.08–2.13(2H,m),4.81–4.86(1H,m),7.70(1H,t,J=7.8 Hz), 8.08(1H,d,J=5.4 Hz),8.14(1H,d,J=7.5 Hz),8.57(1H,d,J=5.4 Hz), 8.78(1H,s),9.66(1H,d,J=7.8 Hz),13.11(1H,brs).
mass: 365(M+1)$^+$.

WORKING EXAMPLE 96

$^1$H-NMR(DMSO-$d_6$)δ:1.69–1.73(2H,m),1.90–2.12(6H,m), 4.79–4.88(1H,m),7.49(1H,d,J=6.0 Hz),7.70(1H,t,J=7.5 Hz), 8.13(1H,d,J=7.8 Hz),8.63(1H,d,J=6.3 Hz),9.45(1H,s),9.56(1H,d,J=7.8 Hz),13.50(1H,brs).
mass: 365(M+1)$^+$.

WORKING EXAMPLE 97

$^1$H-NMR(DMSO-$d_6$)δ:1.70–1.76(2H,m),1.90–2.00(4H,m), 2.07–2.14(1H,m),4.83–4.88(1H,m),7.48–7.52(1H,m),7.70(1H,t,J=7.8 Hz),8.10(1H,d,J=7.8 Hz),8.52(1H,d,J=7.5 Hz), 8.63(1H,d,J=4.5 Hz),9.69(1H,d,J=7.8 Hz),13.29(1H,s).
mass: 365(M+1)$^+$.

WORKING EXAMPLE 98

7-(1-benzylpyrrolizin-3-yl)-3-(2-cyclopentyl-3-oxo-2,3-dihydro-1,2-benzisothiazol-7-yl)quinoxalin-2(1H)-one According to the procedure described in Working Example 88, the title compound was synthesized, using the compound obtained in Working Example 83-4) (4-(N-benzyl-3-pyrrolizinyl)-2-(4-methoxybenzylamino)aniline).
(Preparation Method B-1)
$^1$H-NMR(DMSO-$d_6$)δ:1.21–2.46(10H,m),3.20–3.40(2H,m), 3.44–3.51(2H,m),4.14–4.33(2H,m),4.42–4.59(1H,m), 4.81–4.86(3H,m),9.55–9.64(1H,m),12.78(1H,s),13.59(1H,s).
mass: 523(M+1)$^+$.

WORKING EXAMPLE 99

According to the procedure described in Working Example 84, the title compound was synthesized, using the compound of Working Example 98

$^1$H-NMR(DMSO-d$_6$)δ:1.21–2.41(10H,m),3.50–3.69(2H, m), 3.79–3.85(2H,m),3.99–4.09(1H,m),4.70–4.90(1H,m), 7.15–7.22(1H,m),7.30–7.39(1H,m),7.56(1H,t,J=5.4 Hz), 7.85–8.01(2H,m),9.46–9.54(1H,m).

WORKING EXAMPLE 100

According to the procedure described in Working Example 98, the title compound was synthesized (Preparation Method B-1).

$^1$H-NMR(CDCl$_3$)δ:1.00–3.20(21H,m),3.20–3.40(2H,m), 3.60–3.75(2H,m),4.19–4.28(1H,m),4.80–5.00(1H,m), 7.30–7.75(3H,m),7.80–8.20(2H,m),9.48–9.60(1H,m),13.40 (1H,s)

mass: 515(M+1)$^+$.

According to the procedure described in Working Examples 98 and 99 respectively, the compounds of Working Examples 101 to 106 described below were synthesized (Preparation Method B-1).

WORKING EXAMPLE 101

$^1$H-NMR(DMSO-d$_6$)δ:1.78–1.90(1H,m),2.22–2.45(1H, m), 2.45–2.59(1H,m),2.78–2.87(1H,m),2.87(1H,t,J=9.0 Hz), 3.16–3.50(2H,m),3.66(1H,d,J=5.4 Hz), 4.72(1H,dd,J= 9.3 Hz,18.9 Hz),7.21–7.40(6H,m),7.45–7.68(1H,m), 7.69 (1H,t,J=7.5 Hz),8.01–8.14(2H,m),9.54(1H,t,J=6.0 Hz).

mass: 537(M+1)$^+$.

WORKING EXAMPLE 102

$^1$H-NMR(DMSO-d$_6$)δ:1.99–2.03(1H,m),3.09–3.38(2H, m), 3.45–3.56(2H,m),3.56–3.70(2H,m),4.72(1H,dd,J=9.6 Hz,19.5 Hz), 7.27(1H,s),7.44(1H,d,J=8.4 Hz),7.68(1H,t,J= 7.8 Hz), 8.04–8.10(2H,m),9.44–9.53(1H,m),9.52(1H,d,J= 7.5 Hz), 12.90(1H,s).

mass: 447(M+1)$^+$.

WORKING EXAMPLE 103

$^1$H-NMR(DMSO-d$_6$)δ:1.16–1.96(10H,m),2.10–2.27(2H, m), 2.80–3.17(2H,m),3.21–3.53(4H,m),4.74(1H,dd,J=8.4 Hz,17.7 Hz), 7.32–7.44(1H,m),7.71(1H,t,J=7.5 Hz), 8.05–8.17(2H,m), 9.54–9.57(1H,m),12.80 (1H,brs).

mass: 529(M+1)$^+$.

WORKING EXAMPLE 104

$^1$H-NMR(DMSO-d$_6$)δ:1.22–1.99(9H,m),1.99–2.35(2H, m), 2.49–2.61(1H,m),2.87(1H,t,J=8.4 Hz),2.77–2.90(1H, m), 3.31–3.67(3H,m),4.23–4.32(1H,m),4.68(1H,brs), 7.20–7.46(7H,m),7.63(1H,t,J=8.1 Hz),8.02–8.09(2H,m), 9.54(1H,d,J=8.1 Hz),12.78(1H,brs).

mass: 553(M+1)$^+$.

WORKING EXAMPLE 105

$^1$H-NMR(DMSO-d$_6$)δ:1.82–2.05(6H,m),2.05–2.57(5H, m), 3.01–3.66(4H,m),4.24–4.31(1H,m),7.28(1H,s), 7.42 (1H,d,J=6.6 Hz),7.60–7.64(1H,m),8.02–8.11(1H,m), 8.12 (1H,d,J=8.4 Hz),9.31–9.53(2H,m),9.54(1H,d,J=6.3 Hz), 12.87(1H,brs).

mass: 463(M+1)$^+$.

WORKING EXAMPLE 106

$^1$H-NMR(DMSO-d$_6$)δ:1.17–1.96(9H,m),2.22–2.49(2H, m), 3.38–3.58(2H,m),4.24–4.28(1H,m),4.67–4.68(1H,m), 7.28–7.41(2H,m),7.63(1H,t,J=7.8 Hz),8.02–8.10(2H,m), 9.54(1H,d,J=8.1 Hz),12.77(1H,brs).

mass: 545(M+1)$^+$.

WORKING EXAMPLE 107

3-(3-oxo-2-(2,2,2-trifluoro-1-(hydroxymethyl)ethyl)-2,3-dihydro-1,2-benzisothiazol-7-yl)quinoxalin-2(1H)-one 1) 2-amino-3,3,3-trifluoropropanol N-Methylhydroxylamine hydrochloride (3.90 g, 46.7 mmol) and sodium acetate (3.83 g, 46.7 mmol) were added to a solution of ethyl 3,3,3-trifluoropyruvate (7.22 g, 42.4 mmol) in ethanol (50 ml), and the mixture was stirred at room temperature overnight. Then insolubles were removed by filtration, and the filtrate was concentrated in vacuo. The obtained residue was dissolved in tetrahydrofuran, and excess lithium aluminum hydride was added to the solution. The mixture was refluxed under heating for 2 hours. The reaction mixture was cooled down to room temperature. Sodium sulfate was added to the reaction mixture, and the obtained mixture was stirred for 30 minutes. Moreover, a solution of potassium fluoride was added to the mixture, and the mixture was stirred for 30 minutes. The reaction mixture was filtered through a Celite Pad, and then the obtained filtrate was concentrated in vacuo to give the title compound.

2) A little excess imidazole and t-buthyldimethylsilyl chloride were added to a solution of aminoalcohol (269 mg, 2.08 mmol) mentioned above in dichloromethane (10 ml), and the mixture was stirred at room temperature for an hour. Chloroform was added to the reaction mixture, and the mixture was separated by water. The organic layer was dried over anhydrous magnesium sulfate and concentrated in vacuo to give a protected silyl derivative as a yellow oil.

3) The reaction similar to Working Example 28 was carried out by using the amine obtained in 2) as a starting material to give the compound of Working Example 107 as a yellow powder.
(Preparation Method B-1)

$^1$H-NMR(DMSO-d$_6$)δ:4.02–4.18(2H,m),5.19–5.26(1H, m), 7.02–7.07(1H,m),7.22–7.23(1H,m),7.26–7.36(1H,m), 7.60(1H,t,J=7.5 Hz),7.88(1H,d,J=6.6 Hz), 7.98(1H, dd, J=1.5 Hz, 7.5 Hz),9.92(1H,brs).

mass: 408(M+1)$^+$.

WORKING EXAMPLE 108

The title compound was synthesized by the method similar to the procedure described in Working Example 28 (Preparation Method B-1).

$^1$H-NMR(DMSO-d$_6$)δ:4.78(2H,t,J=16.2 Hz),7.40–7.46 (2H,m), 7.62(1H,t,J=7.9 Hz),7.72(1H,t,J=7.2 Hz),8.14–8.30 (2H,m), 9.60(1H,d,J=7.4 Hz),12.78 (1H,brs).

mass: 428(M+1)$^+$.

WORKING EXAMPLE 109

3-(2-cyclopenthyl-3-oxo-2,3-dihydroisothiazolo[4,5-b]pyridin-7-yl)quinoxalin-2(1H)-one 1) Ethyl (3-fluoro-2-iodopyridin-4-yl)oxoacetate n-Butyllithium (1.59M in hexane) (1.75 ml, 2.78 mmol) was added to a solution of diisopropylamine (390 μl, 2.78 mmol) in tetrahydrofuran (10 ml) at −78° C., and the mixture was warmed up to 0° C., then stirred for 30 minutes. The mixture was again cooled down to −78° C. A solution of 3-fluoro-4-iodopyridine (500 mg, 2.24 mmol) synthesized by the method of P. Rocca et. al. (Tetrahedron 49,49–64 (1993)) in tetrahydrofuran (4 ml) was added to said mixture, and the resulting mixture was stirred for 1.5 hours. The reaction mixture was dropwise added to a solution of diethyl oxalate (900 μl, 6.63 mmol) in tetrahydrofuran (10 ml) at −78° C. under stirring. The mixture was warmed up to room temperature and stirred for 20 minutes. Aqueous ammonium chloride was added to the reaction mixture, and the mixture was extracted with chloroform. The extract was dried over anhydrous magnesium sulfate, and concentrated in vacuo. The residue was purified by silica gel column chromatography (hexane:ethyl acetate, 3:2) to give the title compound (659 mg).

2) The reaction similar to Working Example 28 was carried out, using the ketoester mentioned above to give the compound of the Working Example as a yellow solid.
(Preparation Method B-1)

$^1$H-NMR(DMSO-d$_6$)δ:1.70–1.78(2H,m),1.85–2.00(4H, m), 2.08–2.17(2H,m),4.87(1H,m),7.42–7.49(2H,m), 7.66 (1H,t,J=8.0 Hz),8.13(1H,d,J=8.0 Hz),8.90(1H,d,J=7.3 Hz), 9.28(1H,d,J=7.3 Hz),12.99(1H,brs).

mass: 365(M+1)$^+$.

WORKING EXAMPLE 110

3-(2-cyclopenthyl-3-oxo-2,3-dihydro-1H-indazol-7-yl)-5-hydroxyquinoxalin-2(1H)-one 1)3-(3-iodo-2-fluorophenyl)-1-(2-(trimethylsilyl)-ethoxymethyl)-5-(2-(trimethylsilyl) ethoxymethyloxy)-quinoxalin-2(1H)-one 2-trimethylsilylethoxymethyl chloride (3.2 g) was added to a solution of the compound obtained in Working Example 88-2) (3-(3-iodo-2-fluorophenyl)-1-(2-(trimethylsilyl) ethoxymethyl)-5-hydroxyquinoxalin-2(1H)-one) (7.0 g) in tetrahydrofuran (100 ml), and then sodium hydride (760 mg, 60%) was added to the mixture at 0° C. The mixture was warmed up to room temperature and stirred for an hour. Aqueous ammonium chloride was added to the reaction mixture, and the resulting mixture was extracted with ethyl acetate. The organic layer was washed with brine, dried over anhydrous magnesium sulfate, and concentrated in vacuo. The residue was purified by silica gel column chromatography (hexane:ethyl acetate, 10:1) to give the titled compound (8.8 g) as a pale yellow amorphous.

2) 2-fluoro-3-[3-oxo-4-(2-(trimethylsilyl) ethoxymethyl)-3,4-dihydro-8-(2-(trimethylsilyl) ethoxymethyloxy)-quinoxalin-2-yl]benzoic Acid Using the compound obtained in 1), the title compound was prepared by introduction of methoxycarbonyl group into the benzene ring at position 3 according to the procedure of Working Example 28-2), followed by hydrolysis in a usual manner.

3) Triethylamine (150 μl) and dimethylchloroimidazolium chloride (100 mg) were added to a solution of the carboxylic acid derivative obtained in 2) (264 mg, 0.471 mmol) in dichloromethane (5 ml), and the mixture was stirred for 10 minutes. After addition of N-t-butoxycarbonyl-cycropenthylhydrazine (112 mg), the mixture was stirred at room temperature for 2 hours and chloroform was added thereto. The mixture was washed with water and 1N hydrochloric acid, dried over anhydrous magnesium sulfate and concentrated in vacuo to give a yellow oil. The oil was treated with 4N hydrochloric acid-dioxane to remove BOC group and SEM group at position 5. The deprotected compound was purified by silica gel column chromatography to give a cyclopenthylhydrazine derivative as a yellow solid.

The derivative was dissolved in dimethylformamide (5 ml), and the solution was heated in a sealed tube at 120° C. for 2 hours. The reaction mixture was added to the solvent of hexane-ethyl acetate (1:1), and the obtained mixture was washed successively with water, aqueous sodium hydrogen carbonate and aqueous ammonium chloride. The mixture was dried over anhydrous magnesium sulfate and concentrated in vacuo to give a yellow solid (70 mg). The SEM group at position 1 was deprotected by heating in 4N hydrochloric acid-dioxane in a usual manner to give the compound of Working Example 110 (13 mg).
(Preparation Method B-2b)

$^1$H-NMR(DMSO-d$_6$)δ:1.63–2.04(8H,m),4.85–4.91(1H, m), 6.79–6.84(2H,m),7.24(1H,t,J=7.8 Hz),7.38(1H,t,J=8.0 Hz), 7.82(1H,d,J=7.8 Hz),9.21(1H,d,J=8.0 Hz), 10.52 (1H, brs),12.61(1H,brs).

mass: (M+1)$^+$.

According to the procedure described in Working Example 110, the compounds of Working Examples 111 to 113 described below were synthesized (Preparation Method B-2b).

WORKING EXAMPLE 111

$^1$H-NMR(DMSO-d$_6$)δ:3.47(3H,s),6.75–6.85(2H,m), 7.26 (1H,t,J=7.7 Hz),7.35–7.43(1H,m),7.81(1H,d,J=7.7 Hz), 8.99(1H,d,J=7.7 Hz),10.51(1H,brs),12.60(1H,brs).

mass: 309(M+1)$^+$.

WORKING EXAMPLE 112

$^1$H-NMR(DMSO-d$_6$)δ:3.50(3H,s),4.98(2H,s),7.15–7.58 (4H,m), 7.52(1H,t,J=7.7 Hz),7.82(1H,d,J=7.7 Hz),8.19(1H, d,J=7.7 Hz), 11.70 (1H,brs),12.82(1H,brs).

mass: 323(M+1)$^+$.

WORKING EXAMPLE 113

$^1$H-NMR(DMSO-d$_6$)δ:2.74(3H,s),3.45(3H,s),7.20–7.30 (3H,m), 7.46(1H,t,J=7.7 Hz),7.82(1H,d,J=7.7 Hz),9.02(1H, d,J=7.7 Hz), 10.22 (1H,brs),12.73(1H,brs).

mass: 307(M+1)$^+$.

WORKING EXAMPLE 114

9-(3-oxo-3,4-dihydroquinoxalin-2-yl)-3,4-dihydro-1,4-benzoxazepin-5(2H)-one

1) N-Butyllithium (12.5 ml, 1.6M in hexane) was added to a solution of 2,6-dibromophenol (5.00 g) in tetrahydrofuran (50 ml) at −78° C. under stirring, and the mixture was warmed up to 0° C. 2-Trimethylsilylethoxymethyl chloride (3.86 ml) was added to the reaction mixture. The mixture was stirred at room temperature, and then dropwise added to a solution of n-butyllithium (13.6 ml) in tetrahydrofuran (50 ml) at −78° C. The resulting mixture was further stirred at the same temperature for 20 minutes, and then added to a solution of diethyl oxalate (8.10 ml) in tetrahydrofuran 50 ml at −78° C. under stirring. The thus obtained mixture was warmed up to room temperature and further stirred for 30 minutes. The reaction mixture was added to aqueous ammonium chloride, and the obtained mixture was extracted with ethyl acetate. The organic layer was washed with ammonium chloride and water, dried over anhydrous magnesium sulfate, and concentrated in vacuo to give a ketoester derivative (7.54 g).

2) 1,2-phenylenediamine (2.3 g) and acetic acid (1 ml) were added to a solution of the compound mentioned above (7.54 g) in toluene (50 ml), and the mixture was heated under reflux for an hour. The solid formed upon addition of ether to the reaction mixture at 0° C. was filtered to give a quinoxaline derivative (1.91 g). The compound was dissolved in tetrahydrofuran (500 ml), and sodium hydride (60%, 1.0 g) and 2-trimethylsilylethoxymethyl chloride (8.6 ml) were added to the solution at room temperature. The mixture was stirred for an hour. Aqueous ammonium chloride was added to the reaction mixture, and then extracted with ethyl acetate. The organic layer was washed with water and aqueous ammonium chloride, dried over anhydrous magnesium sulfate, and concentrated in vacuo to give a compound protected by the SEM group.

3) The compound obtained in 2) was dissolved in a mixture of dimethylformamide (20 ml)-methanol (20 ml), and sodium hydrogen carbonate (1.26 g) was added thereto. The air in the reaction system was replaced by nitrogen, and palladium acetate(II) (250 mg) and 1,3-bis (diphenylphosphino)propane (920 mg) were added to the reaction mixture under an atmosphere of nitrogen and then nitrogen in the reaction system was replaced by carbon monoxide (4 atm). The reaction mixture was heated at 100° C. for 17 hours, cooled down to room temperature and filtered through a Celite Pad. After addition of ethyl acetate to the filtrate, the organic layer was washed with water and brine, dried over anhydrous magnesium sulfate, and concentrated in vacuo. The residue was treated with an acid and then purified by silica gel column chromatography (chloroform) to give a 2'-hydroxy-3'-methoxycarbonyl derivative (1.59 g).

4) The compound of 3) (1.19 g) was subjected to hydrolysis by 1N sodium hydroxide in tetrahydrofuran-methanol solvent to give a 2'-hydroxy-3'-carboxyl derivative (1.05 g).

5) A little excess amount of 1-amino-2-ethanol, 1-hydroxybenz-triazole monohydrate and 1-(3-dimethylaminopropyl)-3-ethylcarbodiimide hydrochloride were added respectively to a solution of the compound of 4) (20 mg) in chloroform (1.5 ml), and then the mixture was stirred overnight. The reaction mixture was concentrated in vacuo. The residue was purified by silica gel thin-layer chromatography to give an amide derivative (13.2 mg).

6) A little excess amount of diethyl azodicarboxylate and triphenylphosphine were added to a solution of the compound of 5) (13.2 mg) in chloroform (1 ml), and then the mixture was stirred overnight. The reaction mixture was concentrated in vacuo. The residue was purified by silica gel thin-layer chromatography to give a benzotetrahydrooxepinone derivative (9.5 mg).

7) The 1-SEM group in the compound of 6) (8.0 mg) was deprotected by 4N hydrochloric acid-dioxane in a usual manner to give the compound of Working Example 114 (1.2 mg).
(Preparation Method C)
$^1$H-NMR(DMSO-d$_6$)δ:3.65(2H,q,J=6.3 Hz),3.78(2H,t,J=6.3 Hz), 7.02(1H,t,J=7.8 Hz),7.31–7.37(2H,m),7.57(1H,m), 7.80(1H,d,J=7.8 Hz),7.98(1H,d,J=7.8 Hz),8.06(1H,d,J=7.8 Hz), 9.21(1H,t,J=6.3 Hz),12.62(1H,brs).
 mass: 308(M+1)$^+$.

WORKING EXAMPLE 115

9-(3-oxo-3,4-dihydroquinoxalin-2-yl)-1,2,3,4-tetrahydro-5H-1,4-benzodiazepin-5-one 1) The reaction similar to Working Example 114-5) was carried out using the compound of Working Example 114-4) and N-t-butoxycarbonyl-ethylenediamine as a starting material to give an amide derivative. BOC group of said amide derivative was removed by hydrochloric acid-methanol to give an amide derivative.

2) Diisopropylethylamine (40 μl) was added to a solution of the amide derivative of 1) (53 mg) in dimethylformamide (5 ml), and the mixture was heated in a sealed tube at 120° C. overnight. The mixture was concentrated in vacuo. The residue was purified by silica gel thin-layer column chromatography to give a benzotetrahydrodiazepinone derivative (13 mg).

3) The compound of 2) (13 mg) was treated with 4N hydrochloric acid-dioxane in a usual manner to remove the 1-SEM group, and purified by silica gel thin-layer column chromatography to give the compound of Working Example 115 (3.9 mg).
(Preparation Method B-5)
$^1$H-NMR(DMSO-d$_6$)δ:3.25–3.45(4H,m),6.55(1H,brs), 6.74(1H,t,J=7.8 Hz),7.24–7.33(2H,m),7.47–7.52(2H,m), 7.77–7.79(2H,m),8.09(1H,brs),12.39 (1H,brs).
 mass: 307(M+1)$^+$.

REFERENCE EXAMPLE 1

9-amino-1,2,3,9b-tetrahydro-5H-pyrrolo[2,1-a]isoindol-5-one

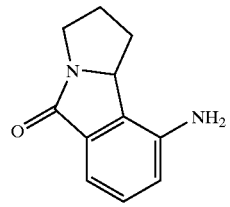

1) 1-(2-chloro-3-nitrobenzoyl)pyrrole
2-Chloro-3-nitrobenzoic acid (2 g, 10.0 mmol) and thionyl chloride (30 ml) were mixed at room temperature, and 4-dimethylaminopyridine (122 mg, 1.00 mmol) was added. The reaction mixture was refluxed for 12 hours and then concentrated to give a crude acid chloride. The acid chloride mentioned above was added to a solution of pyrrole (3.5 ml, 50.0 mmol) and triethylamine (7.0 ml, 50.0 mmol) in methylene chloride (80 ml) at room temperature. The reaction mixture was stirred at the same temperature for 6 hours and diluted with ethyl acetate. The organic layer was washed with brine and dried over anhydrous magnesium sulfate, filtered, and concentrated to give a crude compound. The crude compound was purified by silica gel column chromatography (hexane:ethyl acetate, 1:0–7:3) to give the title compound (2.43 g) as a yellow oil.

2) 9-nitro-5H-pyrrolo[2,1-a]isoindol-5-one
Potassium acetate (1.80 g, 19.2 mmol) was added to a solution of the yellow oil obtained in 1) (2.40 g, 9.60 mmol) in dimethylacetamide(180 ml), and the air in the reaction system was replaced by nitrogen. After addition of tetrakistriphenylphosphine palladium (10.10 g, 0.960 mmol) at room temperature, the reaction mixture was stirred at 130° C. overnight and then diluted with the mixture of ethyl acetate and ether (1:2). The organic layer was washed successively with water and brine, dried over anhydrous magnesium sulfate, filtered and concentrated to give a crude compound. The crude compound was purified by silica gel column chromatography (hexane:chloroform, 1:0–1:1) to give the title compound (2.24 g) as a brown solid.
$^1$H-NMR(CDCl$_3$)δ:6.34(1H,t,J=3.2 Hz), 7.10(1H,dd,J=3.3 Hz,0.85 Hz),7.21(1H,m), 7.35(1H, dd, J=8.3 Hz, 7.3 Hz),7.94(1H, dd, J=7.3 Hz, 1.0 Hz), 8.28(1H, dd, J=8.5 Hz, 1.0 Hz).

3) 10% Palladium/carbon catalyst (0.200 g) was added to a solution of the compound obtained in 2) (2.24 g) in methanol-tetrahydrofuran (1:1) (80 ml) at room temperature, and the reaction mixture was stirred under an atmosphere of hydrogen at room temperature for 12 hours. Then insolubles were removed by filtration through a Celite Pad, and the filtrate was concentrated. The obtained residue was purified by silica gel column chromatography (chloroform:methanol, 1:0–98:2–95:5) to give the compound of Reference Example 1 (1.03 g) as a brown solid.

$^1$H-NMR(DMSO-d$_6$)δ:0.80–0.93(1H,m),2.10–2.30(2H, m), 2.43–2.51(1H,m),3.18–3.24(1H,m),3.38–3.47(1H,m), 4.50(1H,dd,J=10 Hz,5.5 Hz),5.34(2H,s),6.72(1H,d,J=7.9 Hz), 6.76(1H,d,J=7.4 Hz),7.11(1H,t,J=7.6 Hz).

REFERENCE EXAMPLE 2

2-(2,4-dimethoxybenzylamino)-4-methylaniline

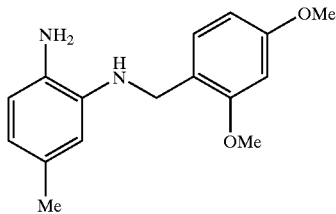

2,3-Dimethoxybenzylamine (1.05 g) and potassium carbonate (1.52 g) were added to a solution of 3-fluoro-4-nitrotoluene (0.832 g) in 1-methyl-2-pyrrolidinone (5.0 ml), and the mixture was stirred at 120° C. for 4 hours. Then, ether was added to the reaction mixture. The organic layer was washed with water and brine, dried over anhydrous magnesium sulfate and filtered. The filtrate was concentrated in vacuo to give a yellow oil. The yellow oil was dissolved in ethanol (100 ml), and to the solution were added water (50 ml), saturated aqueous ammonium chloride (50 ml) and iron dust (352 g). The mixture was heated under reflux for 3 hours while vigorous stirring. Then insolubles were removed by filtration, and the filtrate was concentrated in vacuo. The residue was dissolved in chloroform, and the organic layer was washed with water and brine and dried over anhydrous magnesium sulfate and filtered. The filtrate was concentrated in vacuo, and the residue was purified by silica gel column chromatography (hexane:ethyl acetate, 3:1 to 2:1) and then recrystallized by ethyl acetate-hexane to give the title compound (0.980 g).

$^1$H-NMR(DMSO-d$_6$)δ:1.63–1.99(m,6H),1.97–2.11(m, 2H),2.25(s,3H), 2.46(s,3H),3.32(brs,2H),3.76(s,3H),3.80(s, 1H),3.83(s,3H), 3.97(s,3H),4.21(s,1H),4.57–4.88(m,3H), 5.50(s,2H), 6.35(dd,1H,J=8.3 Hz,2.2 Hz),6.43–6.60(m,4H), 6.52(d,1H,J=2.1 Hz),6.62(d,1H,J=7.5 Hz),6.96(d,1H,J=8.2 Hz), 7.13–7.30(m,2H),7.20(d,1H,J=7.7 Hz),7.58(t,1H,J=8.1 Hz), 7.76(d,1H,J=8.2 Hz),7.94(dd,1H,J=1.58 Hz,7.7 Hz), 8.63(d,1H,J=8.0 Hz).

Industrial Applicability

According to the present invention, the compounds of the present invention have excellent activity of inhibiting the growth of cancer cells, and thus this invention is able to provide novel Cdk4 and/or Cdk6 inhibitors for treating patients with cancers.

What is claimed is:

1. A pyrazinone derivative of the general formula (I):

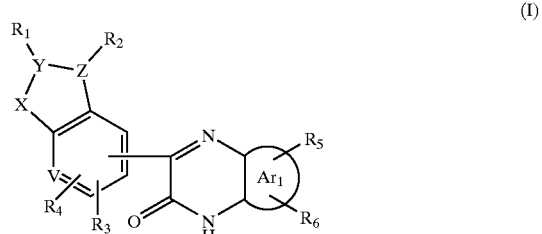

wherein

Ar$_1$ is an aryl group or a 5- or 6-membered aromatic heterocycle selected from the group consisting of pyridyl, pyrimidinyl, pyrrolyl, pyrazolyl, thienyl and pyrazinyl, said aryl or heterocycle being fused to the adjacent pyrazinone ring at the 5th and 6th positions of the pyrazinone ring;

X is CO;

Y is N;

Z is CH;

V is CH or N;

R$_1$ is a hydrogen atom; or lower alkyl, lower alkenyl or lower alkynyl wherein said lower alkyl, lower alkenyl or lower alkynyl may have one or more substituents, which are the same or different, selected from <substituent group α>; or an aliphatic or aromatic ring substituent selected from the group consisting of C$_3$–C$_8$ cycloalkyl, C$_5$–C$_8$ cycloalkenyl and aryl wherein said aliphatic or aromatic ring substituent may have one or more substituents selected from the group consisting of a substituent selected from <substituent group α> and/or a substituent selected from lower alkyl and lower alkenyl, said lower alkyl and lower alkenyl optionally having one or more substituents, which are the same or different, selected from <substituent group α>; or a lower alkyl substituted by said aliphatic or aromatic ring substituent; or a 5- or 6-membered aromatic or aliphatic heterocycle containing at least one of N, S or O, selected from <substituent group β> wherein said aromatic or aliphatic heterocycle may have one or more substituents selected from the group consisting of a substituent selected from <substituent group α> and/or a lower alkyl group which may be substituted by one or more substituents, which are the same or different, selected from an aryl group and a substituent of <substituent β>; or a lower alkyl substituted by said aromatic or aliphatic heterocycle;

R$_2$ is a hydrogen atom or lower alkyl wherein said lower alkyl may have one or more substituents, which are the same or different, selected from the group consisting of hydroxy, cyano and lower alkoxy; or R$_2$ together with Z to which R$_2$ binds, Y and R$_1$ form a 5- to 7-membered saturated aliphatic heterocycle having the following partial structure:

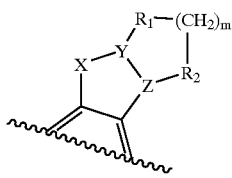

wherein $R_1$ and $R_2$
are each $CH_2$, and m is an integer of 1 to 3 and wherein said saturated aliphatic heterocycle may have one or more substituents selected from the group consisting of a substituent selected from <substituent group α> and/or a substituent selected from lower alkyl, lower alkenyl, aryl and aralkyl, said substituents being optionally substituted by one or more substituents, which are the same or different, selected from <substituent group α>;

$R_3$ and $R_4$ are each hydrogen atom, halogen atom, hydroxy, amino, lower alkyl, aryl or aralkyl wherein said lower alkyl, aryl or aralkyl may have one or more substituents, which are the same or different, selected from the group consisting of <substituent group α> and <substituent group γ>;

$R_5$ and $R_6$ are each a hydrogen atom; or a substituent selected from the group consisting of <substituent group α> and <substituent group γ>; or a group of the formula: $Y_1$—W—$Y_2$—$R_p$ wherein
$R_p$ is a hydrogen atom or lower alkyl, cyclo lower alkyl, lower alkenyl, lower alkynyl or aryl, said lower alkyl, cyclo lower alkyl, lower alkenyl, lower alkynyl or aryl optionally having one or more substituents, which are the same or different, selected from <substituent group α>; or an aromatic heterocycle selected from <substituent group δ>; or an aliphatic heterocycle selected from <substituent group ε>, W is a single bond, oxygen atom, sulfur atom, sulfinyl, sulfonyl, $NR_q$, $SO_2NR_q$, $N(R_q)SO_2NR_r$, $N(R_q)SO_2$, $CH(OR_q)$, $CONR_q$, $N(R_q)CO$, $N(R_q)CONR_r$, $NR_qCOO$, $N(R_q)CSO$, $N(R_q)COS$, $C(R_q)=CR_r$, $C\equiv C$, CO, CS, OC(O), $OC(O)NR_q$, $OC(S)NR_q$, SC(O), $SC(O)NR_q$ or C(O)O wherein $R_q$ and $R_r$ are each hydrogen atom, lower alkyl, aryl or aralkyl, $Y_1$ and $Y_2$ are each a single bond or a straight or branched lower alkylene; or an aliphatic or aromatic ring substituent selected from the group consisting of $C_3$–$C_8$ cycloalkyl, $C_5$–$C_8$ cycloalkenyl and aryl wherein said aliphatic or aromatic ring substituent may have a substituent selected from lower alkyl; lower alkyl which is substituted by $C_3$–$C_8$ cycloalkyl or aryl or $C_3$–$C_8$ cycloalkyl; or a 5- to 6-membered aromatic or aliphatic heterocycle containing at least one of N, S and O, selected from <substituent group β> wherein said aromatic or aliphatic heterocycle may be substituted with lower alkyl; lower alkyl which is substituted by $C_3$–$C_8$ cycloalkyl or aryl or $C_3$–$C_8$ cycloalkyl;

<substituent group α>, <substituent group β> <substituent group γ>, <substituent group δ>, and <substituent group ε> each have the meaning as shown below:

<substituent group α>:
hydroxy, cyano, halogen atom, nitro, carboxyl, carbamoyl, formyl, lower alkanoyl, lower alkoxy, lower alkoxycarbonyl, lower alkylcarbonyloxy, lower alkylcarbamoyl, di-lower alkylcarbamoyl, carbamoyloxy, lower alkylcarbamoyloxy, di-lower alkylcarbamoyloxy, amino, lower alkylamino, di-lower alkylamino, tri-lower alkylammonio, lower alkanoylamino, aroylamino, lower alkanoylamidino, lower alkyl-sulfonylamino, hydroxyimino, lower alkoxyimino, lower alkylthio, lower alkylsulfinyl, lower alkylsulfonyl and sulfamoyl;

<substituent group β>:
pyrrolyl, pyrrolidyl, thienyl, furyl, thiazolyl, imidazolyl, pyrazolyl, oxazolyl, isoxazolyl, pyridyl, pyrimidinyl, pyrazinyl, piperidyl, piperazinyl and morpholinyl;

<substituent group γ>:
hydroxy-lower alkyl, cyano-lower alkyl, halo-lower alkyl, carboxy-lower alkyl, carbamoyl-lower alkyl, amino-lower alkyl, lower alkyl-amino-lower alkyl, di(lower alkyl)amino-lower alkyl, and tri(lower alkyl) ammonio-lower alkyl;

<substituent group δ>:
imidazolyl, isoxazolyl, isoquinolyl, isoindolyl, indazolyl, indolyl, indoilidinyl, iothiazolyl, ethylenedioxyphenyl, oxazolyl, pyridyl, pyrazyl, pyrazinyl, pyrimidinyl, pyridazinyl, pyrazolyl, quinoxalinyl, quinolyl, dihydroisoindolyl, dihydroindolyl, thionaphthenyl, naphthyridinyl, phenazinyl, benzimidazolyl, benzoxazolyl, benzothiazolyl, benzotriazolyl, benzofuranyl, thiazolyl, thiadiazolyl, thienyl, pyrrolyl, furyl, furazanyl, triazolyl and methylenedioxyphenyl; and <substituent group ε>:
imidazolidinyl, tetrahydrofuranyl, piperazinyl, piperidyl, pyrrolidyl, pyrrolinyl, morpholino, tetrahydroquinolyl and tetrahydroisoquinolyl, or a pharmaceutically acceptable salt or ester thereof.

2. The pyrazinone derivative as claimed in claim 1, of the general formula (I-a):

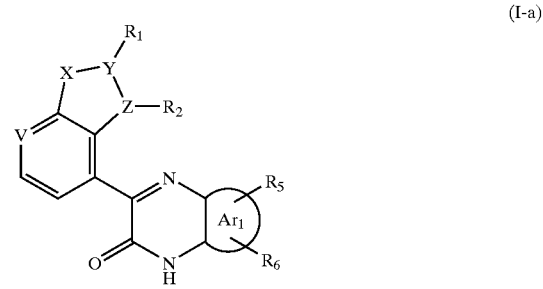

(I-a)

wherein $Ar_1$, X, Y, Z, V, $R_1$, $R_2$, $R_5$, $R_6$, <substituent group α>, <substituent group β>, <substituent group γ>, <substituent group δ> and <substituent group ε> each have the same meaning as defined in claim 1, or a pharmaceutically acceptable salt or ester thereof.

3. The compound as claimed in claim 2 or a pharmaceutically acceptable salt or ester thereof, wherein the <substituent group α> is hydroxy, halogen atom, nitro, carboxyl, lower alkoxy, lower alkoxycarbonyl, and lower alkylcarbonyloxy, the <substituent group β> is pyrrolidyl, pyridyl, pyrimidinyl, piperidyl, piperazinyl and morpholinyl, and the <substituent group γ> is hydroxy-lower alkyl, and halo-lower alkyl.

4. The compound as claimed in claim 3 or a pharmaceutically acceptable salt or ester thereof, wherein $Ar_1$ is phenyl, pyridyl or pyrimidinyl;

$R_5$ and $R_6$ are the same or different and are each a hydrogen atom; or a substituent selected from the group consisting of <substituent group α> and <substituent group γ>; or a group of the formula: $Y_1-W-Y_2-R_p$ wherein $R_p$ is lower alkyl or phenyl, said phenyl group optionally having one or more substituents, which are the same or different, selected from <substituent group α>; W is a single bond, oxygen atom or sulfonyl; $Y_1$ and $Y_2$ are the same or different and are each a single bond or lower alkylene; or a 5- to 6-membered aliphatic heterocycle containing at least one nitrogen atom, selected from <substituent group β> wherein said aliphatic heterocycle may have a substituent selected from lower alkyl; lower alkyl which is substituted by $C_5-C_6$ cycloalkyl or phenyl; or $C_5-C_6$ cycloalkyl.

5. The compound as claimed in claim 4 or a pharmaceutically acceptable salt or ester thereof, wherein $R_1$ is lower alkyl, said lower alkyl optionally having one or more substituents, which are the same or different, selected from <substituent group α>; or an aliphatic or aromatic ring substituent selected from the group consisting of $C_5-C_6$ cycloalkyl, $C_5-C_6$ cycloalkenyl and phenyl wherein said aliphatic or aromatic ring substituent may have one or more substituents selected from the group consisting of a substituent selected from <substituent group α>, and/or lower alkyl group substituted by one or more substituents, which are the same or different, selczted from <substituent group α>; or a lower alkyl substituted by said aliphatic or aromatic ring substituent; or an aromatic or aliphatic heterocycle containing at least one nitrogen atom, selected from <substituent group β> wherein said aromatic or aliphatic heterocycle may have one or more substituents selected from the group consisting of a substituent selected from <substituent group α> and/or lower alkyl substituted by one or more substituents, which are the same or different, selected from phenyl and <substituent group β>; or a lower alkyl substituted by said aromatic or aliphatic heterocycle.

6. The compound as claimed in claim 5 or a pharmaceutically acceptable salt or ester thereof, wherein V is CH and $R_2$ is hydrogen atom.

7. The compound as claimed in claim 2 or a pharmaceutically acceptable salt or ester thereof, wherein $Ar_1$ is phenyl or pyridyl;

V is CH;

$R_1$ is lower alkyl wherein said lower alkyl group may have one or more substituents, which are the same or different, selected from <substituent group α>; or an aliphatic or aromatic ring substituent selected from the group consisting of $C_5-C_6$ cycloalkyl and phenyl wherein said aliphatic or aromatic cyclic substituent may have one or more substituents selected from the group consisting of a substituent selected from <substituent group α>, and/or lower alkyl optionally substituted by one or more substituents, which are the same or different, selected from <substituent group α>; or a lower alkyl substituted by said aliphatic or aromatic ring substituent; or an aliphatic or aromatic heterocycle containing at least one nitrogen atom selected from <substituent group β> wherein said aliphatic or aromatic heterocycle may have one or more substituents selected from <substituent group α> and/or lower alkyl optionally substituted by one or more substituents, which are the same or different, selected from phenyl and <substituent group β>; or a lower alkyl substituted by said aromatic or aliphatic heterocycle; and $R_5$ and $R_6$ are the same or different and are each a hydrogen atom; or a substituent selected from the group consisting of <substituent group α> and <substituent group γ>; or a group of the formula: $Y_1-W-Y_2-R_p$ wherein $R_p$ is lower alkyl or phenyl, said phenyl group optionally having one or more substituents, which are the same or different, selected from <substituent group α>; W is a single bond, or an oxygen atom; $Y_1$ and $Y_2$ are the same or different and are each a single bond or lower alkylene; or a 5- to 6-membered aliphatic heterocycle having at least one nitrogen atom selected from <substituent group β> wherein said aliphatic heterocycle may have a substituent selected from lower alkyl; lower alkyl which is substituted by $C_5-C_6$ cycloalkyl or phenyl; or $C_5-C_6$ cycloalkyl.

8. The compound as claimed in claim 7 or a pharmaceutically acceptable salt or ester thereof, wherein the <substituent group α> is hydroxy, cyano, halogen atom, nitro, carboxyl, carbamoyl, lower alkanoyl, lower alkoxy, lower alkoxycarbonyl, lower alkylcarbonyloxy, lower alkylcarbamoyl, di-lower alkylcarbamoyl, carbamoyloxy, lower alkylcarbamoyloxy, amino, lower alkylamino, di-lower alkylamino, tri-lower alkylammonio, lower alkanoylamino, aroylamino, lower alkyl-sulfonylamino, hydroxyimino, lower alkoxyimino, lower alkylthio, lower alkylsulfonyl and sulfamoyl; the <substituent group β> is pyrrolyl, pyrrolidyl, thiazolyl, pyrazolyl, oxazolyl, isoxazolyl, pyridyl, pyrimidinyl, pyrazinyl, piperidyl, piperazinyl and morpholinyl, and the <substituent group γ> is hydroxy-lower alkyl, halo-lower alkyl, carbamoyl-lower alkyl, amino-lower alkyl, lower alkyl-amino-lower alkyl, and tri(lower alkyl-ammonio)-lower alkyl.

9. The compound as claimed in claim 2 or a pharmaceutically acceptable salt or ester thereof, wherein the pyrazinone derivative is 9-(3-oxo-3,4-dihydroquinoxalin-2-yl)-1,2,3,9b-tetrahydro-5H-pyrrolo[2,1-a]isoindol-5-one, 9-(3-oxo-6,7-dimethyl-3,4-dihydroquinoxalin-2-yl)-1,2,3,9b-tetrahydro-5H-pyrrolo[2,1-a]isoindol-5-one, 3-(2-cyclopentyl-1-oxo-2,3-dihydro-1H-isoindol-4-yl)-7-methylquinoxalin-2(1H)-one, or 7-(1-benzylpyrrolidin-3-yl)-3-(2-cyclopentyl-1-oxo-2,3-dihydro-1H-isoindol-4-yl)quinoxalin-2(1H)-one.

10. A pharmaceutical composition comprising as an active ingredient one or more pyrazinone derivatives as claimed in claim 1, together with a pharmaceutically acceptable carrier or diluent.

11. A method of treating a cancer selected from the group consisting of brain cancer, breast cancer, stomach cancer, colon cancer and osteosarcoma, comprising administering to a patient in need thereof a therapeutically effective amount of one or more pyrazinone derivatives as claimed in claim 1, together with a pharmaceutically acceptable carrier or diluent.

12. A process for preparing a pyrazinone derivative of the general formula (I) as claimed in claim 1, which comprises reacting a compound of the general formula (II):

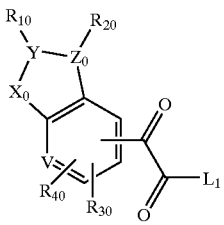

(II)

wherein
$X_0$ is CO;
Y is N;
$Z_0$ is CH;
V is CH or N;
$L_1$ is a leaving group;
$R_{10}$ is a hydrogen atom; or
lower alkyl, lower alkenyl or lower alkynyl wherein said lower alkyl, lower alkenyl or lower alkynyl may have one or more substituents, which are the same or different, selected from <substituent group $\alpha_0$>; or
an aliphatic or aromatic ring substituent selected from the group consisting of $C_3$–$C_8$ cycloalkyl, $C_5$–$C_8$ cycloalkenyl and aryl wherein said aliphatic or aromatic ring substituent may have one or more substituents selected from the group consisting of a substituent selected from <substituent group $\alpha_0$> and/or a substituent selected from the group consisting of lower alkyl and lower alkenyl, said lower alkyl and lower alkenyl being optionally substituted by one or more substituents, which are the same or different, selected from <substituent group $\alpha_0$>; or a lower alkyl substituted by said aliphatic or aromatic ring substituent(s); or
a 5- or 6-membered aromatic or aliphatic heterocycle containing at least one of N, S and O, selected from <substituent group β> wherein said aromatic or aliphatic heterocycle may have one or more substituents selected from the group consisting of a substituted selected from <substituent group α> and/or a lower alkyl group optionally substituted by one or more substituents, which are the same or different, selected from an aryl group and <substituent group β>; or a lower alkyl substituted by said aromatic or aliphatic heterocycle;
$R_{20}$ is hydrogen atom or lower alkyl wherein said lower alkyl may have one or more substituents, which are the same or different, selected from the group consisting of optionally protected hydroxy, cyano and lower alkoxy; or
$R_{20}$ together with $Z_0$ to which $R_{20}$ binds, Y and $R_{10}$ form a 5- to 7-membered saturated aliphatic heterocycle having the following partial structure:

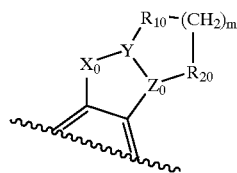

wherein $R_{10}$ and $R_{20}$ are each $CH_2$, and m is an integer of 1 to 3 and wherein said saturated aliphatic heterocycle may have one or more substituents, which are the same or different, selected from the group consisting of a substituent selected from <substituent group $\alpha_0$> and/or a substituent selected from lower alkyl, lower alkenyl, aryl and aralkyl, said substituent being optionally substituted by one or more substituents, which are the same or different, selected from <substituent group $\alpha_0$>, $R_{30}$ and $R_{40}$ are the same or different and are each hydrogen atom, halogen atom, optionally protected hydroxy, optionally protected amino acid, lower alkyl, aryl or aralkyl wherein said lower alkyl, aryl and aralkyl may have one or more substituents, which are the same or different, selected from the group consisting of <substituent group $\alpha_0$> and <substituent group $\gamma_0$>;

wherein the meaning of <substituent group $\alpha_0$> and <substituent group $\gamma_0$> is given below, and <substituent group β> has the same meaning as defined in claim 1, <substituent group $\alpha_0$>:
optionally protected hydroxy, cyano, halogen atom, nitro, optionally protected carboxyl, carbamoyl, formyl, lower alkanoyl, lower alkoxy, lower alkoxycarbonyl, lower alkylcarbonyloxy, lower alkylcarbamoyl, di-lower alkylcarbamoyl, carbamoyloxy, lower alkylcarbamoyloxy, di-lower alkylcarbamoyloxy, optionally protected amino, lower alkylamino, di-lower alkylamino, tri-lower alkylammonio, lower alkanoylamino, aroylamino, lower alkanoylamidino, lower alkylsulfonylamino, optionally protected hydroxyimino, lower alkoxyimino, lower alkylthio, lower alkylsulfinyl, lower alkylsulfonyl and sulfamoyl;

<substituent group $\gamma_0$>:
optionally protected hydroxy-lower alkyl, cyano-lower alkyl, halo-lower alkyl, optionally protected carboxyl-lower alkyl, carbamoyl-lower alkyl, optionally protected amino-lower alkyl, lower alkyl-amino-lower alkyl, di(lower alkylamino)-lower alkyl, and tri(lower alkyl)ammonio-lower alkyl;

with a compound of the general formula (III):

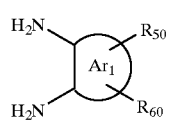

(III)

wherein $Ar_1$ is an aryl or a 5- or 6-membered aromatic heterocycle selected from the group consisting of pyridyl, pyrimidinyl, pyrrolyl, pyrazolyl, thienyl and pyrazinyl, said aryl or heterocycle being fused at the 5th and 6th positions of the pyrazinone ring;

$R_{50}$ and $R_{60}$ are the same or different and are each a hydrogen atom; or
a substituent selected from the group consisting of <substituent group $\alpha_0$> and <substituent group $\gamma_0$>; or
a group of the formula: $Y_1$—W—$Y_2$—$R_{p0}$ wherein
$R_{p0}$ is hydrogen atom; or lower alkyl, cyclo lower alkyl, lower alkenyl, lower alkynyl or aryl wherein said lower alkyl, cyclo lower alkyl, lower alkenyl, lower alkynyl or aryl may have one or more substituents, which are the same or different, selected from <substituent group $\alpha_0$>; or an aromatic heterocycle selected from <substituent group δ>; or an aliphatic heterocycle selected from <substituent group ε>, W is a single bond, oxygen atom, sulfur atom, sulfinyl, sulfonyl, $NR_{q0}$, $SO_2NR_{q0}$, $N(R_{q0})SO_2NR_{r0}$, $N(R_{q0})SO_2$, $CH(OR_{q0})$, $CONR_{q0}$, $N(R_{q0})CO$, $N(R_{q0})CONR_{r0}$, $N(R_{q0})COO$, $N(R_{q0})CSO$, $N(R_{q0})COS$, $C(R_{q0})=CR_{r0}$, $C\equiv C$, CO, CS, OC(O), $OC(O)NR_{q0}$, $OC(S)NR_{q0}$, SC(O), $SC(O)NR_{q0}$ or C(O)O wherein $R_{q0}$ and $R_{r0}$ are each hydrogen atom, lower alkyl, aryl or aralkyl, $Y_1$ and $Y_2$ are the same or different and are each a single bond or a straight or branched lower alkylene; or an aliphatic or aromatic ring substituent selected from the group consisting of $C_3$–$C_8$ cyclkoalkyl, $C_5$–$C_8$ cycloalkenyl and aryl wherein said aliphatic or aromatic ring group may have a substituent selected from lower alkyl; lower alkyl which is substituted by $C_3$–$C_8$ cycloalkyl or aryl; or $C_3$–$C_8$ cycloalkyl; or a 5- to 6-membered aromatic or aliphatic heterocycle containing at least one of N, S and O selected from <substituent group β> wherein said aromatic or aliphatic heterocycle may be substituted with lower alkyl; lower alkyl which is substituted by $C_3$–$C_8$ cycloalkyl or aryl; or $C_3$–$C_8$ cycloalkyl; and wherein the <substituent group $α_0$> and <substituent group $γ_0$> each have the same meaning as defined above, and the <substituent group β>, <substituent group δ> and <substituent group ε> each have the same meaning as defined in claim 19, and optionally removing the protecting group from the resultant compound of the general formula (IV):

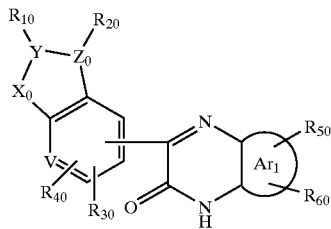

(IV)

wherein $Ar_1$, $X_0$, Y, $Z_0$, V, $R_{10}$, $R_{20}$, $R_{30}$, $R_{40}$, $R_{50}$, $R_{60}$, <substituent group $α_0$>, <substituent β>, <substituent group $γ_0$>, <substituent group δ> and <substituent group ε> each have the same meanings as defined above, thereby to obtain a compound of the general formula (I):

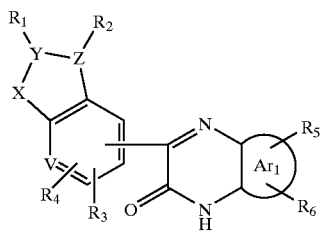

(I)

wherein $Ar_1$, X, Y, Z, V, $R_1$, $R_2$, $R_3$, $R_4$, $R_5$, $R_6$, <substituent group α>, <substituent group β>, <substituent group γ>, <substituent group δ> and <substituent group ε> each have the same meanings as defined in claim 1;

or alternatively reacting the compound of the above formula (II) with a compound of the general formula (III-c):

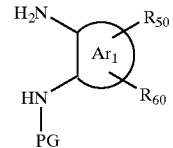

(III-c)

wherein PG is a protecting group for amino group, and $Ar_1$, $R_{50}$, $R_{60}$, <substituent group $α_0$>, <substituent group β>, <substituent group $γ_0$>, <substituent group δ> and <substituent group ε> each have the same meanings as defined above; and optionally removing the protecting group from the regioselectively obtained compound of the general formula (IV-c):

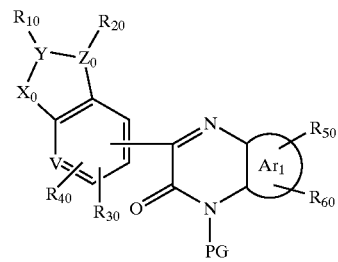

(IV-c)

wherein $Ar_1$, $X_0$, Y, $Z_0$, V, $R_{10}$, $R_{20}$, $R_{30}$, $R_{40}$, $R_{50}$, $R_{60}$, PG, <substituent group $α_0$><substituent group β>, <substituent group $γ_0$>, <substituent group δ> and <substituent group ε> each have the same meanings as defined above, thereby to obtain a compound of the general formula (I):

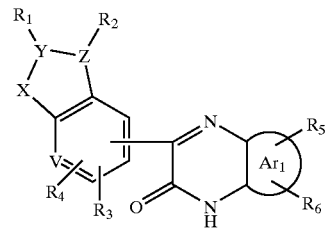

(I)

wherein $Ar_1$, X, Y, Z, V, $R_1$, $R_2$, $R_3$, $R_4$, $R_5$, $R_6$, <substituent group α>, <substituent group β>, <substituent group γ>, <substituent group δ> and <substituent group ε> each have the same meanings as defined in claim 1.

13. A process for preparing a pyrazinone derivative of the general formula (I) as claimed in claim 1, which comprises reacting a compound of the general formula (II-d):

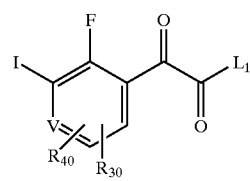

(II-d)

wherein

V is CH or N, $L_1$ is a leaving group;

$R_{30}$ and $R_{40}$ are the same or different and are each hydrogen atom, halogen atom, optionally protected hydroxy, optionally protected amino acid, lower alkyl, aryl or aralkyl wherein said lower alkyl, aryl and aralkyl may have one or more substituents, which are the same or different, selected from the group consisting of <substituent group $\alpha_0$> and <substituent group $\gamma_0$>, wherein the meaning of <substituent group $\alpha_0$> and <substituent group $\gamma_0$> is given below;

<substituent group $\alpha_0$>:

optionally protected hydroxy, cyano, halogen atom, nitro, optionally protected carboxyl, carbamoyl, formyl, lower alkanoyl, lower alkoxy, lower alkoxycarbonyl, lower alkylcarbonyloxy, lower alkylcarbamoyl, di-lower alkylcarbamoyl, carbamoyloxy, lower alkylcarbamoyloxy, di-lower alkylcarbamoyloxy, optionally protected amino, lower alkylamino, di-lower alkylamino, tri-lower alkylammonio, lower alkanoylamino, aroylamino, lower alkanoylamidino, lower alkylsulfonylamino, optionally protected hydroxyimino, lower alkoxyimino, lower alkylthio, lower alkylsulfinyl, lower alkylsulfonyl and sulfamoyl;

<substituent group $\gamma_0$>:

optionally protected hydroxy-lower alkyl, cyano-lower alkyl, halo-lower alkyl, optionally protected carboxyl-lower alkyl, carbamoyl-lower alkyl, optionally protected amino-lower alkyl, lower alkyl-amino-lower alkyl, di(lower alkylamino)-lower alkyl, and tri(lower alkyl)ammonio-lower alkyl;

with a compound of the general formula (III-c):

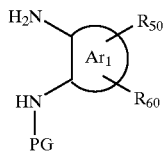

(III-c)

wherein $Ar_1$ is an aryl or a 5- or 6-membered aromatic heterocycle selected from the group consisting of pyridyl, pyrimidinyl, pyrrolyl, pyrazolyl, thienyl and pyrazinyl, said aryl or heterocycle being fused at the 5th and 6th positions of the pyrazinone ring;

PG is a protecting group for amino group;

$R_{50}$ and $R_{60}$ are the same or different and are each a hydrogen atom; or a substituent selected from the group consisting of <substituent group $\alpha_0$> and <substituent group $\gamma_0$>; or a group of the formula: $Y_1$—W—$Y_2$—$R_{p0}$ wherein $R_{p0}$ is hydrogen atom; or lower alkyl, cyclo lower alkyl, lower alkenyl, lower alkynyl or aryl wherein said lower alkyl, cyclo lower alkyl, lower alkenyl, lower alkynyl or aryl may have one or more substituents, which are the same or different, selected from <substituent group $\alpha_0$ >; or an aromatic heterocycle selected from <substituent group $\delta$>; or an aliphatic heterocycle selected from <substituent group $\epsilon$>, W is a single bond, oxygen atom, sulfur atom, sulfinyl, sulfonyl, $NR_{q0}$, $SO_2NR_{q0}$, $N(R_{q0})SO_2NR_{r0}$, $N(R_{q0})SO_2$, $CH(OR_{q0})$, $CONR_{q0}$, $N(R_{q0})CO$, $N(R_{q0})CONR_{r0}$, $N(R_{q0})COO$, $N(R_{q0})CSO$, $N(R_{q0})COS$, $C(R_{q0})$=$CR_{r0}$, C≡C, CO, CS, OC(O), OC(O)$NR_{q0}$, OC(S)$NR_{q0}$, SC(O), SC(O)$NR_{q0}$ or C(O)O wherein $R_{q0}$ and $R_{r0}$ are each hydrogen atom, lower alkyl, aryl or aralkyl, $Y_1$ and $Y_2$ are the same or different and are each a single bond or a straight or branched lower alkylene; or an aliphatic or aromatic ring substituent selected from the group consisting of $C_3$–$C_8$ cycloalkyl, $C_5$–$C_8$ cycloalkenyl and aryl wherein said aliphatic or aromatic ring group may have a substituent selected from lower alkyl; lower alkyl which is substituted by $C_3$–$C_8$ cycloalkyl or aryl; or $C_3$–$C_8$ cycloalkyl; or a 5- to 6-membered aromatic or aliphatic heterocycle containing at least one of N, S and O selected from <substituent group $\beta$> wherein said aromatic or aliphatic heterocycle may be substituted with lower alkyl; lower alkyl which is substituted by $C_3$–$C_8$ cycloalkyl or aryl or $C_3$–$C_8$ cycloalkyl; and wherein the <substituent group $\alpha_0$> and <substituent group $\gamma_0$> each have the same meanings as defined above, and the <substituent group $\beta$>, <substituent group $\delta$> and <substituent group $\epsilon$> each have the same meanings as defined in claim 1, wherein <substituent group $\alpha_0$> and <substituent group $\gamma_0$> have the same meanings as defined above;

wherein <substituent group $\beta$>, <substituent group $\delta$> and <substituent group $\epsilon$> each have the same meanings as defined in claim 1;

reacting the resultant compound of the general formula (V-d):

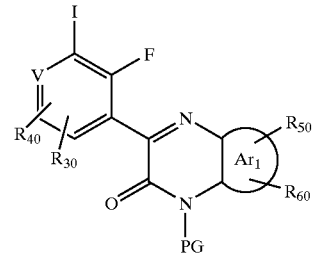

(V-d)

wherein $Ar_1$, V, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> each have the same meanings as defined above;

with carbon monoxide in the presence of a palladium catalyst to obtain a compound of the general formula (V-e):

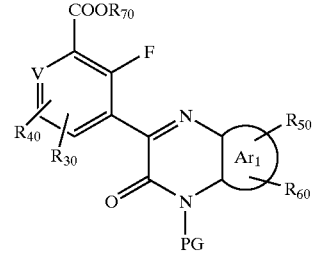

(V-e)

wherein $R_{70}$ is lower alkyl, and $Ar_1$, V, $R_{30}$, $R_{40}$, $R_{50}$, $R_{60}$, PG, <substituent group $\alpha_0$>, <substituent group $\beta$>, <substituent group $\gamma_0$>, <substituent group $\delta$> and <substituent group $\epsilon$> each have the same meanings as defined above; and then hydrolyzing the benzoic acid ester moiety in the compound of the above formula (V-e), condensing the resultant compound of the general formula (X):

(X)

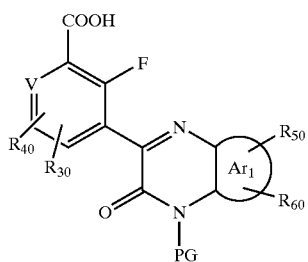

wherein Ar$_1$, V, R$_{30}$, R$_{40}$, R$_{50}$, R$_{60}$, PG, <substituent group α$_0$>, <substituent group β>, <substituent group γ$_0$>, <substituent group δ> and <substituent group ε> each have the same meanings as defined above, with an α-amino acid derivative of the general formula (VII-b):

(VII-b)

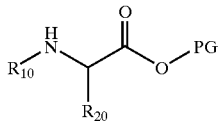

wherein R$_{10}$, R$_{20}$ and PG each have the same meanings as defined above, subjecting the resultant compound to intramolecular cyclization under basic conditions; removing the carboxyl-protecting group PG on the pyrrolidinone ring from the resultant compound of the general formula (VIII-b):

(VIII-b)

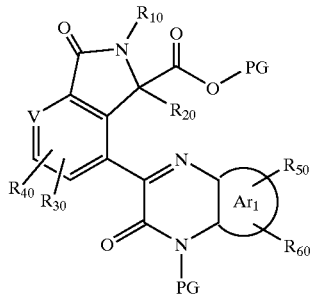

wherein Ar$_1$, V, R$_{10}$, R$_{20}$, R$_{30}$, R$_{40}$, R$_{50}$, R$_{60}$, PG, <substituent group α$_0$>, <substituent group β> <substituent group γ$_0$>, <substituent group δ> and <substituent group ε> each have the same meanings as defined above, decarboxylating the carboxyl group of the resultant compound, and optionally removing the protecting group PG from the resultant compound of the general formula (IV-gg):

(IV-gg)

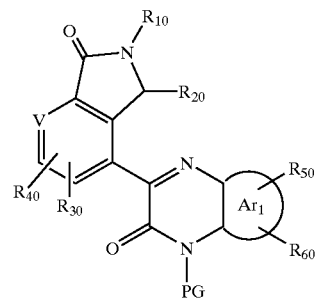

wherein Ar$_1$, V, R$_{10}$, R$_{20}$, R$_{30}$, R$_{40}$, R$_{50}$, R$_{60}$, PG, <substituent group α$_0$>, <substituent group β>, <substituent group γ$_0$>, <substituent group δ> and <substituent group ε> each have the same meanings as defined above, thereby to obtain a compound of the general formula (I-gg):

(I-gg)

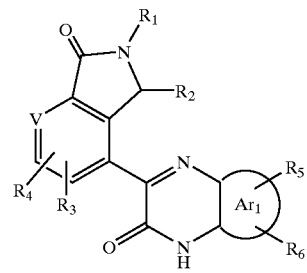

wherein Ar$_1$, V, R$_1$, R$_2$, R$_3$, R$_4$, R$_5$, R$_6$, >substituent group α>, <substituent group β>, <substituent group γ>, <substituent group δ> and <substituent group ε> each have the same meanings as defined in claim 1, to obtain a compound of the general formula (I) wherein X is CO, Y is N and Z is CH.

* * * * *

UNITED STATES PATENT AND TRADEMARK OFFICE
CERTIFICATE OF CORRECTION

PATENT NO.   : 6,914,062 B2
DATED        : July 5, 2005
INVENTOR(S)  : Takashi Hayama et al.

It is certified that error appears in the above-identified patent and that said Letters Patent is hereby corrected as shown below:

<u>Column 46,</u>
Table 4, Working Example No. 2, change " " " to -- idem --.
Table 4, Working Example No. 3, change " " " to -- idem --.

<u>Column 47,</u>
Table 4, Working Example No. 4, change " " " to -- idem --.
Table 4, Working Example No. 5, change " " " to -- idem --.
Table 4, Working Example No. 6, change " " " to -- idem --.
Table 4, Working Example No. 7, change " " " to -- idem --.
Table 4, Working Example No. 9, change " " " to -- idem --.
Table 4, Working Example No. 10, change " " " to -- idem --.
Table 4, Working Example No. 11, change " " " to -- idem --.

<u>Column 49,</u>
Table 4, Working Example No. 12, change " " " to -- idem --.
Table 4, Working Example No. 13, change " " " to -- idem --.
Table 5, Working Example No. 16, change " " " to -- idem --.

<u>Column 50,</u>
Table 5, Working Example No. 17, change " " " to -- idem --.
Table 5, Working Example No. 18, change " " " to -- idem --.
Table 5, Working Example No. 19, change " " " to -- idem --.

<u>Column 51,</u>
Table 5, Working Example No. 20, change " " " to -- idem --.
Table 5, Working Example No. 21, change " " " to -- idem --.
Table 5, Working Example No. 24, change " " " to -- idem --.
Table 5, Working Example No. 25, change " " " to -- idem --.

<u>Column 52,</u>
Table 5, Working Example No. 26, change " " " to -- idem --.
Table 5, Working Example No. 27, change " " " to -- idem --.

<u>Column 53,</u>
Table 6, Working Example No. 30, change " " " to -- idem --.
Table 6, Working Example No. 31, change " " " to -- idem --.
Table 6, Working Example No. 32, change " " " to -- idem --.
Table 6, Working Example No. 33, change " " " to -- idem --.
Table 6, Working Example No. 34, change " " " to -- idem --.

UNITED STATES PATENT AND TRADEMARK OFFICE
CERTIFICATE OF CORRECTION

PATENT NO. : 6,914,062 B2
DATED : July 5, 2005
INVENTOR(S) : Takashi Hayama et al.

It is certified that error appears in the above-identified patent and that said Letters Patent is hereby corrected as shown below:

Column 54,
Table 6, Working Example No. 35, change """ to -- idem --.
Table 6, Working Example No. 37, change """ to -- idem --.
Table 6, Working Example No. 38, change """ to -- idem --.
Table 6, Working Example No. 39, change """ to -- idem --.

Column 55,
Table 6, Working Example No. 40, change """ to -- idem --.
Table 6, Working Example No. 41, change """ to -- idem --.

Column 56,
Table 7, Working Example No. 44, change """ to -- idem --.
Table 7, Working Example No. 45, change """ to -- idem --.
Table 7, Working Example No. 46, change """ to -- idem --.
Table 7, Working Example No. 47, change """ to -- idem --.
Table 7, Working Example No. 48, change """ to -- idem --.

Column 57,
Table 7, Working Example No. 49, change """ to -- idem --.
Table 7, Working Example No. 51, change """ to -- idem --.
Table 7, Working Example No. 52, change """ to -- idem --.
Table 7, Working Example No. 53, change """ to -- idem --.

Column 58,
Table 7, Working Example No. 54, change """ to -- idem --.
Table 7, Working Example No. 55, change """ to -- idem --.

Column 59,
Table 8, Working Example No. 58, change """ to -- idem --.
Table 8, Working Example No. 59, change """ to -- idem --.
Table 8, Working Example No. 60, change """ to -- idem --.
Table 8, Working Example No. 61, change """ to -- idem --.

Column 60,
Table 8, Working Example No. 62, change """ to -- idem --.
Table 8, Working Example No. 63, change """ to -- idem --.
Table 8, Working Example No. 65, change """ to -- idem --.
Table 8, Working Example No. 66, change """ to -- idem --.

Column 61,
Table 8, Working Example No. 68, change """ to -- idem --.

UNITED STATES PATENT AND TRADEMARK OFFICE
CERTIFICATE OF CORRECTION

PATENT NO. : 6,914,062 B2
DATED : July 5, 2005
INVENTOR(S) : Takashi Hayama et al.

It is certified that error appears in the above-identified patent and that said Letters Patent is hereby corrected as shown below:

Column 62,
Table 8, Working Example No. 69, change """ to -- idem --.
Table 8, Working Example No. 70, change """ to -- idem --.
Table 9, Working Example No. 72, change """ to -- idem --.
Table 9, Working Example No. 73, change """ to -- idem --.

Column 63,
Table 9, Working Example No. 74, change """ to -- idem --.
Table 9, Working Example No. 75, change """ to -- idem --.
Table 9, Working Example No. 76, change """ to -- idem --.
Table 9, Working Example No. 77, change """ to -- idem --.
Table 9, Working Example No. 79, change """ to -- idem --.
Table 9, Working Example No. 80, change """ to -- idem --.

Column 65,
Table 9, Working Example No. 82, change """ to -- idem --.
Table 9, Working Example No. 83, change """ to -- idem --.
Table 9, Working Example No. 84, change """ to -- idem --.

Column 67,
Table 10, Working Example No. 86, change """ to -- idem --.
Table 10, Working Example No. 87, change """ to -- idem --.
Table 10, Working Example No. 89, change """ to -- idem --.
Table 10, Working Example No. 90, change """ to -- idem --.

Column 69,
Table 10, Working Example No. 94, change """ to -- idem --.
Table 10, Working Example No. 96, change """ to -- idem --.

Column 71,
Table 10, Working Example No. 97, change """ to -- idem --.
Table 10, Working Example No. 98, change """ to -- idem --.
Table 11, Working Example No. 100, change """ to -- idem --.

Column 73,
Table 11, Working Example No. 102, change """ to -- idem --.
Table 11, Working Example No. 103, change """ to -- idem --.
Table 11, Working Example No. 105, change """ to -- idem --.

UNITED STATES PATENT AND TRADEMARK OFFICE
CERTIFICATE OF CORRECTION

PATENT NO.     : 6,914,062 B2
DATED          : July 5, 2005
INVENTOR(S)    : Takashi Hayama et al.

It is certified that error appears in the above-identified patent and that said Letters Patent is hereby corrected as shown below:

Column 75,
Table 11, Working Example No. 109, change """ to -- idem --.
Table 11, Working Example No. 111, change """ to -- idem --.
Table 11, Working Example No. 112, change """ to -- idem --.

Signed and Sealed this

Twenty-first Day of March, 2006

JON W. DUDAS
*Director of the United States Patent and Trademark Office*